US012637518B2

(12) United States Patent　　(10) Patent No.:　US 12,637,518 B2
Curran　　　　　　　　　　　　　　(45) Date of Patent:　　May 26, 2026

(54) DUAL SPECIFICITY ANTIBODIES TO HUMAN PD-L1 AND PD-L2 AND METHODS OF USE THEREFOR

(71) Applicant: Board of Regents, The University of Texas System, Austin, TX (US)

(72) Inventor: Michael Curran, Houston, TX (US)

(73) Assignee: BOARD OF REGENTS, THE UNIVERSITY OF TEXAS SYSTEM, Austin, TX (US)

( * ) Notice: Subject to any disclaimer, the term of this patent is extended or adjusted under 35 U.S.C. 154(b) by 583 days.

(21) Appl. No.: 18/194,360

(22) Filed: Mar. 31, 2023

(65) Prior Publication Data

US 2023/0365708 A1　　Nov. 16, 2023

Related U.S. Application Data

(60) Provisional application No. 63/378,196, filed on Oct. 3, 2022, provisional application No. 63/326,456, filed on Apr. 1, 2022.

(51) Int. Cl.
　　*C07K 16/28*　　　(2006.01)
　　*A61P 35/00*　　　(2006.01)
　　*G01N 33/574*　　(2006.01)
(52) U.S. Cl.
　　CPC .......... *C07K 16/2896* (2013.01); *A61P 35/00* (2018.01); *G01N 33/57484* (2013.01); *C07K 2317/24* (2013.01); *C07K 2317/31* (2013.01); *C07K 2317/565* (2013.01); *C07K 2317/92* (2013.01)
(58) Field of Classification Search
　　CPC ............ C07K 16/2896; C07K 2317/24; C07K 2317/31; C07K 2317/565; C07K 2317/92; C07K 2317/33; C07K 2317/35; C07K 2317/32; C07K 16/2827; A61P 35/00; G01N 33/57484; A61K 2039/505
See application file for complete search history.

(56) References Cited

U.S. PATENT DOCUMENTS

| | | | |
|---|---|---|---|
| 5,595,756 | A | 1/1997 | Bally et al. |
| 9,567,399 | B1 | 2/2017 | Campbell et al. |
| 10,101,333 | B2 | 10/2018 | Smider et al. |
| 2003/0194704 | A1 | 10/2003 | Penn et al. |
| 2004/0131613 | A1 | 7/2004 | Watkins et al. |
| 2005/0059113 | A1 | 3/2005 | Bedian et al. |

(Continued)

FOREIGN PATENT DOCUMENTS

| | | |
|---|---|---|
| WO | WO 2005/032177 A2 | 3/2005 |
| WO | WO 2007/030642 A2 | 3/2007 |

(Continued)

OTHER PUBLICATIONS

Almagro et al., "Humanization of antibodies," *Frontiers in Bioscience*, 13:1619-1633, 2008.

(Continued)

*Primary Examiner* — Joanne Hama
*Assistant Examiner* — Matthew Curran Metcalf
(74) *Attorney, Agent, or Firm* — pH IP Law

(57)　　　　ABSTRACT

The present disclosure is directed to dual specific antibodies, which bind to both PD-L1 and PD-L2, and methods of using such antibodies to treat cancers, such as those that express or overexpress PD-L1, PD-L2, or both.

20 Claims, 30 Drawing Sheets

Specification includes a Sequence Listing.

(56) References Cited

U.S. PATENT DOCUMENTS

| | | | |
|---|---|---|---|
| 2008/0213251 | A1 | 9/2008 | Sexton et al. |
| 2008/0262203 | A1 | 10/2008 | Clegg et al. |
| 2011/0110956 | A1 | 5/2011 | Rothe et al. |
| 2013/0156781 | A1 | 6/2013 | Dmitrov et al. |
| 2015/0329642 | A1 | 11/2015 | Neijssen et al. |
| 2016/0311903 | A1 | 10/2016 | West et al. |
| 2017/0007693 | A1 | 1/2017 | Weiner et al. |
| 2017/0088620 | A1 | 3/2017 | Nioi et al. |
| 2017/0137522 | A1 | 5/2017 | Queva et al. |
| 2017/0158767 | A1 | 6/2017 | Korman et al. |
| 2017/0306028 | A1 | 10/2017 | Knopf et al. |
| 2017/0355757 | A1 | 12/2017 | Hu et al. |
| 2021/0139591 | A1 | 5/2021 | Curran et al. |
| 2021/0198360 | A1 | 7/2021 | Curran et al. |
| 2021/0214445 | A1 | 7/2021 | Curran et al. |
| 2023/0174661 | A1 | 6/2023 | Carran et al. |

FOREIGN PATENT DOCUMENTS

| | | | |
|---|---|---|---|
| WO | WO 2007/097923 A2 | 8/2007 | |
| WO | WO 2011/066342 A2 | 6/2011 | |
| WO | WO 2011/066389 A1 | 6/2011 | |
| WO | WO 2013/079174 A1 | 6/2013 | |
| WO | WO 2014/022758 A1 | 2/2014 | |
| WO | WO 2016/081639 A1 | 5/2016 | |
| WO | WO 2016/111645 A1 | 7/2016 | |
| WO | WO 2016/144728 A2 | 9/2016 | |
| WO | WO 2016/160792 A1 | 10/2016 | |
| WO | WO 2017/053250 A1 | 3/2017 | |
| WO | WO 2017/070170 A1 | 4/2017 | |
| WO | WO 2017/106453 A1 | 6/2017 | |
| WO | WO 2017/118321 A1 | 7/2017 | |
| WO | WO 2017/156479 A1 | 9/2017 | |
| WO | WO 2017/172517 A1 | 10/2017 | |
| WO | WO 2017/200796 A1 | 11/2017 | |
| WO | WO 2019/182888 A1 | 9/2019 | |
| WO | WO 2019/182896 A1 | 9/2019 | |
| WO | WO-2019182867 A1 * | 9/2019 | ......... G01N 33/6872 |

OTHER PUBLICATIONS

Auerbach, R. et al., "Angiogenesis assays: Problems and pitfalls," *Cancer and Metastasis*, 19 (2000): 167-172.

Beans, C., "Targeting metastasis to halt cancer's spread," *PNAS*, 115.50 (2018): 12539-12543.

Bork. P., "Powers and Pitfalls in Sequence Analysis: The 70% Hurdle," *Genome Research*, 10 (2000): 398-400.

Boussiotis, "Molecular and Biochemical Aspects of the PD-1 Checkpoint Pathway," *N Engl J Med*, 375(18):1767-1778, 2016.

Bowie, J. U. et al., "Deciphering the Message in Protein Sequences: Tolerance to Amino Acid Substitutions," *Science*, 247 (1990): 1306-1310.

Boyerinas et al., "Antibody-Dependent Cellular Cytotoxicity Activity of a Novel Anti-PD-L1 Antibody Avelumab (MSB0010718C) on Human Tumor Cells," *Cancer Immunol. Res.*, 3(10):1148-1157, 2015.

Brahmer et al., "Phase I Study of Single-Agent Anti-Programmed Death-1 (MDX-1106) in Refractory Solid Tumors: Safety, Clinical Activity, Pharmacodynamics, and Immunologic Correlates," *J. Clin. Oncolo.*, 28:3167-3175, 2010.

Brahmer et al., "Safety and Activity of Anti-PD-L1 Antibody in Patients with Advanced Cancer," *N. Eng. J. Med*, 366:2455-2465, 2012.

Brown et al., "Blockade of programmed dealth-1 ligands on dendritic cells enhances T cell activation and cytokine production," *The Journal of Immunology*, 170(3):1257-1266, 2003.

Burgess, W. H. et al., "Possible Dissociation of the Heparin-binding and Mitogenic Activities of Heparin-binding (Acidic Fibroblast) Growth Factor-1 from Its Receptor-binding Activities by Site-directed Mutagenesis of a Single Lysine Residue," *The Journal of Cell Biology*, 111 (1990): 2129-2138.

Casset, F. et al., "A peptide mimetic of an anti-CD4 monoclonal antibody by rational design," *Biochemical and Biophysical Research Communications*, 307 (2003): 198-205.

Cheng et al., "Structure and interactions of the human programmed cell death 1 receptor," *J. Biol. Chem.*, 288(17):11771-11785, 2013.

Couillault, C. et al., "Dual-specific antibodies blocking both PD-L1 and PD-L2 engagement of PD-1 restore anti-tumor immunity," *J Immunother Cancer*, 9.2 (2021): abstract.

Extended European Search Report issued in European Application No. 19771183.1, mailed Nov. 25, 2021.

Gravanis, I. et al., "The changing world of cancer drug development: the regulatory bodies' perspective," *Chinese Clinical Oncology*, 3.2 (2014): 1-5.

Greenspan, N. S. et al., "Defining epitopes: It's not as easy as it seems," *Nature Biotechnology*, 17 (1999): 936-937.

Gura, T., "Systems for Identifying New Drugs Are Often Faulty," *Science*, 278 (1997): 1041-1042.

Hait, W., "Anticancer drug development: the grand challenges," *Nature Reviews, Drug Discovery*, 9 (2010): 253-254.

Heppner, G. H. et al., "Tumor heterogeneity: biological implications and therapeutic consequences," *Cancer Metastasis Reviews*, 2 (1983): 5-23.

Jain, R., "Barriers to Drug Delivery in Solid Tumors," *Scientific American*, (1994): 58-65.

Kolar, G., "Immunoglobulins and B Lymphocytes, Immunoglobulins: Structure and Function," *Fundamental Immunology, Chapter 3, 5th edition*, (2003): 109-147.

Latchman et al., "PD-L2 is a second ligand for PD-1 and inhibits T cell activation," *Nat. Immunol.*, 2(3):261-268, 2001.

Lazar, E. et al., "Transforming Growth Factor ex: Mutation of Aspartic Acid 47 and Leucine 48 Results in Different Biological Activities," *Molecular and Cellular Biology*, 8.3 (1988): 1247-1252.

Lee et al., "Magneto-nanosensor platform for probing low-affinity protein-protein interactions and identification of a low-affinity PD-L1/PD-L2 interaction," *Nat. Commun.*, 7: 12220, 2016.

MacCallum, R. M. et al., "Antibody-antigen Interactions: Contact Analysis and Binding Site Topography," *J Mol. Biol.*, 262 (1996): 732-745.

Office Action issued in U.S. Appl. No. 17/040,240, dated Nov. 7, 2023.

Office Action issued in Chinese Application No. 201980020951.6, mailed Nov. 2, 2022, and English translation thereof.

Office Action issued in Chinese Application No. 201980020951.6, mailed Jan. 18, 2023, and English translation thereof.

Office Action issued in Chinese Application No. 201980020951.6, mailed Jul. 1, 2023, and English translation thereof.

Office Action issued in Singapore Application No. 11202009258R, dated Jun. 29, 2022.

Office Action issued in Japanese Application No. 2020-550644, dated Jan. 30, 2023, and English translation thereof.

Office Action issued in Japanese Application No. 2020-550644, mailed Jun. 28, 2023, and English translation thereof.

Office Action issued in Japanese Application No. 2020-550644, mailed Nov. 27, 2023, and English translation thereof.

PCT International Search Report and Written Opinion issued in International Application No. PCT/US2019/022295, mailed Jul. 29, 2019.

PCT International Search Report and Written Opinion issued in International Patent Application No. PCT/US2023/065194, mailed Jun. 23, 2023.

Radhakrishnan et al., "Blockade of allergic airway inflammation following systemic treatment with a B7-dendritic cell (PD-L2) cross-linking human antibody," *The Journal of Immunology*, 173(2):1360-1365, 2004.

Radhakrishnan et al., "Naturally occurring human IgM antibody that binds B7-DC and potentiates T cell stimulation by dendritic cells," *The Journal of Immunology*, 170(4):1830-1838, 2003.

Sela-Culang, I. et al., "The structural basis of antibody-antigen recognition," *Frontiers in Immunology*, 4 (2013): 1-13.

Sporn, M. B. et al., "Chemoprevention of Cancer," *Carcinogenesis*, 21.3 (2000): 525-530.

(56)          References Cited

OTHER PUBLICATIONS

Sun et al., "Regulation and function of the PD-L1 checkpoint," *Immunity*, 48(3): 434-452, 2018.

Vajdos, F. F. et al., "Comprehensive Functional Maps of the Antigen-binding Site of an Anti-ErbB2 Antibody Obtained with Shotgun Scanning Mutagenesis," *J. Mol. Biol.*, 320 (2002): 415-428.

Yearley et al., "PD-L2 expression in human tumors: relevance to Anti-PD-1 therapy in cancer," *Clinical Cancer Research*, 23(12): 3158-3167, 2017.

\* cited by examiner

| IgG Index | ADI Name | Octet IgG Kd Human PD-L1-Fc (M) Avid Monovalent | Octet IgG Kd Human PD-L1-His (M) Monovalent | Octet IgG Kd Human PD-L2-Fc (M) Avid | Octet IgG Kd Human PD-L2-His (M) Monovalent | Octet IgG Kd Human INSR Biovendor (M) Monovalent | Octet IgG Kd Human INSR R&D (M) Monovalent | Biacore IgG Kd Human PD-L1-His (M) Monovalent | Biacore IgG Kd Human PD-L2-His (M) Monovalent |
|---|---|---|---|---|---|---|---|---|---|
| 1 | 38003-IgG1 | 1.26E-09 | 7.62E-09 | 6.01E-10 | 1.90E-09 | N.B. | N.B. | 3.76E-09 | 7.27E-10 |
| 2 | 38003-IgG1 | 1.27E-09 | 1.42E-08 | 3.77E-10 | 1.02E-09 | N.B. | N.B. | 8.04E-09 | 1.75E-10 |
| 3 | 38004-IgG1 | 1.22E-09 | 2.06E-08 | 5.97E-10 | 2.84E-09 | N.B. | N.B. | 3.77E-08 | 1.24E-09 |
| 4 | ADI.37404-IgG1 | 1.53E-09 | 8.23E-09 | 4.26E-10 | 1.60E-09 | N.B. | N.B. | 2.76E-09 | 5.06E-10 |
| 5 | ADI.36148 | N.B. | N.B. | N.B. | N.B. | N.B. | N.B. | N.D. | N.D. |

FIG. 1

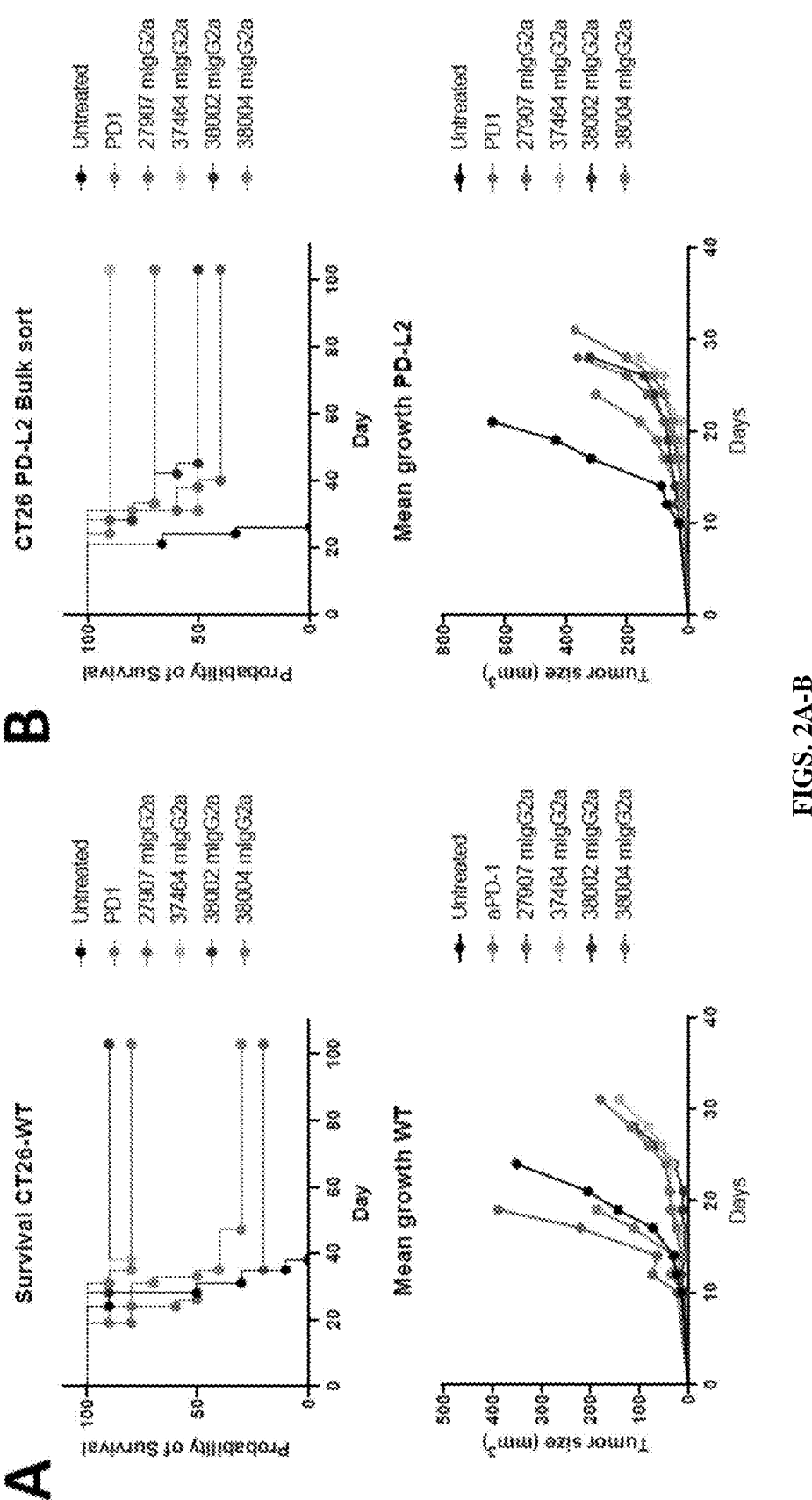
FIGS. 2A-B

Target are CHO cells expressing supra-physiologic densities of human Insulin Receptor (INSR). Detection is further amplified by use of a polyclonal secondard antibody

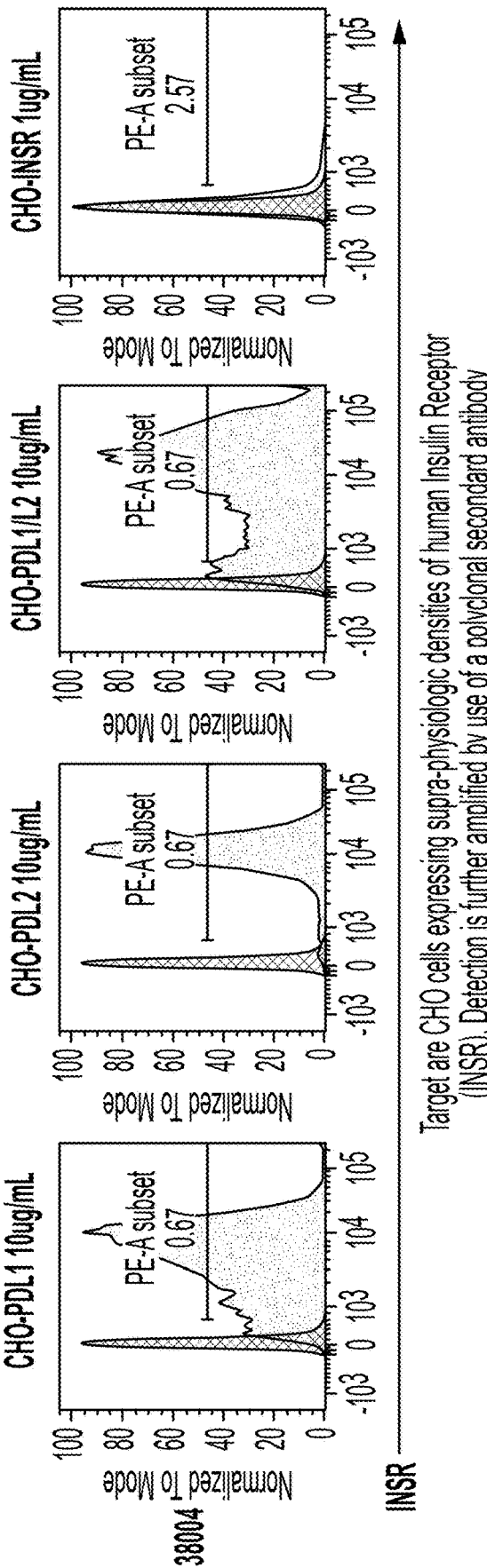
Target are CHO cells expressing supra-physiologic densities of human Insulin Receptor (INSR). Detection is further amplified by use of a polyclonal secondard antibody
FIG. 6-continued

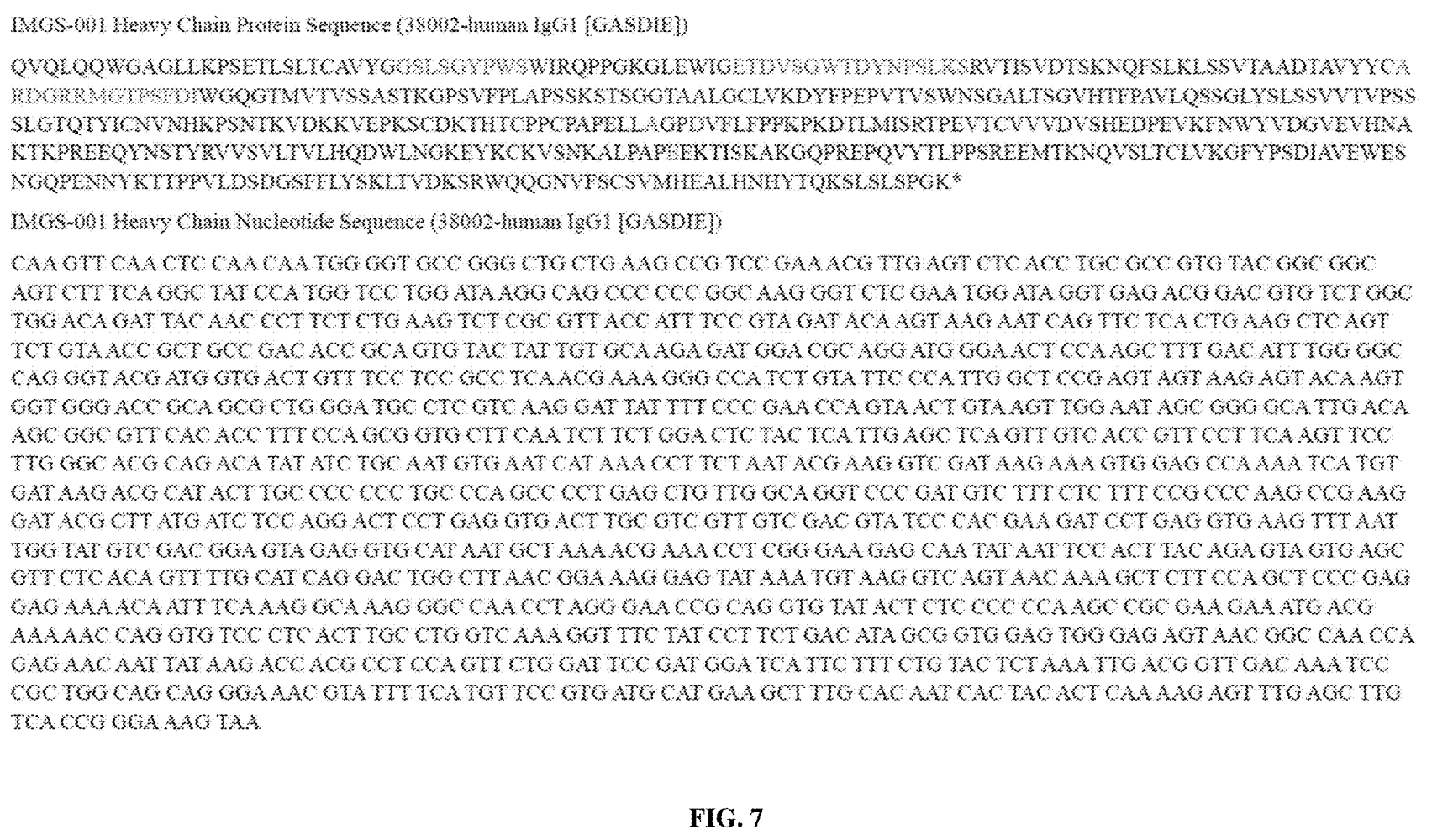

IMGS-001 Heavy Chain Protein Sequence (38002-human IgG1 [GASDIE])

QVQLQQWGAGLLKPSETLSLTCAVYGGSISSGGYYWSWIRQPPGKGLEWIGEIDHSGSTNYNPSLKSRVTISVDTSKNQFSLKLSSVTAADTAVYYCA
REGRMETPFFDIWGQGTMVTVSSASTKGPSVFPLAPSSKSTSGGTAALGCLVKDYFPEPVTVSWNSGALTSGVHTFPAVLQSSGLYSLSSVVTVPSS
SLGTQTYICNVNHKPSNTKVDKKVEPKSCDKTHTCPPCPAPELLGGPSVFLFPPKPKDTLMISRTPEVTCVVVDVSHEDPEVKFNWYVDGVEVHNA
KTKPREEQYNSTYRVVSVLTVLHQDWLNGKEYKCKVSNKALPAPIEKTISKAKGQPREPQVYTLPPSREEMTKNQVSLTCLVKGFYPSDIAVEWES
NGQPENNYKTTPPVLDSDGSFFLYSKLTVDKSRWQQGNVFSCSVMHEALHNHYTQKSLSLSPGK*

IMGS-001 Heavy Chain Nucleotide Sequence (38002-human IgG1 [GASDIE])

CAA GTT CAA CTC CAA CAA TGG GGT GCC GGG CTG CTG AAG CCG TCC GAA ACG TTG AGT CTC ACC TGC GCC GTC TAC GGC GGC
AGT CTT TCA GGC TAT CCA TGG TCC TGG ATA AGG CAG CCC CCG GGC AAG GGT CTC GAA TGG ATA GGT GAG ACG GAC GTG TCT GGC
TGG ACA GAT TAC AAC CCT TCT CTG AAG TCT CGC GTT ACC ATT TCC GTA GAT ACA AGT AAG AAT CAG TTC TCA CTG AAG CTC AGT
TCT GTA ACC GCT GCC GAC ACC GCA GTG TAC TAT TGT GCA AGA GAT GGA CGC AGG ATG GGA ACT CCA AGC TTT GAC ATT TGG GGC
CAG GGT ACG ATG GTG ACT GTT TCC TCC GCC TCA ACG AAA GGG CCA TCT GTA TTC CCA TTG GCT CCG AGT AGT AAG AGT ACA AGT
GGT GGG ACC GCA GCG GTG GGA TGC CTC GTC AAG GAT TAT TTT CCC GAA CCA GTA ACT GTA AGT TGG AAT AGC GGG GCA TTG ACA
AGC GGC GTT CAC ACC TTT CCA GCG GTG CTT CAA CTC TAC TCA TTG AGC TCA GTT GTC ACC GTT CCT TCA AGT TCC
TTG GGC ACG CAG ACA TAT ATC TGC AAT GTG AAT CAT AAA CCT TCT AAT ACG AAG GTC GAT AAG AAA GTG GAG CCA AAA TCA TGT
GAT AAG ACG CAT ACT TGC CCC CCG TGC CCA GCC CCT GAG CTG TTG GCA GGT CCC GAT GTC TTT CTC TTT CCG CCA AAG CCG AAG
GAT ACG CTT ATG ATC TCC AGG ACT CCT GAG GTG ACT TGC GTC GTT GTG GAC GTA TCC CAC GAA GAT CCT GAG GTG AAG TTT AAT
TGG TAT GTC GAC GGA GTA GAG GTG CAT CAG GAG AAA ACG AAA CCT CGG GAA GAG CAA TAT AAT TCC ACT TAC AGA GTA GTG AGC
GTT CTC ACA GTT TTG CAT CAG GAC TGG CTT AAC GGA AAG GAG TAT AAA TGT AAG GTC AGT CTT CCA GTT CTT CCA GAA GTA GTG ACC
GAG AAA ACA ATT TCA AAG GCA AAG GGC CAA CCT AGG GAA CCG CAG GTG TAT ACT CTC CCC CCA AGC CGC GAA GAA ATG ACG
AAA AAC CAG GTG TCC CTC ACT TGC CTG GTC AAA GGT TTC TAT CCT TCT GAC ATA GCG GTG GAG TGG AGT AAC GGC CAA CCA
GAG AAC AAT TAT AAG ACC ACG CCT CCA GTT CTG GAT TCC GAT GGA TCA TTC TTT CTG TAC TCT AAA TTG ACG GTT GAC AAT CC
CGC TGG CAG CAG GGA AAC GTA TTT TCA TGT TCC GTG ATG CAT GAA GCT TTG CAC AAT CAC TAC ACT CAA AAG AGT TTG AGC TTG
TCA CCG GGA AAG TAA

FIG. 7

IMGS-001 Kappa Light Chain Protein Sequence (38002-human IgG1 [GASDIE])

DIQMTQSPSSVSASVGDRVTITCRASQDINSFLAWYQQKPGKAPKLLIYAASSLQSGVPSRFSGSGSGTDFTLTISSLQPEDFATYYCQKSVYPPTFGGGTKV EIKRTVAAPSVFIFPPSDEQLKSGTASVVCLLNNFYPREAKVQWKVDNALQSGNSQESVTEQDSKDSTYSLSSTLTLSKADYEKHKVYACEVTHQGLSSPVT KSFNRGEC*

IMGS-001 Kappa Light Chain Nucleotide Sequence (38002-human IgG1 [GASDIE])

GAC ATT CAG ATG ACG CAA AGC CCC AGC TCT GTC TCA GCT TCC GTG GGT GAT AGG GTC ACT ATT ACA TGT CGA GCC TCA CAA GAT ATT AAT AGC TTT CTT GCA TGG TAT CAG CAA AAG CCA GGG AAG GCA CCT AAG CTC CTG ATT TAT GCT GCC TCT TCT TTG AAT AGC GGG GTC CCC TCC CGC TTC TCA GGA TCT GGG TCA GGG ACT GAC TTC ACG CTG ACT ATA TCC TCA CTC CAA CCA GAA GAT TTC GCC ACT TAT TAC TGC CAA AAA TCC GTA TAT TTC CCG CCC ACA TTC GGT GGG ACA AAA GTG GAA ATC AAG AGA ACT GTG GCT GCC CCA TCT GTT TTC ATC TTT CCA CCG AGC GAC GAA CAG CTC AAA AGC GGC ACT GCG AGT GTT GTT TGT CTG CTG AAT AAC TTC TAT CCC AGG GAA GCA AAG GTG CAG TGG AAG GTA GAC AAT GCT CTG CAA TCC GGG AAT AGT CAG GAG AGT GTC ACG GAG AAA CAC AAA GTT TAC GCT TGT GAA GTA ACG CAT CAG GGG TTG TCC AGT CCG GTT ACC AAA TCC TTC AAT CGG GGA GAG GAG TGT TGA

FIG. 8

G236A / S239D / I332E (human IgG1) heavy chain

FIG. 9

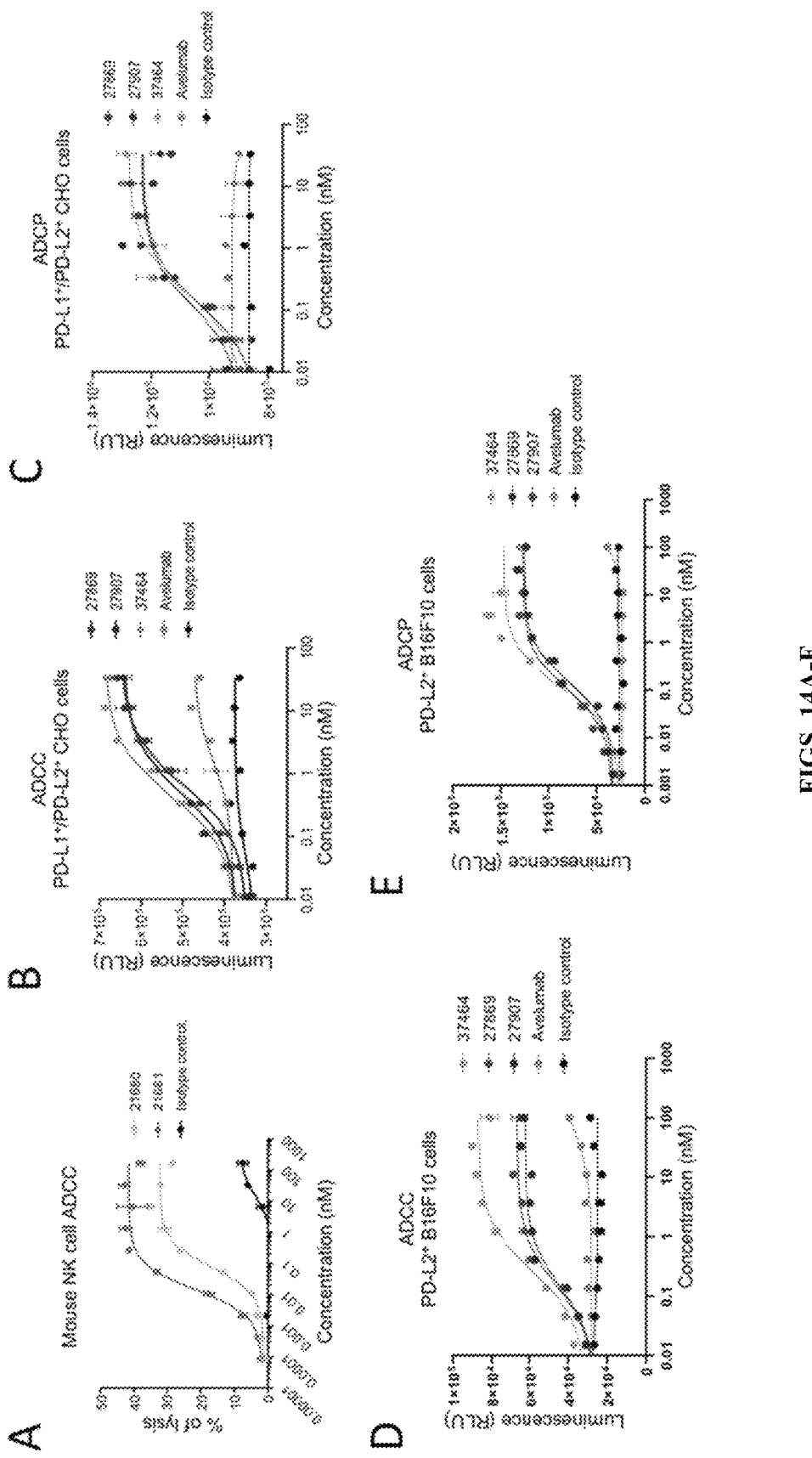
FIGS. 14A-E

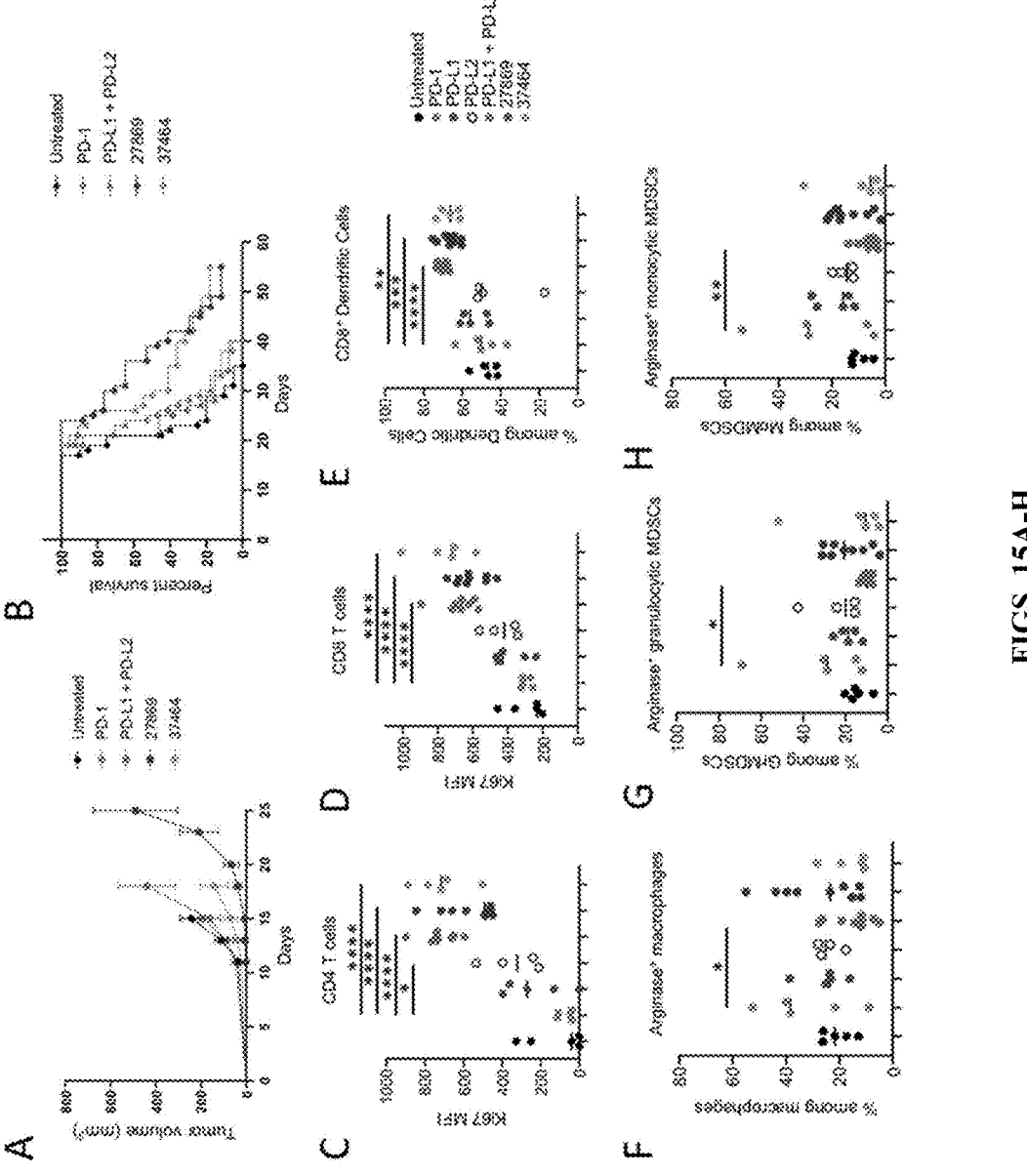
FIGS. 15A-H

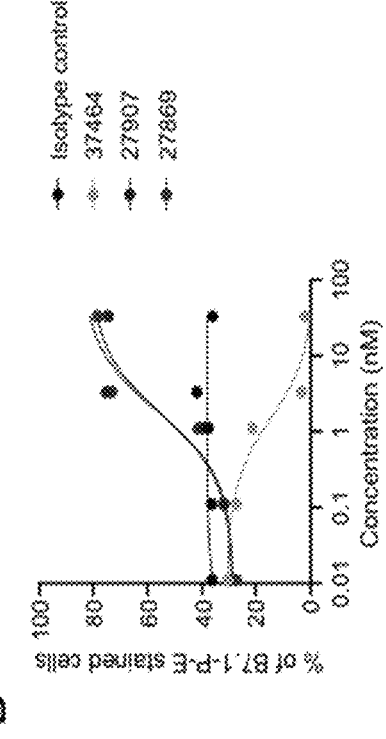
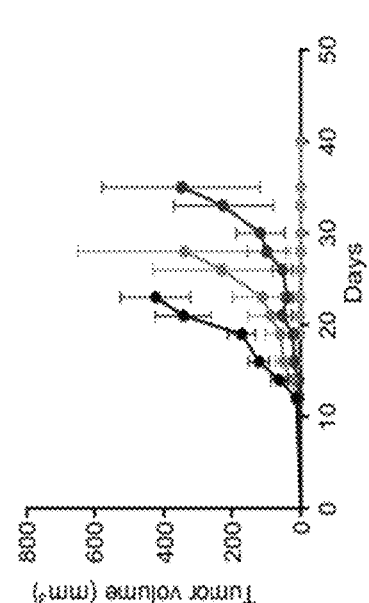
FIGS. 16A-B

Key to spotting pattern/ZsGreen1

| Position | Gene Id | Position | Gene Id | Position | Gene Id |
|---|---|---|---|---|---|
| 1 | FCGR1A | 17 | CD274 | 33 | IGHG2 |
| 2 | PDCD1LG2 | 18 | HTR2C | 34 | FCGR3A (single form) + FCER1G |
| 3 | INSR (Isoform Long) | 19 | FCGR2B (Isoform 5) | 35 | FCGR3A (single form) + CD247 |
| 4 | FCGR2B (Isoform IIB1) | 20 | UNC5D | 36 | INSR + IGF1R |
| 5 | INSR (Isoform Short) | 21 | FGF1 | 37 | IL12RB1 + IL12RB2 |
| 6 | CNGA3 | 22 | FGFBP2 | 38 | CD20 |
| 7 | CD44 | 23 | SAA2 | 39 | EGFR |
| 8 | SUSD6 | 24 | CXCL12 | | |
| 9 | SEMA4A | 25 | FCGR3A (single form)* | | |
| 10 | SLC38A4 | 26 | IGF2 | | |
| 11 | FCGR3A (single form) | 27 | FCGR3B (single form)* | | |
| 12 | FCGR3A (Undefined) | 28 | IGF1 | | |
| 13 | FCGR3B (single form) | 29 | FBLN1 | | |
| 14 | FCGR2A (Isoform 2) | 30 | PAPPA | | |
| 15 | IGHG3 | 31 | IGHG4 | | |
| 16 | FCGR2A (Isoform 1) | 32 | IGHG1 | | |

* Tethered secreted

FIG. 17A-continued

Key to spotting pattern/ZsGreen1

| Position | Gene Id |
|---|---|
| 1 | FCGR1A |
| 2 | PDCD1LG2 (PD-L2) |
| 3 | FCGR2B (Isoform IIB1) |
| 4 | INSR (Isoform Long) |
| 5 | PLXNC1 |
| 6 | INSR (Isoform short) |
| 7 | CD44 |
| 8 | PDGFRB |
| 9 | FCGR2A (Isoform 2) |
| 10 | FCGR3A (single form) |
| 11 | IGHG3 |
| 12 | MPZL2 |
| 13 | SLC22A23 |
| 14 | FCGR2A (Isoform 1) |
| 15 | PCDH8 |
| 16 | CD274 (PD-L1) |

| Position | Gene Id |
|---|---|
| 17 | FCGR2B (Isoform 5) |
| 18 | CST1 |
| 19 | IGFBP1 |
| 20 | ZG16B |
| 21 | CXCL12 |
| 22 | IGFBP3 |
| 23 | CST4 |
| 24 | IGF2 |
| 25 | FBLN1 |
| 26 | IGF1 |
| 27 | IGHG2 |
| 28 | IGHG1 |
| 29 | IGHG4 |
| 30 | PAPPA |
| 31 | FCGR3A + CD247 |
| 32 | FCGR3A + FCER1G |

| Position | Gene Id |
|---|---|
| 33 | IGFBP4 |
| 34 | UNC5D |
| 35 | LDLR |
| 36 | LDLR (Isoform 1) |
| 37 | OXGR1 |
| 38 | CD20 |
| 39 | EGFR |
| 40 | INSR + IGF1R |

FIG. 17B-continued

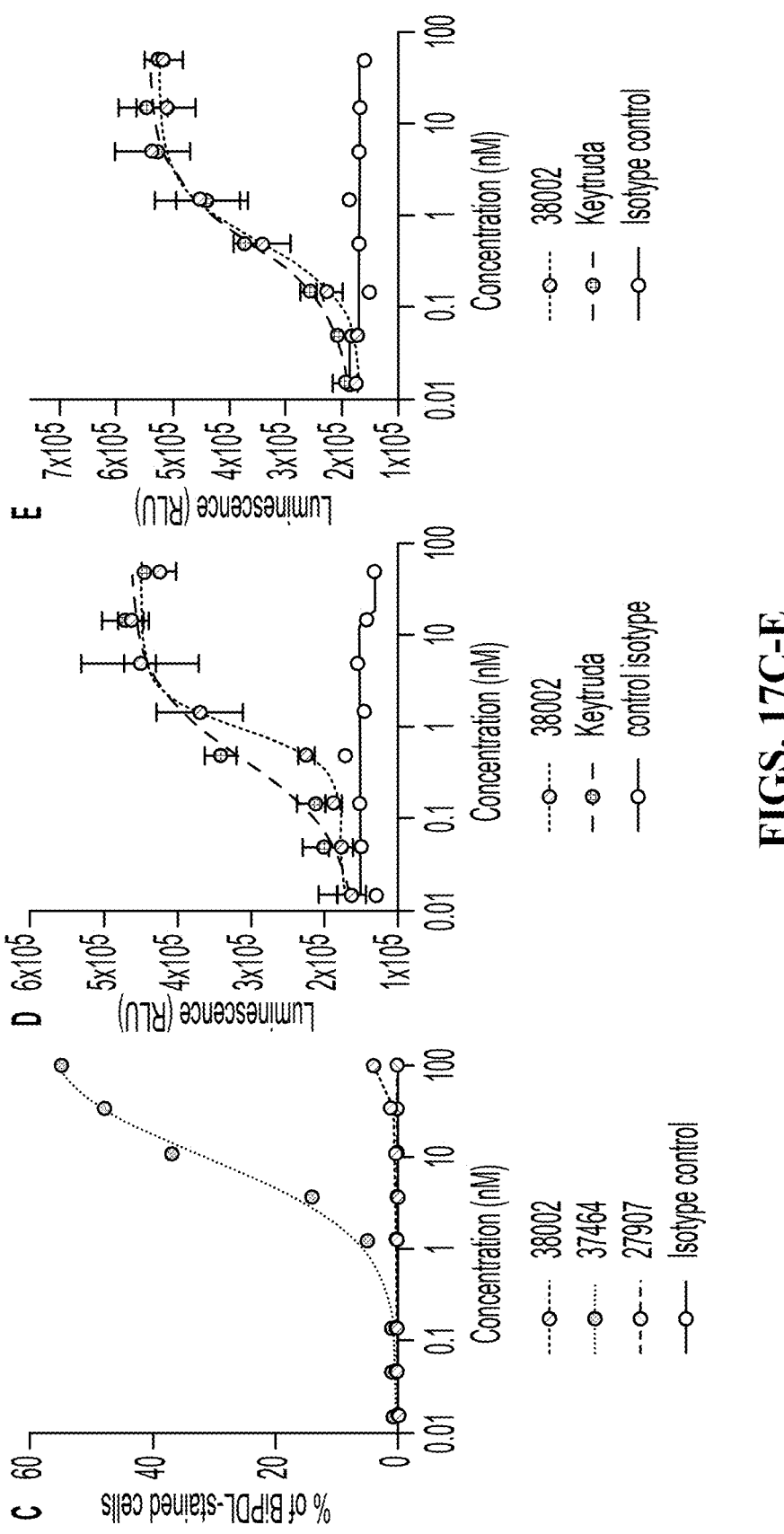
FIGS. 17C-E

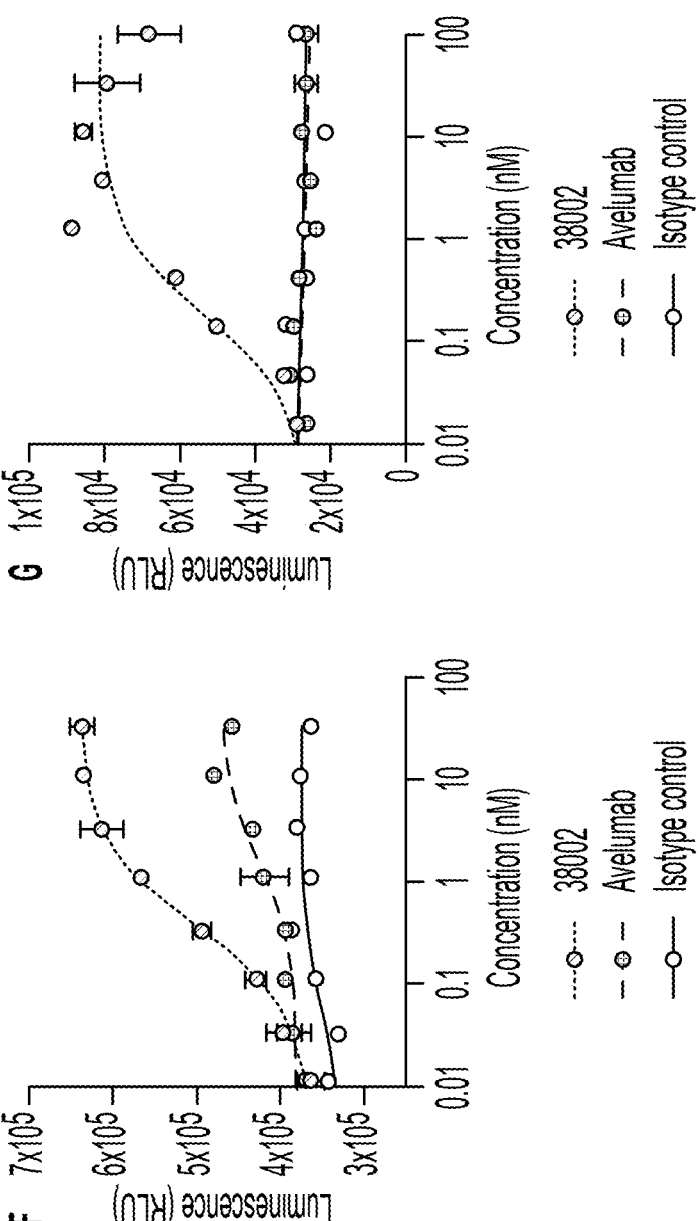
FIGS. 17F-G

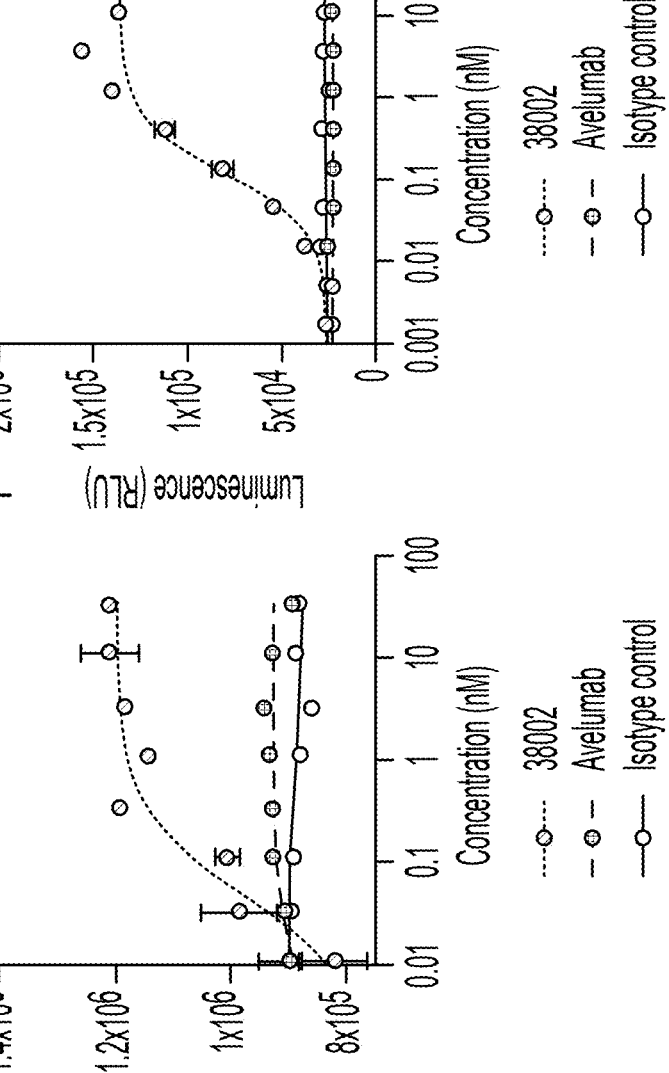
FIGS. 17H-I

A
| | hPD-L1 dimer | hPD-L2 dimer | hPD-L1 monomer | hPD-L2 monomer | mPD-L1 dimer | mPD-L2 dimer |
|---|---|---|---|---|---|---|
| 38002 | 1.28E-09 | 6.01E-10 | 7.62E-09 | 1.90E-09 | 3.20E-09 | 7.00E-10 |
B
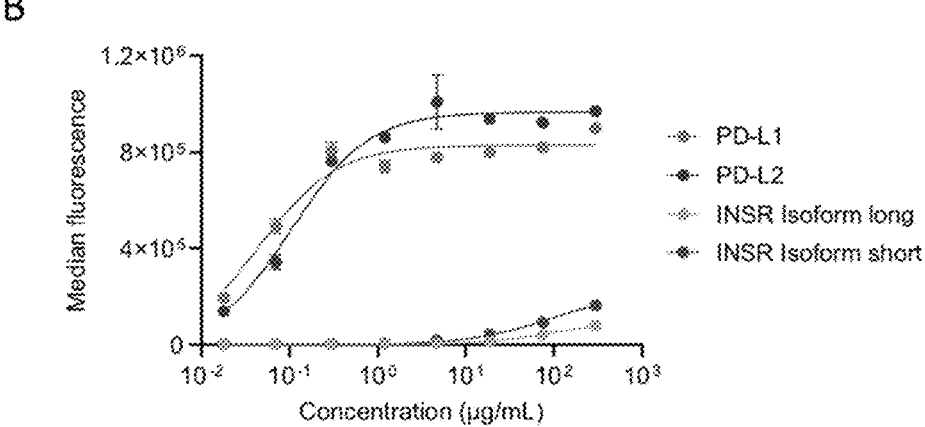
FIGS. 18A-B

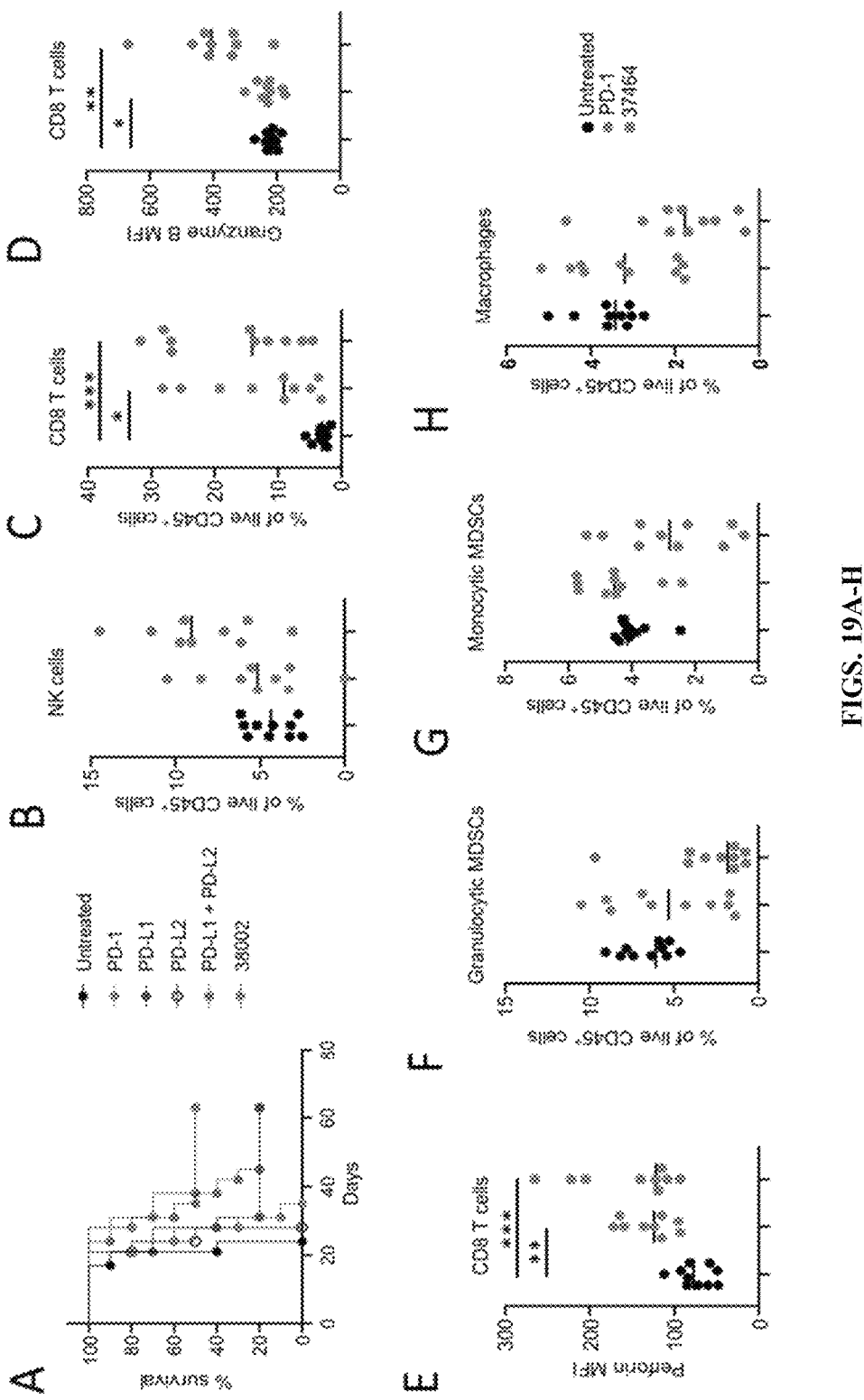
FIGS. 19A-H

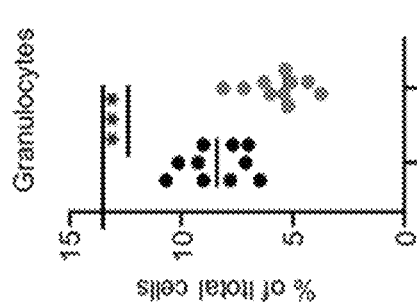
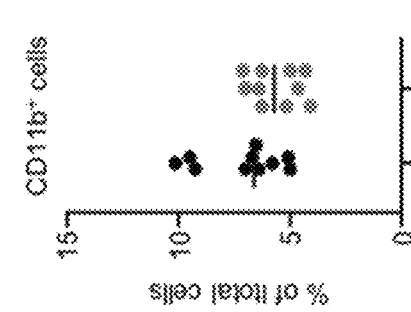
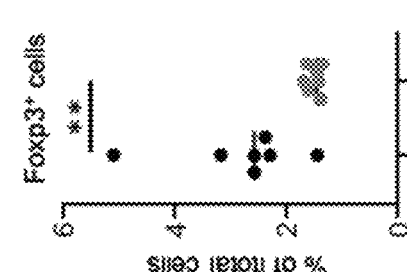
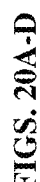
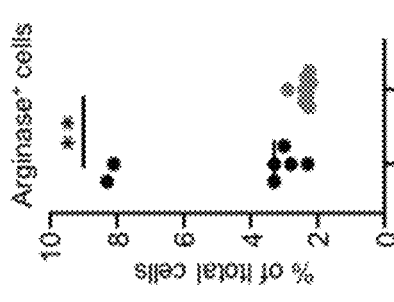
FIGS. 20A-D

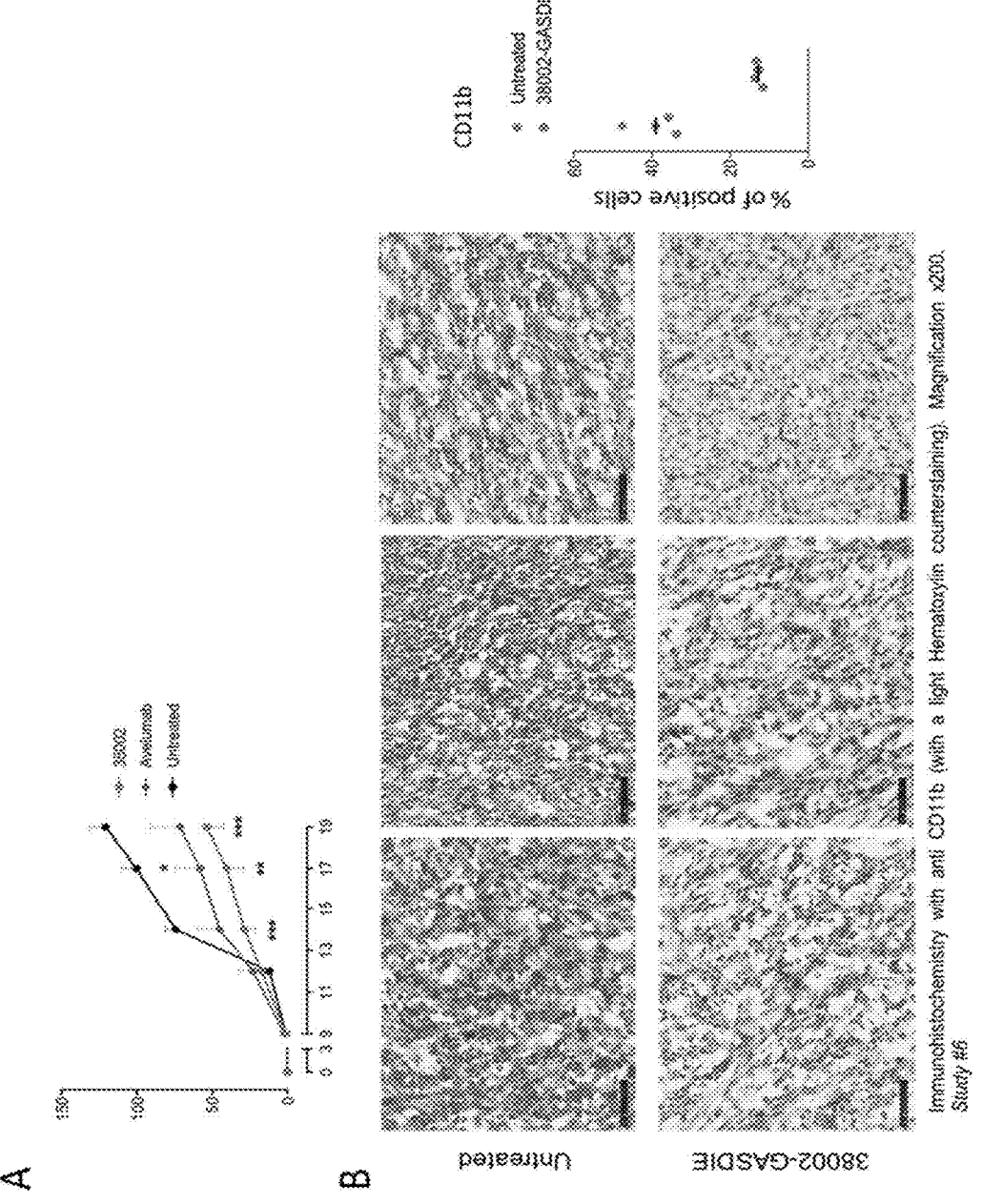
FIGS. 21A-B

Table 1

| | |
|---|---|
| 16415 | VH4-34, VK1-12 |

| |
|---|
| 20779 |

| |
|---|
| 21675 |

| |
|---|
| 21680 |

| |
|---|
| 37464 |

| |
|---|
| 37468 |

| | |
|---|---|
| 38002 | 38004 |

Close to Atezolizumab PD-L1 epitope
PD-L2 epitope similar to 24F.10C12

DUAL SPECIFICITY ANTIBODIES TO HUMAN PD-L1 AND PD-L2 AND METHODS OF USE THEREFOR

PRIORITY CLAIM

This application claims benefit of priority to U.S. Provisional Application Nos. 63/326,456, filed Apr. 1, 2022, and 63/378,196, filed Oct. 3, 2022, the entire contents of both applications being hereby incorporated by reference.

REFERENCE TO A SEQUENCE LISTING

This application contains a Sequence Listing XML, which has been submitted electronically and is hereby incorporated by reference in its entirety. Said Sequence Listing XML, created on Mar. 27, 2023, is named UTSCP1514US.xml and is 29,831 bytes in size.

FIELD

The present disclosure relates generally to the field of medicine, oncology, and immunology. More particularly, it concerns human dual antibodies with high affinity for PD-L1 and PD-L2 and their use in cancer therapies.

BACKGROUND

Blockade of T cell co-inhibitory receptor PD-1 interaction with its ligand PD-L1 has become a pillar of modern oncology, which is now available even in the first line setting for subsets of melanoma and lung cancer patients (Boussiotis, 2016). Numerous antibodies targeting PD-1 or PD-L1 are currently FDA approved or in clinical trials; however, no agents targeting the second PD-1 ligand, PD-L2, are under clinical investigation. PD-L2 binds PD-1 with an approximately 3-fold higher affinity than does PD-L1, and, like PD-L1, sends an inhibitory signal which attenuates T cell function (Cheng et al., 2013; Latchman et al., 2001; Lee et al., 2016; Li et al., 2017; Youngnak et al., 2003). Historically, PD-L2 was considered to be largely an inducible co-inhibitory molecule with expression limited to the tumor stroma; however, improved detection reagents for PD-L2 have revealed widespread PD-L2 expression both in the tumor microenvironment and on tumor cells themselves (Baptista et al., 2016; Danilova et al., 2016; Derks et al., 2015; Dong et al., 2016; Howitt et al., 2016; Kim et al., 2015; Kim et al., 2015; Nomi et al., 2007; Obeid et al., 2016; Ohigashi et al., 2005; Roemer et al., 2016; Shi et al., 2014; Shin et al., 2015; Xu et al., 2016). Recently, PD-L2 was shown to be an independent predictor of response to the PD-1 antibody pembrolizumab across multiple cancers (Yearley et al., 2017).

First described in the vast majority of classical Hodgkin's Lymphoma (cHL), amplification of chromosomal region 9p24.1 leads to direct upregulation of PD-L1 and PD-L2 (which reside therein), as well as indirect induction via enhanced JAK2 activity (Roemer et al., 2016; Shi et al., 2014; Green et al., 2010; Van Roosbroeck et al., 2016). In addition to cHL, this genetic driver of high PD-L1/PD-L2 co-expression is also found in the majority of Primary Mediastinal Large B-Cell Lymphoma (PMBL), T cell lymphoma, and a variety of histiocytic and dendritic cell malignancies. Not surprisingly, many of these cancers have been shown to respond to PD-1 blockade. More recently, 9p24.1 amplification has been demonstrated in solid tumors such as triple-negative breast cancer (TNBC) (Howitt et al., 2016; Barrett et al., 2015). Relatively high co-expression of PD-L1 and PDL2 has also been observed in a number of other cancers such as gastric carcinoma, melanoma, squamous carcinomas of the lung, head and neck, cervix and vulva, bladder cancer, and hepatocellular carcinoma among others (Baptista et al., 2016; Danilova et al., 2016; Derks et al., 2015; Dong et al., 2016; Howitt et al., 2016; Kim et al., 2015; Nomi et al., 2007; Obeid et al., 2016; Xu et al., 2016; Yearley et al., 2017; Van Roosbroeck et al., 2016; Barrett et al., 2015; Shin et al., 2016; Inoue et al., 2016; Wang et al., 2011). In addition to expression by these tumors themselves, stromal and endothelial expression of PD-L2 has also been documented for many of these tumors (Yearley et al., 2017). These findings suggest limitations to the therapeutic potential of PD-L1 blockade in these cancers.

The PD-1 co-inhibitory receptor is expressed primarily by activated T cells and NK cells and can be targeted by antibodies which bind it and prevent engagement by PD-ligands. PD-L1, in contrast, is expressed by tumor cells and suppressive stromal populations and can be targeted with antibodies capable of cytotoxic effector function. While the theoretical advantages of these antibody-dependent cellular cytotoxicity (ADCC) capable PD-L1 antibodies can be demonstrated in vitro, no patient data exists demonstrating actual effector function in patients or improved outcome relative to purely blocking variants (Boyerinas et al., 2015).

PD-L1 and PD-L2 share only approximately 40% identity, as each binds an additional receptor distinct from PD-1 (Latchman et al., 2001). PD-L1 also binds B7-1 in an additional negative T cell regulatory interaction (Butte et al., 2007; Butte et al., 2008). In mice, PD-L2 can bind to RGMb on either myeloid cells or T cells and regulate tolerance to inhaled antigens (Xiao et al., 2014; Nie et al., 2017). The role of PD-L2 binding to RGMb in tumors remains to be described, as does the relevance of this interaction in humans. It could prove extremely advantageous from a therapeutic standpoint to have bispecific antibodies to PD-L1 and PD-L2.

SUMMARY

The present disclosure is directed to the inventor's surprising discovery of a highly specific, dual specific antibody that selectively binds to both PD-L1 and LD-L2 while also exhibiting little to no off-target binding. As illustrated in FIG. 22, the inventors have developed a series of PD-L1/PD-L2 dual binding antibodies starting with ADI-16415. ADI-16415 underwent multiple rounds of affinity maturation to obtain ADI-37464, which exhibited high selectivity to PD-L1 and PD-L2, but also exhibited off-target binding to insulin-like growth factor 1 (IGF-1) receptor, which is a transmembrane receptor that belongs to the large class of tyrosine kinase receptors. The inventor continued to modify Ab-37464 to identify a novel antibody that maintained selective binding to both PD-L1 and LD-L2 that also avoided the off-target binding exhibited by ADI-37464. The inventors engineered the ADI-38000 series of antibodies (e.g., Ab-38000-Ab-38004), which are derivatives of 37464 with light chain CDR mutations designed to avoid off-target insulin receptor binding.

TABLE 1

| | | | |
|---|---|---|---|
| | | 16415 | VH4-34, VK1-12 |
| | | 20779 | |
| | | 21675 | |
| | | 21680 | |
| | 37464 | | 37468 |
| 38002 | 38004 | | |

Close to Atezolizumab PD-L1 epitope
PD-L2 epitope similar to 24F.10C12

Table 2 below summarizes the variations in light chain CDR sequences for the Ab-38000 series of antibodies as well as characteristic off target insulin receptor binding and PD-L1 and PD-L2 affinity.

TABLE 2

| Ab Name | VL CDR1 | VL CDR2 | VL CDR3 | Insulin Receptor Binding | PD-L1 Affinity | PD-L2 Affinity |
|---|---|---|---|---|---|---|
| ADI-37464 (original lead) | RASQGINSFLA (SEQ ID NO: 13) | AASSLNS (SEQ ID NO: 11) | QKAVYFPPT (SEQ ID NO: 15) | High | High | High |
| ADI-38000 | RASQGINSFLA (SEQ ID NO: 13) | AADSIQS (SEQ ID NO: 14) | QKAVYFPPT (SEQ ID NO: 15) | High | High | High |
| ADI-38001 | RASQGINSFLA (SEQ ID NO: 13) | AADSIQS (SEQ ID NO: 14) | QKSVYFPPT (SEQ ID NO: 12) | High | High | High |
| ADI-38002 | RASQDINSFLA (SEQ ID NO: 10) | AASSLNS (SEQ ID NO: 11) | QKSVYFPPT (SEQ ID NO: 12) | Very Low | High | High |
| ADI-38003 | RASKGISSFLA (SEQ ID NO: 16) | AASSLNS (SEQ ID NO: 11) | QKAVYFPPT (SEQ ID NO: 15) | Low | High | High |
| ADI-38004 | RASQGISSFLA (SEQ ID NO: 17) | AASSLOS (SEQ ID NO:14) | QSAVYFPPT (SEQ ID NO: 19) | Neg. | Med | Med |

Accordingly, the disclosure is based on the surprising and unexpected identification of ADI-38002, a dual specific antibody that exhibits high affinity to both PD-L1 and LD-L2 while also demonstrating little to no off-target binding. The inventors were particularly surprised that the engineered modification distinguishing ADI-37464 and ADI-38002, was based on a single non-conservative amino acid point mutation (e.g., substitution of a glycine in ADI-37464 for aspartic acid in ADI-38002), which would normally be expected to disrupt binding and/or reduce binding affinity.

Thus, in accordance with the present disclosure, there is provided an antibody or antibody fragment that binds selectively to both PD-L1 and PD-L2 (dual specific antibody to PD-L1 and PD-L2 (DSPDL)) and (i) having heavy chain CDR sequences of CDR1 GSLSGYPWS (SEQ ID NO:7), CDR2 ETDVSGWTDYNPSLKS (SEQ ID NO:8), and CDR3 ARDGRRMGTPSFDI (SEQ ID NO:9) and light chain CDR sequences of CDR1 RASQDINSFLA (SEQ ID NO:10), CDR2 AASSLNS (SEQ ID NO:11), and CDR3 QKSVYFPPT (SEQ ID NO:12); (ii) having heavy chain CDR sequences of CDR1 GSLSGYPWS (SEQ ID NO:7), CDR2 ETDVSGWTDYNPSLKS (SEQ ID NO:8), and CDR3 ARDGRRMGTPSFDI (SEQ ID NO:9) and light chain CDR sequences of CDR1 RASQGINSFLA (SEQ ID NO:13), CDR2 AADSIQS (SEQ ID NO:14), and CDR3 QKAVYFPPT (SEQ ID NO:15); or (iii) having heavy chain CDR sequences of CDR1 GSLSGYPWS (SEQ ID NO:7), CDR2 ETDVSGWTDYNPSLKS (SEQ ID NO:8), and CDR3 ARDGRRMGTPSFDI (SEQ ID NO:9) and light chain CDR sequences of CDR1 RASQGINSFLA (SEQ ID NO:13), CDR2 AADSIQS (SEQ ID NO:14), and CDR3 QKSVYFPPT (SEQ ID NO:12); or (iv) having heavy chain CDR sequences of CDR1 GSLSGYPWS (SEQ ID NO:7), CDR2 ETDVSGWTDYNPSLKS (SEQ ID NO:8), and CDR3 ARDGRRMGTPSFDI (SEQ ID NO:9) and light chain CDR sequences of CDR1 RASKGISSFLA (SEQ ID NO:16), CDR2 AASSLNS (SEQ ID NO:11), and CDR3 QKAVYFPPT (SEQ ID NO:15); or (v) having heavy chain CDR sequences of CDR1 GSLSGYPWS (SEQ ID NO:7), CDR2 ETDVSGWTDYNPSLKS (SEQ ID NO:8), and CDR3 ARDGRRMGTPSFDI (SEQ ID NO:9) and light chain CDR sequences of CDR1 RASQGISSFLA (SEQ ID NO:17), CDR2 AASSLQS (SEQ ID NO:18), and CDR3 QSAVYFPPT (SEQ ID NO:19). The antibody or antibody fragment may be encoded by variable sequences having:

(a) a heavy chain nucleotide sequence having at least or about 70%, 80%, 90%, 95%, 96%, 97%, 98%, 99%, or 100% identity to (SEQ ID NO: 3)
CAAGTTCAACTCCAACAATGGGGTGCCGGGCTGCTGAAGCCGTCCGAAA

CGTTGAGTCTCACCTGCGCCGTGTACGGCGGCAGTCTTTCAGGCTATCC

ATGGTCCTGGATAAGGCAGCCCCCCGGCAAGGGTCTCGAATGGATAGGT

GAGACGGACGTGTCTGGCTGGACAGATTACAACCCTTCTCTGAAGTCTC

GCGTTACCATTTCCGTAGATACAAGTAAGAATCAGTTCTCACTGAAGCT

CAGTTCTGTAACCGCTGCCGACACCGCAGTGTACTATTGTGCAAGAGAT

GGACGCAGGATGGGAACTCCAAGCTTTGACATTTGGGGCCAGGGTACGA

TGGTGACTGTTTCCTCCGCCTCAACGAAAGGGCCATCTGTATTCCCATT

GGCTCCGAGTAGTAAGAGTACAAGTGGTGGGACCGCAGCGCTGGGATGC

CTCGTCAAGGATTATTTTCCCGAACCAGTAACTGTAAGTTGGAATAGCG

GGGCATTGACAAGCGGCGTTCACACCTTTCCAGCGGTGCTTCAATCTTC

TGGACTCTACTCATTGAGCTCAGTTGTCACCGTTCCTTCAAGTTCCTTG

GGCACGCAGACATATATCTGCAATGTGAATCATAAACCTTCTAATACGA

AGGTCGATAAGAAAGTGGAGCCAAAATCATGTGATAAGACGCATACTTG

CCCCCCCTGCCCAGCCCCTGAGCTGTTGGCAGGTCCCGATGTCTTTCTC

TTTCCGCCCAAGCCGAAGGATACGCTTATGATCTCCAGGACTCCTGAGG

TGACTTGCGTCGTTGTCGACGTATCCCACGAAGATCCTGAGGTGAAGTT

TAATTGGTATGTCGACGGAGTAGAGGTGCATAATGCTAAAACGAAACCT

CGGGAAGAGCAATATAATTCCACTTACAGAGTAGTGAGCGTTCTCACAG

TTTTGCATCAGGACTGGCTTAACGGAAAGGAGTATAAATGTAAGGTCAG

TAACAAAGCTCTTCCAGCTCCCGAGGAGAAAACAATTTCAAAGGCAAAG

GGCCAACCTAGGGAACCGCAGGTGTATACTCTCCCCCCCAAGCCGCGAAG

AAATGACGAAAAACCAGGTGTCCCTCACTTGCCTGGTCAAAGGTTTCTA

TCCTTCTGACATAGCGGTGGAGTGGGAGAGTAACGGCCAACCAGAGAAC

AATTATAAGACCACGCCTCCAGTTCTGGATTCCGATGGATCATTCTTTC

-continued

```
TGTACTCTAAATTGACGGTTGACAAATCCCGCTGGCAGCAGGGAAACGT

ATTTTCATGTTCCGTGATGCATGAAGCTTTGCACAATCACTACACTCAA

AAGAGTTTGAGCTTGTCACCGGGAAAGTAA,
``` and (b) a light chain nucleotide sequence having at least or about 70%, 80% 90%, 95%, 96%, 97%, 98%, 99%, or 100% identity to:

(SEQ ID NO: 5)
```
GACATTCAGATGACGCAAAGCCCCAGCTCTGTCTCAGCTTCCGTGGGTG

ATAGGGTGACTATTACATGTCGAGCCTCACAAGATATTAATAGCTTTCT

TGCATGGTATCAGCAAAAGCCAGGGAAGGCACCTAAGCTCCTGATTTAT

GCTGCCTCTTCTTTGAATAGCGGGGTCCCCTCCCGCTTCTCAGGATCTG

GGTCAGGGACTGACTTCACGCTGACTATATCCTCACTCCAACCAGAAGA

TTTCGCCACTTATTACTGCCAAAAATCCGTATATTTCCCGCCCACATTC

GGTGGTGGGACAAAAGTGGAAATCAAGAGAACTGTCGCTGCCCCATCTG

TTTTCATCTTTCCACCGAGCGACGAACAGCTCAAAAGCGGCACTGCGAG

TGTTGTTTGTCTGCTGAATAACTTCTATCCCAGGGAAGCAAAGGTGCAG

TGGAAGGTAGACAATGCTCTGCAATCCGGGAATAGTCAGGAATCCGTCA

CGGAGCAAGACAGTAAGGACTCCACGTATTCCTTGAGTAGTACATTGAC

CCTCAGTAAAGCGGATTACGAGAAACACAAAGTTTACGCTTGTGAAGTA

ACGCATCAGGGGTTGTCCAGTCCGGTTACCAAATCCTTCAATCGGGGAG

AGTGTTGA.
```

The antibody or antibody fragment may comprise a heavy chain with an amino acid sequence having at least or about 70%, 80% 90%, 95%, 96%, 97%, 98%, 99%, or 100% identity to:

(SEQ ID NO: 4)
```
QVQLQQWGAGLLKPSETLSLTCAVYGGSLSGYPWSWIRQPPGKGLEWIG

ETDVSGWTDYNPSLKSRVTISVDTSKNQFSLKLSSVTAADTAVYYCARD

GRRMGTPSFDIWGQGTMVTVSSASTKGPSVFPLAPSSKSTSGGTAALGC

LVKDYFPEPVTVSWNSGALTSGVHTFPAVLQSSGLYSLSSVVTVPSSSL

GTQTYICNVNHKPSNTKVDKKVEPKSCDKTHTCPPCPAPELLAGPDVFL

FPPKPKDTLMISRTPEVTCVVVDVSHEDPEVKFNWYVDGVEVHNAKTKP

REEQYNSTYRVVSVLTVLHQDWLNGKEYKCKVSNKALPAPEEKTISKAK

GQPREPQVYTLPPSREEMTKNQVSLTCLVKGFYPSDIAVEWESNGQPEN

NYKTTPPVLDSDGSFFLYSKLTVDKSRWQQGNVFSCSVMHEALHNHYTQ

KSLSLSPGK
``` and a light chain with an amino acid sequence having at least or about 70%, 80% 90%, 95%, 96%, 97%, 98%, 99%, or 100% identity to (SEQ ID NO: 6)
```
DIQMTQSPSSVSASVGDRVTITCRASQDINSFLAWYQQKPGKAPKLLIY

AASSLNSGVPSRFSGSGSGTDFTLTISSLQPEDFATYYCQKSVYFPPTF

GGGTKVEIKRTVAAPSVFIFPPPSDEQLKSGTASVVCLLNNFYPREAKVQ

WKVDNALQSGNSQESVTEQDSKDSTYSLSSTLTLSKADYEKHKVYACEV

THQGLSSPVTKSFNRGEC.
```

There is also provided a method of treating cancer in a subject comprising contacting a PD-L1-, PD-L2-, or PD-L1 and PDL2-positive cancer cell in a subject with an antibody as described above. The PD-L1-, PD-L2-, or PD-L1 and PDL2-positive cancer cell may be a solid tumor cell, such as a lung cancer cell, brain cancer cell, head and neck cancer cell, breast cancer cell, skin cancer cell, liver cancer cell, pancreatic cancer cell, stomach cancer cell, colon cancer cell, rectal cancer cell, uterine cancer cell, cervical cancer cell, ovarian cancer cell, testicular cancer cell, skin cancer cell, esophageal cancer cell, a lymphoma cell, a renal cell carcinoma cell, or may be a leukemia or myeloma such as acute myeloid leukemia, chronic myelogenous leukemia or multiple myeloma.

The method may further comprise contacting the PD-L1-, PD-L2-, or PD-L1 and PDL2-positive cancer cell with a second anti-cancer agent or treatment, such as chemotherapy, radiotherapy, immunotherapy, hormonal therapy, or toxin therapy. The second anti-cancer agent or treatment may inhibit an intracellular PD-L1 or PD-L2 function. The second anticancer agent or treatment may be given at the same time as the first agent or given before and/or after the agent. The PD-L1 or PD-L2-positive cancer cell may be a metastatic cancer cell, a multiply drug resistant cancer cell or a recurrent cancer cell.

The antibody fragment may be a recombinant scFv (single chain fragment variable) antibody, a single domain antibody, Fab fragment, F(ab')2 fragment, or Fv fragment. The antibody may be a chimeric antibody, a humanized antibody, or an IgG. The antibody may be a human antibody, murine antibody, an IgG, a humanized antibody or a humanized IgG. The antibody or antibody fragment may further comprise a label, such as a peptide tag, an enzyme, a magnetic particle, a chromophore, a fluorescent molecule, a chemiluminescent molecule, or a dye. The antibody or antibody fragment may further comprise an antitumor drug linked thereto, such as linked to the antibody or antibody fragment through a photolabile linker or an enzymatically-cleaved linker. The antitumor drug may be a toxin, a radioisotope, a cytokine or an enzyme. The antibody or antibody fragment may be conjugated to a nanoparticle or a liposome.

In another embodiment, there is provided a method of treating a cancer in a subject comprising delivering to the subject an antibody or antibody fragment having (i) heavy chain CDR sequences of CDR1 SEQ ID NO:7, CDR2 SEQ ID NO:8, and CDR3 SEQ ID NO:9; and light chain CDR sequences of CDR1 SEQ ID NO:10, CDR2 SEQ ID NO:11, and CDR3 SEQ ID NO:12; (ii) heavy chain CDR sequences of CDR1 SEQ ID NO:7, CDR2 SEQ ID NO:8, and CDR3 SEQ ID NO:9 and light chain CDR sequences of CDR1 SEQ ID NO:13, CDR2 SEQ ID NO:14, and CDR3 SEQ ID NO:15; or (iii) having heavy chain CDR sequences of CDR1 SEQ ID NO:7, CDR2 SEQ ID NO:8, and CDR3 SEQ ID NO:9, and light chain CDR sequences of CDR1 SEQ ID NO:13, CDR2 SEQ ID NO:14, and CDR3 SEQ ID NO:12; or (iv) having heavy chain CDR sequences of CDR1 SEQ ID NO:7, CDR2 SEQ ID NO:8, and CDR3 SEQ ID NO:9 and light chain CDR sequences of CDR1 SEQ ID NO:16, CDR2 SEQ ID NO:11, and CDR3 SEQ ID NO:15; or (v) having heavy chain CDR sequences of CDR1 SEQ ID NO:7, CDR2 SEQ ID NO:8, and CDR3 SEQ ID NO:9 and light chain CDR sequences of CDR1 SEQ ID NO:17, CDR2 SEQ ID NO:18, and CDR3 SEQ ID NO:19. The antibody fragment may be a recombinant scFv (single chain fragment variable) antibody, Fab fragment, F(ab'h fragment, or Fv fragment. The antibody may be an IgG. The antibody may be a chimeric antibody or a humanized antibody. Delivering may comprise antibody or antibody fragment administration, or genetic delivery with an RNA or DNA sequence or vector encoding the antibody or antibody fragment.

The antibody or antibody fragment may be encoded by light and heavy chain variable sequences as set forth in SEQ ID NO:3 and SEQ ID NO:5, or may be encoded by light and heavy chain variable sequences having at least or about 70%, 80%, 90%, 95%, 96%, 97%, 98%, 99%, or 100% identity to sequences from SEQ ID NO:3 and SEQ ID NO:5. The antibody or antibody fragment may comprise light and heavy chain variable sequences according to sequences from SEQ ID NO:4 and SEQ ID NO:6, may comprise light and heavy chain variable sequences having at least or about 70%, 80%, 90%, 95%, 96%, 97%, 98%, 99%, or 100% identity to sequences from SEQ ID NO:4 and SEQ ID NO:6, or may comprise light and heavy chain variable sequences having at least or about 95%, 96%, 97%, 98%, 99%, or 100% identity to sequences from SEQ ID NO:4 and SEQ ID NO:6.

Also provided is a monoclonal antibody, wherein the antibody or antibody fragment is characterized by (i) heavy chain CDR sequences SEQ ID NO:7, SEQ ID NO:8, and SEQ ID NO:9 and light chain CDR sequences SEQ ID NO:10, SEQ ID NO:11, and SEQ ID NO:12; (ii) heavy chain CDR sequences of CDR1 SEQ ID NO:7, CDR2 SEQ ID NO:8, and CDR3 SEQ ID NO:9 and light chain CDR sequences of CDR1 SEQ ID NO:13, CDR2 SEQ ID NO:14, and CDR3 SEQ ID NO:15; or (iii) having heavy chain CDR sequences of CDR1 SEQ ID NO:7, CDR2 SEQ ID NO:8, and CDR3 SEQ ID NO:9, and light chain CDR sequences of CDR1 SEQ ID NO:13, CDR2 SEQ ID NO:14, and CDR3 SEQ ID NO:12; or (iv) having heavy chain CDR sequences of CDR1 SEQ ID NO:7, CDR2 SEQ ID NO:8, and CDR3 SEQ ID NO:9 and light chain CDR sequences of CDR1 SEQ ID NO:16, CDR2 SEQ ID NO:11, and CDR3 SEQ ID NO:15; or (v) having heavy chain CDR sequences of CDR1 SEQ ID NO:7, CDR2 SEQ ID NO:8, and CDR3 SEQ ID NO:9 and light chain CDR sequences of CDR1 SEQ ID NO:17, CDR2 SEQ ID NO:18, and CDR3 SEQ ID NO:19. The antibody fragment may be a recombinant scFv (single chain fragment variable) antibody, Fab fragment, F(ab')2 fragment, or Fv fragment. The antibody may be a chimeric antibody, a humanized antibody, or an IgG.

Also provided is a nucleic acid encoding the antibody or antibody fragment having light and heavy chain variable sequences as set forth SEQ ID NO:3 and SEQ ID NO:5, or a nucleic acid encoding light and heavy chain variable sequences having at least or about 70%, 80%, 90%, 95%, 96%, 97%, 98%, 99%, or 100% identity to sequences from SEQ ID NO:3 and SEQ ID NO:5. Also provided is a nucleic acid encoding the antibody or antibody fragment having light and heavy chain variable sequences according to sequences from SEQ ID NO:4 and SEQ ID NO:6, or a nucleic acid encoding an antibody or an antibody fragment comprising light and heavy chain variable sequences having at least or about 70%, 80%, 90%, 95%, 96%, 97%, 98%, 99%, or 100% identity to sequences from SEQ ID NO:4 and SEQ ID NO:6.

In yet another embodiment, there is provided a hybridoma or engineered cell expressing an antibody or antibody fragment wherein the antibody or antibody fragment is characterized by heavy chain CDR sequences SEQ ID NO:7, SEQ ID NO:8, and SEQ ID NO:9 and light chain CDR sequences SEQ ID NO:10, SEQ ID NO:11, and SEQ ID NO:12; (ii) heavy chain CDR sequences of CDR1 SEQ ID NO:7, CDR2 SEQ ID NO:8, and CDR3 SEQ ID NO:9 and light chain CDR sequences of CDR1 SEQ ID NO:13, CDR2 SEQ ID NO:14, and CDR3 SEQ ID NO:15; or (iii) having heavy chain CDR sequences of CDR1 SEQ ID NO:7, CDR2 SEQ ID NO:8, and CDR3 SEQ ID NO:9, and light chain CDR sequences of CDR1 SEQ ID NO:13, CDR2 SEQ ID NO:14, and CDR3 SEQ ID NO:12; or (iv) having heavy chain CDR sequences of CDR1 SEQ ID NO:7, CDR2 SEQ ID NO:8, and CDR3 SEQ ID NO:9 and light chain CDR sequences of CDR1 SEQ ID NO:16, CDR2 SEQ ID NO:11, and CDR3 SEQ ID NO:15; or (v) having heavy chain CDR sequences of CDR1 SEQ ID NO:7, CDR2 SEQ ID NO:8, and CDR3 SEQ ID NO:9 and light chain CDR sequences of CDR1 SEQ ID NO:17, CDR2 SEQ ID NO:18, and CDR3 SEQ ID NO:19. The antibody fragment may be a recombinant scFv (single chain fragment variable) antibody, a single domain antibody, Fab fragment, F(ab')2 fragment, or Fv fragment. The antibody may be a chimeric antibody, a humanized antibody, or an IgG.

A further embodiment comprises a cancer vaccine comprising one or more antibodies or antibody fragments characterized by heavy and light chain CDR sequences as described above. At least one antibody fragment may be a recombinant scFv (single chain fragment variable) antibody, a single domain antibody, Fab fragment, F(ab')2 fragment, or Fv fragment. At least one of antibody may be a chimeric antibody, or an IgG. At least one antibody or antibody fragment may be encoded by light and heavy chain variable sequences as set forth herein, may be encoded by light and heavy chain variable sequences as described above, and may be encoded by light and heavy chain variable sequences having at least or about 70%, 80%, 90%, 95%, 96%, 97%, 98% or 99% identity to sequences as described above. At least one antibody or antibody fragment may comprise light and heavy chain variable sequences according to sequences as described above and may comprise light and heavy chain variable sequences having at least or about 70%, 80%, 90%, 95%, 96%, 97%, 98% or 99% identity to sequences as described above.

In another embodiment there is provided a method of detecting PD-L1 or PD-L2 expressing cells in a subject comprising contacting a sample from said subject with an antibody or antibody fragment characterized by heavy and light chain CDR sequences as described above and detecting a PD-L1 or PD-L2 expressing cell in said sample by binding said antibody or antibody fragment to a cell in said sample. The sample may be a body fluid or a tissue sample. The cell may be a cancer cell, such as a lymphoma cell, breast cancer cell, or renal cell carcinoma cell. The cell may be a cell associated with immune suppression. The cell associated with immune suppression may be a non-cancerous cell in a tumor microenvironment, such as a stromal cell or endothelial cell. Detection may comprise ELISA, RIA, or Western blot. The method may further comprise performing the method a second time and determining a change in antigen levels as compared to the first assay. The antibody or antibody fragment may be encoded by light and heavy chain variable sequences as described above and may be encoded by light and heavy chain variable sequences having at least or about 70%, 80%, 90%, 95%, 96%, 97%, 98% or 99% identity to sequences as described above. The antibody or antibody fragment may comprise light and heavy chain variable sequences according to sequences described above and may comprise light and heavy chain variable sequences having at least or about 70%, 80%, 90%, 95%, 96%, 97%, 98% or 99% identity to sequences described above.

It is contemplated that any method or composition described herein can be implemented with respect to any other method or composition described herein. Other objects, features and advantages of the present disclosure will become apparent from the following detailed description. It should be understood, however, that the detailed description and the specific examples, while indicating specific embodiments of the disclosure, are given by way of illustration only, since various changes and modifications within the spirit and scope of the disclosure will become apparent to those skilled in the art from this detailed description.

As used herein, "essentially free," in terms of a specified component, is used herein to mean that none of the specified component has been purposefully formulated into a composition and/or is present only as a contaminant or in trace amounts. The total amount of the specified component resulting from any unintended contamination of a composition is preferably below 0.01%. Most preferred is a composition in which no amount of the specified component can be detected with standard analytical methods.

As used herein in the specification and claims, "a" or "an" may mean one or more. As used herein in the specification and claims, when used in conjunction with the word "comprising", the words "a" or "an" may mean one or more than one. As used herein, in the specification and claim, "another" or "a further" may mean at least a second or more.

As used herein in the specification and claims, the term "about" is used to indicate that a value includes the inherent variation of error for the device, the method being employed to determine the value, or the variation that exists among study subjects.

Other objects, features and advantages of the present invention will become apparent from the following detailed description. It should be understood, however, that the detailed description and the specific examples, while indicating certain embodiments of the invention, are given by way of illustration only, since various changes and modifications within the spirit and scope of the invention will become apparent to those skilled in the art from this detailed description.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

FIG. 1 illustrates 38000 series affinity measurements by Octet. Affinity for each of the low/no Insulin Receptor binding members of the 38000 series was measured by Octet for PD-L1 and PD-L2 of the species indication. Human monovalent PD-L1 and PD-L2 affinities were also measured by Biacore.

FIGS. 2A-B illustrates treatment of CT26 parental and CT26-PD-L2 tumors with 38000 series PD-L1/PD-L2 dual-specific antibodies. FIG. 2A illustrates parental CT26 tumors were implanted in BALB/C mice and treated on days 3, 6, and 9 with 10 mg/kg of the indicated antibody. FIG. 2B illustrates CT26-PDL2 tumors were implanted in BALB/C mice and treated on days 3, 6, and 9 with 10 mg/kg of the indicated antibody. Tumor sizes were caliper measured with 1000 mm$^3$ as an endpoint.

FIG. 7 illustrates ADI-38002 Complete Heavy Chain Variable Region Sequence. (SEQ ID NOS: 20 and 21).

FIG. 8 illustrates ADI-38002 Complete Light Chain Variable Region Sequence. (SEQ ID NOS: 22 and 23).

Figure 9:
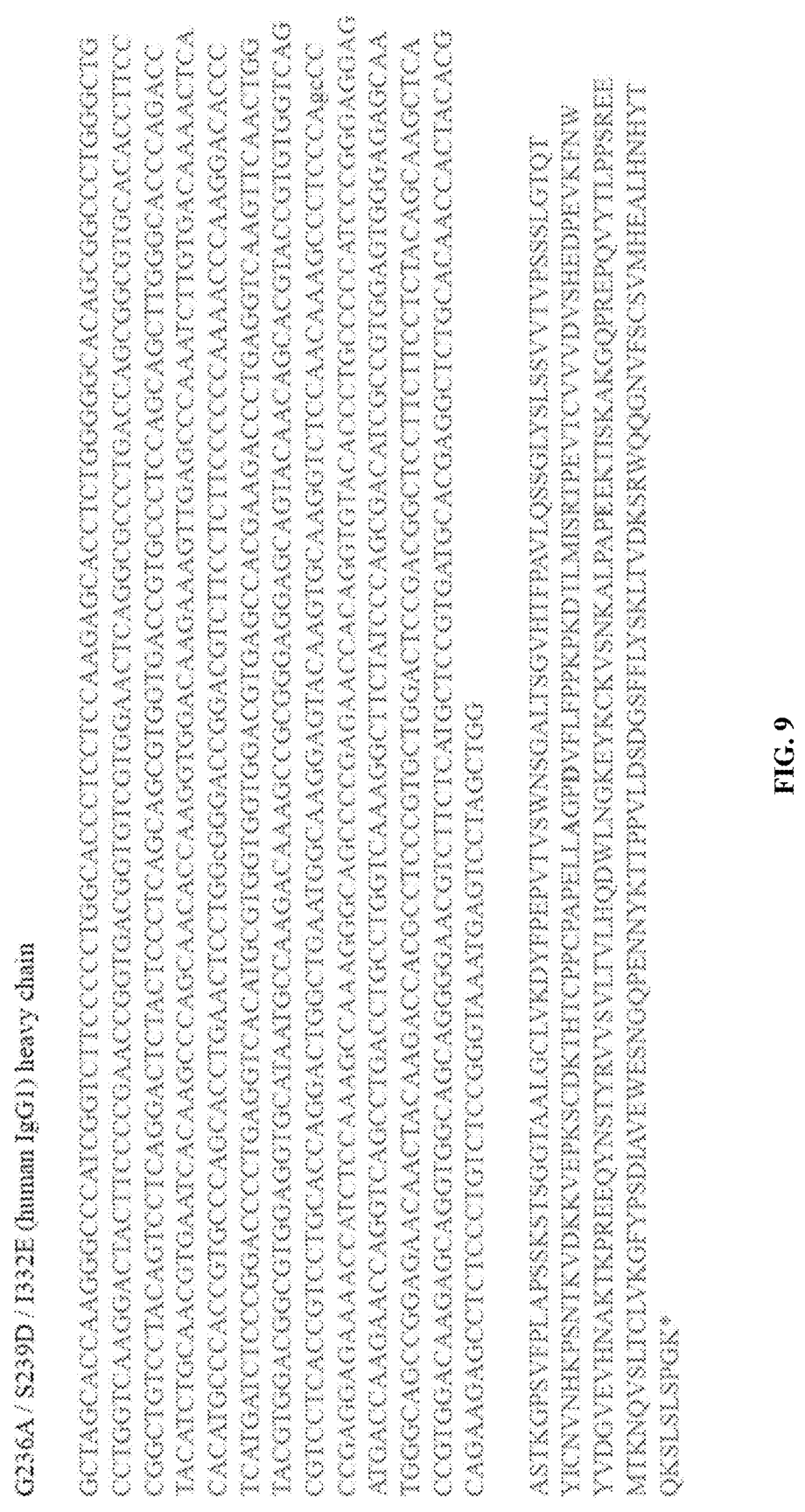

FIG. 9 illustrates ADI-38002 Human IgG1 (GASDIE) Constant Region Sequence. (SEQ ID NOS: 24 and 25).

FIGS. 14A-E show selected dual specific antibodies are able to engage Fcy receptors and induce NK cell antibody-dependent cell cytotoxicity. (FIG. 14A) U2940 target cells labeled with calcein were incubated with the indicated mouse IgG2a dual specific antibodies and co-cultured with NK cells isolated from mouse spleens. The percentage of cell lysis was measured using calcein release of samples and controls. Mean±SEM (n=2) is displayed for each concentration of each antibody. (FIGS. 14B-C) Chinese hamster ovary (CHO) PD-L1$^+$ CHO cells and PD-L2$^+$ CHO cells (1:1 mixture of the two cell lines) were incubated with dual-specific antibodies at concentrations displayed on the x-axis and co-cultured with NFAT-RE luciferase reporter Jurkat T cells (FcgRIIIa for ADCC or FcgRIIa-H for ADCP). A higher signal indicates an efficient ADCC (FIG. 14B) or ADCP (FIG. 14C) activation pathway. Mean±SEM (n=3) is displayed for each concentration of each antibody. (FIGS. 14D-E) Murine melanoma cancer cells B16F10 ectopically expressing PD-L2 were incubated with dual-specific antibodies at concentrations displayed on the x-axis and co-cultured with NFAT-RE luciferase reporter Jurkat T cells (FcgRIIIa for ADCC or FcgRIIa-H for ADCP). A higher signal indicates an efficient ADCC (FIG. 14D) or ADCP (FIG. 14E) activation pathway. Mean±SEM (n=3) is displayed for each concentration of each antibody. Nonlinear regression was used to generate best-fit curves in GraphPad Prism.

FIGS. 15A-H show selected dual-specific antibodies delay tumor growth and increase survival in B16 melanoma by increasing T cell activation and decreasing myeloid suppression. Treatments with a mouse IgG1 anti-PD-1 (clone RMP1-14) and with mouse IgG2a dual specific antibodies were injected on days 3, 6, 9, and 12. (FIGS. 15A-B) C57B1/6 mice were injected subcutaneously with 50,000 PD-L2-overexpressing B16 cells. Mice were monitored to determine tumor growth (FIG. 15A) and survival (FIG. 15B). Mean±SEM (n=20) is displayed. (FIGS. 15C-H) C57B1/6 mice were injected subcutaneously with 100,000 PD-L2-overexpressing B16 cells and treated as indicated in (FIG. 15A). Lymph nodes (FIGS. 15C-E) and tumors (FIGS. 15F-H) were collected and analyzed by flow cytometry at D14. Individual values and mean are displayed.

FIGS. 16A-B show that antibody 37464 presents therapeutic advantages over 27869 and 27907. (FIG. 16A) Balb/c mice were injected subcutaneously with 100,000 CT26 cells and treated with mouse IgG1 anti-PD-1 (clone RMP1-14) or with mouse IgG2a dual specific antibodies on days 3, 6, 9, and 12. Mice were monitored to determine tumor growth. Mean±SEM (n=10) is displayed. (FIG. 16B) Serial dilutions of BiPDL versus isotype control antibodies were pre-incubated with CHO/PDL-1 cells combined with human recombinant B7.1 followed by secondary staining with a PE-labeled anti-human B7.1 antibody. Binding of the labeled PE-labeled anti-human B7.1 antibody was an indication of freely available PD-L1 on the cell surface for B7.1 binding. Nonlinear regression was used to generate best-fit curves in GraphPad Prism.

FIGS. 17A-I show selection of an optimized dual-specific antibody with no off-target binding. (FIGS. 17A-B) Vectors encoding all hits from a library screen and control vectors encoding EGFR (transfection and negative control) and CD20 (positive control), were re-arrayed/re-expressed in duplicate. Cells were probed after cell fixation with (FIG. 17A) 5 µg/mL of 37464 or (FIG. 17B) 20 µg/mL of 38002. Parallel slides were probed with 1 µg/mL Rituximab biosimilar (positive control), or no test molecule (AF647 anti-hIgG Fc secondary only). The specific interactions for the test antibodies are shown in blue (weak intensity) and green (weak/medium intensity and above); Interactions that are non-specific, but where there is a large intensity difference between test and control treatments are shown in purple; the more intense of the non-specific interactions are shown in black; the positive control interaction is shown in orange. INSR (long and short isoforms) and INSR+IGF1R cell spots are highlighted in red. (FIG. 17C) INSR$^+$ CHO cells were incubated with serial dilutions of 38002 (red), 37464 (blue) or a control (black) antibody. Fluorescence was measured by flow cytometry. Mean±SDM (n=2) is displayed for each concentration of each antibody. A dose range of 33.333-0.00511 nM was tested against INSR+ CHO cells. (FIGS. 17D-E) Chinese hamster ovary (CHO) cells expressing PD-L1 (D) or PD-L2 (FIG. 17E) were incubated with dual-specific antibodies at concentrations displayed on the x-axis and co-cultured with NFAT luciferase reporter Jurkat T cells. A higher signal indicates a more efficient blockade of the PD-1 pathway. (FIGS. 17F-G) Chinese hamster ovary (CHO) PD-L1+ CHO cells and PD-L2+ CHO cells (1:1 mixture of the two cell lines) were incubated with dual-specific antibodies at concentrations displayed on the x-axis and co-cultured with NFAT-RE luciferase reporter Jurkat T cells (FcgRIIIa for ADCC or FcgRIIa-H for ADCP). A higher signal indicates an efficient ADCC (FIG. 17F) or ADCP (FIG. 17G) activation pathway. Mean±SEM (n=3) is displayed for each concentration of each antibody. (FIGS. 17H-I) Murine melanoma cancer cells B16F10 ectopically expressing PD-L2 were incubated with dual-specific antibodies at concentrations displayed on the x-axis and co-cultured with NFAT-RE luciferase reporter Jurkat T cells (FcgRIIIa for ADCC or FcgRIIa-H for ADCP). A higher signal indicates an efficient ADCC (FIG. 17H) or ADCP (FIG. 17I) activation pathway. Nonlinear regression was used to generate best-fit curves in GraphPad Prism.

FIGS. 18A-B show characterization of the dual specific antibody 38002 with similar affinity but no binding to INSR. (FIG. 18A) Table indicating the affinity of the dual-specific antibody 38002 for monomeric PD-L1 and PD-L2. KD were measured on the Octet® platform and are indicated in Molar. (FIG. 18B) Titration curve of 38002 binding to CD274 (PD-L1), PDCD1LG2 (PD-L2), INSR long isoform, and INSR short isoform expressed on live HEK293 cells.

FIGS. 19A-H show the dual-specific antibody 38002 increases survival in B16 melanoma by increasing T cell activation and decreasing myeloid suppression. (FIG. 19A) C57BL/6 mice were implanted with PD-L2-expressing B16F10 cells. Mice received intraperitoneal treatment with an anti-mouse PD-1 (clone RMP1-14), a mouse IgG2a anti-PD-L1 antibody, a mouse IgG2a anti-PD-L2 antibody, a 1:1 mix of mouse IgG2a anti-PD-L1 and anti-PD-L2 antibodies, or the human IgG1-GASDIE 38002 dual specific antibody at days 3, 6, 9, and 12. Mean±SEM tumor volume (mm$^3$) is plotted against days post tumor inoculation. (FIG. 19B-H) C57B1/6 mice were injected subcutaneously with 100,000 PD-L2-overexpressing B16 cells. Treatments with a mouse IgG1 anti-PD-1 (clone RMP1-14) and with mouse IgG2a 38002 were injected on days 3, 6, 9, and 12 and tumors were collected and analyzed by flow cytometry at D14. Individual values and mean are displayed.

FIGS. 20A-D show C57BL/6 mice were injected with 500,000 B16-PD-L2 cells. Human IgG1-GASDIE 38002 dual specific antibody was given on days 3, 6, 9, and 12 at 20 mg/kg via IP. Mice were euthanized on day 18 and lymph nodes were collected, stained with PE-labelled antibodies against CD11b, Gr-1, Arginase-1 and FOXP3 or isotope controls, and analyzed by flow cytometry.

FIGS. 21A-B show treatment of MDA-MB-231 tumor bearing nu/nu mice with dual IMGS-001 inhibits tumor growth and reduces infiltration of CD11b+ cells. (FIG. 21A) Mean±SEM tumor volume (mm3) is plotted on the y-axis

US 12,637,518 B2

Figure 3:
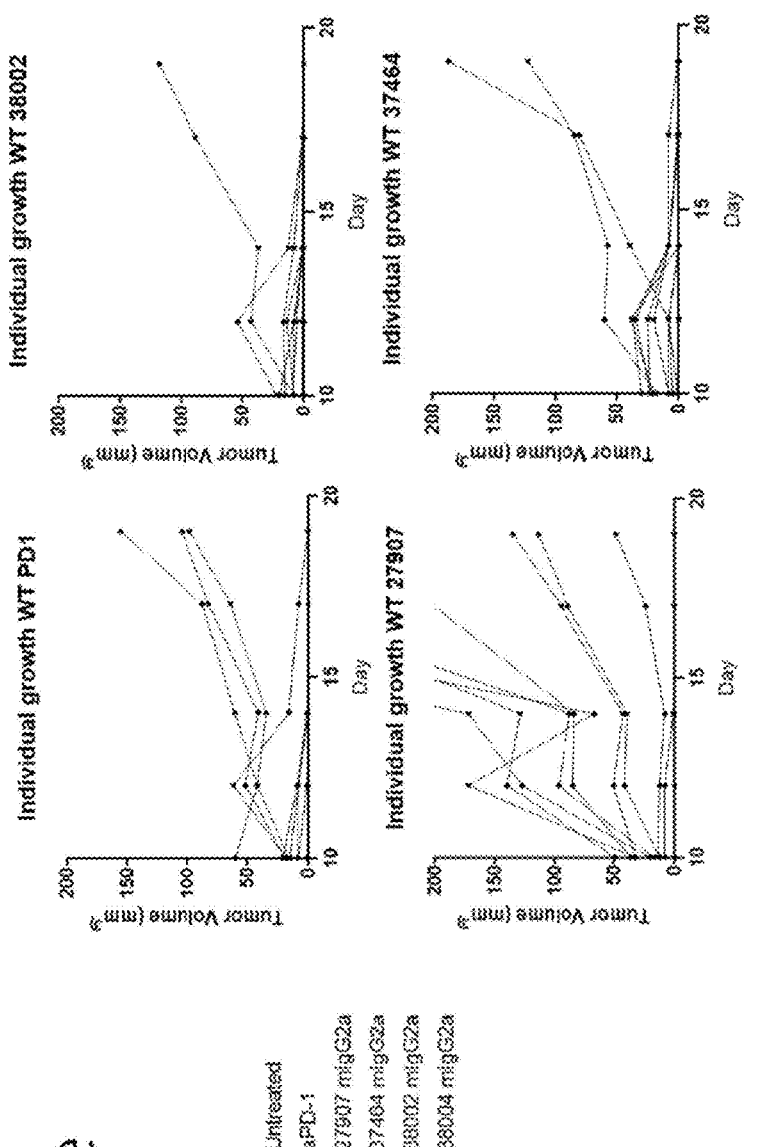
FIG. 3 illustrates treatment of CT26 parental with 38000 series PD-L1/PD-L2 dual-specific antibodies—second experiment. Parental CT26 tumors were implanted in BALB/C mice and treated on days 3, 6, and 9 with 10 mg/kg of the indicated antibody. Tumor sizes were caliper measured with 1000 mm$^3$ as an endpoint.

13 against days post tumor challenge on the x-axis. Unpaired t-tests were used to compare groups. *p<0.05; p<0.01; *p<0.001. (FIG. 21B) Immunohistochemistry with anti-CD11b in untreated and dual IMGS-001 treated tumors (magnification ×200). The histogram shows the mean percentage of CD11b+ cells ±SD detected in whole slide tumor tissue. An unpaired t-test was used to compare groups. p=0.0001.

FIG. 22 is a schematic of the development of a series of PD-L1/PD-L2 dual binding antibodies starting with ADI-16415. ADI-16415 underwent multiple rounds of affinity maturation to obtain ADI-37464.

DESCRIPTION OF ILLUSTRATIVE
EMBODIMENTS

The inventor previously generated monoclonal antibodies with binding specificity for both human PD-L1 and PD-L2 proteins. These antibodies have been demonstrated to bind to both PD-L1 and PD-L2 and thus present an opportunity to block the binding of PD-L1, PD-L2, or PD-L1 and PD-L2 to PD-1, such as by blocking PD-L1/PD-L2 interactions with PD-1 and PD-L1 interactions with B7-1. They can also be used to deliver therapeutic payloads to PD-L1, PD-L2, or PD-L1 and PD-L2 expressing cancer cells.

Recently, the inventor has engineered a dual specificity PD-L1/PD-L2 antibody to avoid significant binding to the human insulin receptor while retaining the PD-L1/PD-L2 affinities. This was accomplished by modifying light chain CDR amino acids. It was surprisingly found that the reduction in off target effect does not affect the antibody's capacity to outperform PD-1 blockade and mediate curative responses as a monotherapy. The inventors surprisingly identified a new subclass of immune checkpoint antibodies having the additional property of checkpoint cytoreduction, thus allowing for breakdown of stromal barriers to T cell infiltration of tumors as well as direct tumor cytoreduction and anti-metastatic activity. This surprising and unexpected result has particular relevance to "cold" cancers that are poorly responsive (<5%) to existing PD-1 antibodies due to the exclusion and suppression of effector T cell responses.

In addition, the inventor then engineered the Fc portion of the antibodies using clinically proven mutagenesis to mediate antibody-dependent cellular cytotoxicity (ADCC) and phagocytosis (ADCP) of multiple tumor cell lines in vitro. Mice injected with immune excluded (B16-PDL-2) and immune infiltrated (CT26, CT26-PD-L2, MC38) tumors treated with the anti-PD-L1/PD-L2 dual specific antibody showed over 50% survival, while the treatment with murine anti-PD1 showed little to no survival benefit in cold tumors. Ex vivo cell analysis of tumors and stroma components from mice treated with the dual specific antibody resulted in an increase in T cell activation and decrease in myeloid cell compartment. Lastly, treatment of nu/nu mice bearing a human triple negative breast cancer (MDA-MB-231) with dual PD-L1/PD-L2 antibody significantly inhibited tumor growth and reduced infiltration of CD11b+ cells, while clinically proven anti-PD-L1 had a very limited effect.

These findings and other aspects of the disclosure are described in even greater detail below.

I. PD-L1

A. Structure
Programmed death-ligand 1 (PD-L1) is a protein encoded by the CD274 gene. PD-L1 is a 40 kDa type 1 transmembrane protein which may play a major role in immune suppression during a variety of events such as, pregnancy, tissue allografts, autoimmune disease, cancer and other disease states. The human PD-L1 protein is encoded by the amino acid sequence shown below:

```
                                    (SEQ ID NO: 1)
MRIFAVFIFMTYWHLLNAFTVTVPKDLYVVEYGSNMTIECKFPVEKQLD

LAALIVYWEMEDKNIIQFVHGEEDLKVQHSSYRQRARLLKDQLSLGNAA

LQITDVKLQDAGVYRCMISYGGADYKRITVKVNAPYNKINQRILVVDPV

TSEHELTCQAEGYPKAEVIWTSSDHQVLSGKTTTTNSKREEKLFNVTST

LRINTTTNEIFYCTFRRLDPEENHTAELVIPELPLAHPPNERTHLVILG

AILLCLGVALTFIFRLRKGRMMDVKKCGIQDTNSKKQSDTHLEET
```

B. Function
PD-L1 is a ligand to its receptor, PD-1. PD-1 may be found on activated T cells, B cells, and myeloid cells. Binding of PD-L1 to PD-1 modulates T cell and B cell activation or inhibition. transmits an inhibitor signal that reduces proliferation of antigen specific CD8+ T cells and CD4+ helper T-cells. Binding of PD-L1 to PD-1 also induces apoptosis. This reduction of CD8+ T cells and CD4+ helper T-cells has been thought to help PD-L1 expressing cancer cells evade anti-tumor immunity (Dong et al., 2002). Upregulation of PD-L1 has been associated with evasion of the host immune system and is thought to be a cause of increased tumor aggressiveness (Thompson et al., 2004). The role of PD-L1 in evasion of anti-tumor immunity makes it an attractive target for therapeutic intervention.

II. PD-L2

A. Structure
Programmed death-ligand 2 (PD-L2) is a protein encoded by the CD273 gene. PD-L2 is a 31 kDa protein which may play a major role in immune suppression during a variety of events such as, pregnancy, tissue allografts, autoimmune disease, cancer and other disease states. The human PD-L2 protein is encoded by the amino acid sequence shown below:

```
                                    (SEQ ID NO: 2)
MIFLLLMLSLELQLHQIAALFTVTVPKELYIIEHGSNVTLECNFDTGSH

VNLGAITASLQKVENDTSPHRERATLLEEQLPLGKASFHIPQVQVRDEG

QYQCIIIYGVAWDYKYLTLKVKASYRKINTHILKVPETDEVELTCQATG

YPLAEVSWPNVSVPANTSHSRTPEGLYQVTSVLRLKPPPGRNFSCVFWN

THVRELTLASIDLQSQMEPRTHPTWLLHIFIPFCIIAFIFIATVIALRK

QLCQKLYSSKDTTKRPVTTTKREVNSAI
```

PD-L2 is initially produced with a signal peptide corresponding to amino acids 1-19 of SEQ ID NO: 2, which is subsequently removed to yield the mature protein. The mature PD-L2 protein, corresponding to amino acids 20-273 of SEQ ID NO: 2, is comprised of an lg-like V-domain, an lg-like C2-type domain, transmembrane domain, and a cytoplasmic tail.
B. Function
PD-L2 is a ligand to its receptor, PD-1. PD-1 may be found on activated T cells, B cells, and myeloid cells. Binding of PD-L2 to PD-1 begins an immunological cascade which impairs proliferation, cytokine production, cytolytic function and survival of the T cell. PD-1 transmits an inhibitor signal that reduces proliferation of antigen specific CD8+ T cells and CD4+ helper T-cells. PD-L2 has also been shown to be an independent predictor of response to the PD-1 antibody pembrolizumab across multiple cancers (Yearley et al., 2017).

III. MONOCLONAL ANTIBODIES AND PRODUCTION THEREOF

A. General Methods

Antibodies to PD-L1 and PD-L2 may be produced by standard methods as are well known in the art (see, e.g., Antibodies: A Laboratory Manual, Cold Spring Harbor Laboratory, 1988; U.S. Pat. No. 4,196,265). The methods for generating monoclonal antibodies (mAbs) generally begin along the same lines as those for preparing polyclonal antibodies. The first step for both these methods is immunization of an appropriate host or identification of subjects who are immune due to prior natural infection. As is well known in the art, a given composition for immunization may vary in its immunogenicity. It is often necessary therefore to boost the host immune system, as may be achieved by coupling a peptide or polypeptide immunogen to a carrier. Exemplary and preferred carriers are keyhole limpet hemocyanin (KLH) and bovine serum albumin (BSA). Other albumins such as ovalbumin, mouse serum albumin or rabbit serum albumin can also be used as carriers. Means for conjugating a polypeptide to a carrier protein are well known in the art and include glutaraldehyde, m-maleimidobencoyl-N-hydroxysuccinimide ester, carbodiimide and bis-biazotized benzidine. As also is well known in the art, the immunogenicity of a particular immunogen composition can be enhanced by the use of non-specific stimulators of the immune response, known as adjuvants. Exemplary and preferred adjuvants include complete Freund's adjuvant (a non-specific stimulator of the immune response containing killed *Mycobacterium tuberculosis*), incomplete Freund's adjuvants and aluminum hydroxide adjuvant.

The amount of immunogen composition used in the production of polyclonal antibodies varies upon the nature of the immunogen as well as the animal used for immunization. A variety of routes can be used to administer the immunogen (subcutaneous, intramuscular, intradermal, intravenous and intraperitoneal). The production of polyclonal antibodies may be monitored by sampling blood of the immunized animal at various points following immunization. A second, booster injection, also may be given. The process of boosting and titering is repeated until a suitable titer is achieved. When a desired level of immunogenicity is obtained, the immunized animal can be bled and the serum isolated and stored, and/or the animal can be used to generate monoclonal antibodies.

Following immunization, somatic cells with the potential for producing antibodies, specifically B lymphocytes (B cells), are selected for use in the mAb generating protocol. These cells may be obtained from biopsied spleens or lymph nodes, or from circulating blood. The antibody-producing B lymphocytes from the immunized animal are then fused with cells of an immortal myeloma cell, generally one of the same species as the animal that was immunized or human or human/mouse chimeric cells. Myeloma cell lines suited for use in hybridoma-producing fusion procedures preferably are non-antibody-producing, have high fusion efficiency, and enzyme deficiencies that render then incapable of growing in certain selective media which support the growth of only the desired fused cells (hybridomas).

Any one of a number of myeloma cells may be used, as are known to those of skill in the art (Goding, pp. 65-66, 1986; Campbell, pp. 75-83, 1984). For example, where the immunized animal is a mouse, one may use P3-X63/Ag8, X63-Ag8.653, NS1/1.Ag 41, Sp210-Ag14, PO, NSO/U, MPC-11, MPC11-X45-GTG 1.7 and S194/5XX0 Bul; for rats, one may use R210.RCY3, Y3-Ag 1.2.3, IR983F and 4B210; and U-266, GM1500-GRG2, LICR-LON-HMy2 and UC729-6 are all useful in connection with human cell fusions. One particular murine myeloma cell is the NS-1 myeloma cell line (also termed P3-NS-1-Ag4-1), which is readily available from the NIGMS Human Genetic Mutant Cell Repository by requesting cell line repository number GM3573. Another mouse myeloma cell line that may be used is the 8-azaguanine-resistant mouse murine myeloma SP2/0 non-producer cell line. More recently, additional fusion partner lines for use with human B cells have been described, including KR12 (ATCC CRL-8658; K6H6/B5 (ATCC CRL-1823 SHM-D33 (ATCC CRL-1668) and HMMA2.5 (Posner et al., 1987). The antibodies in this disclosure were generated using the SP2/0/mIL-6 cell line, an IL-6 secreting derivative of the SP2/0 line.

Methods for generating hybrids of antibody-producing spleen or lymph node cells and myeloma cells usually comprise mixing somatic cells with myeloma cells in a 2:1 proportion, though the proportion may vary from about 20:1 to about 1:1, respectively, in the presence of an agent or agents (chemical or electrical) that promote the fusion of cell membranes. Fusion methods using Sendai virus have been described by Kohler and Milstein (1975; 1976), and those using polyethylene glycol (PEG), such as 37% (v/v) PEG, by Gefter et al. (1977). The use of electrically induced fusion methods also is appropriate (Goding, pp. 71-74, 1986).

Fusion procedures usually produce viable hybrids at low frequencies, about $1 \times 10^{-6}$ to $1 \times 10^{-8}$. However, this does not pose a problem, as the viable, fused hybrids are differentiated from the parental, infused cells (particularly the infused myeloma cells that would normally continue to divide indefinitely) by culturing in a selective medium. The selective medium is generally one that contains an agent that blocks the de novo synthesis of nucleotides in the tissue culture media. Exemplary and preferred agents are aminopterin, methotrexate, and azaserine. Aminopterin and methotrexate block de novo synthesis of both purines and pyrimidines, whereas azaserine blocks only purine synthesis. Where aminopterin or methotrexate is used, the media is supplemented with hypoxanthine and thymidine as a source of nucleotides (HAT medium). Where azaserine is used, the media is supplemented with hypoxanthine. Ouabain is added if the B cell source is an Epstein Barr virus (EBV) transformed human B cell line, in order to eliminate EBV transformed lines that have not fused to the myeloma.

The preferred selection medium is HAT or HAT with ouabain. Only cells capable of operating nucleotide salvage pathways are able to survive in HAT medium. The myeloma cells are defective in key enzymes of the salvage pathway, e.g., hypoxanthine phosphoribosyl transferase (HPRT), and they cannot survive. The B cells can operate this pathway, but they have a limited life span in culture and generally die within about two weeks. Therefore, the only cells that can survive in the selective media are those hybrids formed from myeloma and B cells. When the source of B cells used for fusion is a line of EBY-transformed B cells, as here, ouabain is also used for drug selection of hybrids as EB V-transformed B cells are susceptible to drug killing, whereas the myeloma partner used is chosen to be ouabain resistant.

Culturing provides a population of hybridomas from which specific hybridomas are selected. Typically, selection of hybridomas is performed by culturing the cells by single-clone dilution in microtiter plates, followed by testing the individual clonal supernatants (after about two to three weeks) for the desired reactivity. The assay should be sensitive, simple and rapid, such as radioimmunoassays, enzyme immunoassays, cytotoxicity assays, plaque assays dot immunobinding assays, and the like.

The selected hybridomas are then serially diluted or single-cell sorted by flow cytometric sorting and cloned into individual antibody-producing cell lines, which clones can then be propagated indefinitely to provide mAbs. The cell lines may be exploited for MAb production in two basic ways. A sample of the hybridoma can be injected (often into the peritoneal cavity) into an animal (e.g., a mouse). Optionally, the animals are primed with a hydrocarbon, especially oils such as pristane (tetramethylpentadecane) prior to injection. When human hybridomas are used in this way, it is optimal to inject immunocompromised mice, such as SCID mice, to prevent tumor rejection. The injected animal develops tumors secreting the specific monoclonal antibody produced by the fused cell hybrid. The body fluids of the animal, such as serum or ascites fluid, can then be tapped to provide mAbs in high concentration. The individual cell lines could also be cultured in vitro, where the mAbs are naturally secreted into the culture medium from which they can be readily obtained in high concentrations. Alternatively, human hybridoma cells lines can be used in vitro to produce immunoglobulins in cell supernatant. The cell lines can be adapted for growth in serum-free medium to optimize the ability to recover human monoclonal immunoglobulins of high purity.

Monoclonal antibodies produced by either means may be further purified, if desired, using filtration, centrifugation and various chromatographic methods such as FPLC or affinity chromatography. Fragments of the monoclonal antibodies of the disclosure can be obtained from the purified monoclonal antibodies by methods which include digestion with enzymes, such as pepsin or papain, and/or by cleavage of disulfide bonds by chemical reduction. Alternatively, monoclonal antibody fragments encompassed by the present disclosure can be synthesized using an automated peptide synthesizer.

It also is contemplated that a molecular cloning approach may be used to generate monoclonal antibodies. For this, RNA can be isolated from the hybridoma line and the antibody genes obtained by RT-PCR and cloned into an immunoglobulin expression vector. Alternatively, combinatorial immunoglobulin phagemid libraries are prepared from RNA isolated from the cell lines and phagemids expressing appropriate antibodies are selected by panning using viral antigens. The advantages of this approach over conventional hybridoma techniques are that approximately 104 times as many antibodies can be produced and screened in a single round, and that new specificities are generated by H and L chain combination which further increases the chance of finding appropriate antibodies.

Yeast-based antibody libraries may be designed rationally, and antibodies may be selected and/or isolated from such yeast-based antibody presentation libraries, as disclosed in, for example, WO2012/009568; WO2009/036379; WO2010/105256; WO2003/074679; U.S. Pat. Nos. 8,691,730; and 9,354,228. The antibodies may be expressed as full length IgGs from any desired cell type as disclosed in the above, and purified.

Other U.S. patents, each incorporated herein by reference, that teach the production of antibodies useful in the present disclosure include U.S. Pat. No. 5,565,332, which describes the production of chimeric antibodies using a combinatorial approach; U.S. Pat. No. 4,816,567 which describes recombinant immunoglobulin preparations; and U.S. Pat. No. 4,867,973 which describes antibody-therapeutic agent conjugates.

B. Antibodies of the Present Disclosure

Antibodies according to the present disclosure may be defined, in the first instance, by their binding specificity, i.e., binding to PD-L1 and PD-L2. Those of skill in the art, by assessing the binding specificity/affinity of a given antibody using techniques well known to those of skill in the art, can determine whether such antibodies fall within the scope of the instant claims. In one aspect, there are provided monoclonal antibodies having CDR's from the heavy and light chains as described above. Such antibodies may be produced by the clones discussed below in the Examples section using methods described herein.

In a second aspect, the antibodies may be defined by their variable sequence, which include additional "framework" regions. These are provided for example in SEQ ID NO:3/ SEQ ID NO:4 and SEQ ID NO:5/SEQ ID NO:6 that encode or represent full variable regions. Furthermore, the antibodies sequences may vary from these sequences, optionally using methods discussed in greater detail below. For example, nucleic acid sequences may vary from those set out above in that (a) the variable regions may be segregated away from the constant domains of the light and heavy chains, (b) the nucleic acids may vary from those set out above while not affecting the residues encoded thereby, (c) the nucleic acids may vary from those set out above by a given percentage, e.g., at least or about 70%, 75%, 80%, 85%, 90%, 91%, 92%, 93%, 94%, 95%, 96%, 97%, 98% or 99% homology, (d) the nucleic acids may vary from those set out above by virtue of the ability to hybridize under high stringency conditions, as exemplified by low salt and/or high temperature conditions, such as provided by about 0.02 M to about 0.15 M NaCl at temperatures of about 50° C. to about 70° C., (e) the amino acids may vary from those set out above by a given percentage, e.g., at least or about 80%, 85%, 90%, 91%, 92%, 93%, 94%, 95%, 96%, 97%, 98% or 99% homology, or (f) the amino acids may vary from those set out above by permitting conservative substitutions (discussed below). Each of the foregoing applies to the nucleic acid sequences set forth above and the amino acid sequences set forth above.

C. Engineering of Antibody Sequences

In various embodiments, one may choose to engineer sequences of the identified antibodies for a variety of reasons, such as improved expression, improved cross-reactivity or diminished off-target binding. The following is a general discussion of relevant techniques for antibody engineering.

Hybridomas may be cultured, then cells lysed, and total RNA extracted. Random hexamers may be used with RT to generate cDNA copies of RNA, and then PCR performed using a multiplex mixture of PCR primers expected to amplify all human variable gene sequences. PCR product can be cloned into pGEM-T Easy vector, then sequenced by automated DNA sequencing using standard vector primers. Assay of binding and neutralization may be performed using antibodies collected from hybridoma supernatants and purified by FPLC, using Protein G columns.

Recombinant full-length IgG antibodies may be generated by subcloning heavy and light chain Fv DNAs from the cloning vector into an IgG plasmid vector, transfected into 293 Freestyle cells or CHO cells, and antibodies were collected an purified from the 293 or CHO cell supernatant.

The rapid availability of antibody produced in the same host cell and cell culture process as the final cGMP manu-facturing process has the potential to reduce the duration of process development programs. Lonza has developed a generic method using pooled transfectants grown in CD ACF medium, for the rapid production of small quantities (up to 50 g) of antibodies in CHO cells. Although slightly slower than a true transient system, the advantages include a higher product concentration and use of the same host and process as the production cell line. Example of growth and productivity of GS-CHO pools, expressing a model anti-body, in a disposable bioreactor: in a disposable bag biore-actor culture (5 L working volume) operated in fed-batch mode, a harvest antibody concentration of 2 g/L was achieved within 9 weeks of transfection.

Antibodies, and antibody libraries from which such anti-bodies may be selected and/or isolated, may be rationally designed and synthesized, such as by the Adimab® tech-nology, as disclosed in, for example, WO2012/009568; WO2009/036379; WO2010/105256; WO2003/074679; U.S. Pat. Nos. 8,691,730; and 9,354,228. This method of synthesis antibodies requires that the nucleotide sequence coding for the desired or designed antibody be inserted into a vector for ectopic expression. Then the desired antibodies may be expressed as full chain IgG molecules and purified.

Antibody molecules will comprise fragments (such as F(ab'), F(ab'h) that are produced, for example, by the pro-teolytic cleavage of the mAbs, or single-chain immuno-globulins producible, for example, via recombinant means. Such antibody derivatives are monovalent. In one embodi-ment, such fragments can be combined with one another, or with other antibody fragments or receptor ligands to form "chimeric" binding molecules. Significantly, such chimeric molecules may contain substituents capable of binding to different epitopes of the same molecule.

In related embodiments, the antibody is a derivative of the disclosed antibodies, e.g., an antibody comprising the CDR sequences identical to those in the disclosed antibodies (e.g., a chimeric, or CDR-grafted antibody). Alternatively, one may wish to make modifications, such as introducing con-servative changes into an antibody molecule. In making such changes, the hydropathic index of amino acids may be considered. The importance of the hydropathic amino acid index in conferring interactive biologic function on a protein is generally understood in the art (Kyte and Doolittle, 1982). It is accepted that the relative hydropathic character of the amino acid contributes to the secondary structure of the resultant protein, which in turn defines the interaction of the protein with other molecules, for example, enzymes, sub-strates, receptors, DNA, antibodies, antigens, and the like.

It also is understood in the art that the substitution of like amino acids can be made effectively on the basis of hydro-philicity. U.S. Pat. No. 4,554,101, which is incorporated herein by reference, discloses that the greatest local average hydrophilicity of a protein, as governed by the hydrophilic-ity of its adjacent amino acids, correlates with a biological property of the protein. As detailed in U.S. Pat. No. 4,554,101, the following hydrophilicity values have been assigned to amino acid residues: basic amino acids: arginine (+3.0), lysine (+3.0), and histidine (−0.5); acidic amino acids: aspartate (+3.0±1), glutamate (+3.0±1), asparagine (+0.2), and glutamine (+0.2); hydrophilic, nonionic amino acids: serine (+0.3), asparagine (+0.2), glutamine (+0.2), and threonine (−0.4), sulfur containing amino acids: cysteine (−1.0) and methionine (−1.3); hydrophobic, nonaromatic amino acids: valine (−1.5), leucine (−1.8), isoleucine (−1.8), praline (−0.5±1), alanine (−0.5), and glycine (0); hydropho-bic, aromatic amino acids: tryptophan (−3.4), phenylalanine (−2.5), and tyrosine (−2.3).

It is understood that an amino acid can be substituted for another having a similar hydrophilicity and produce a bio-logically or immunologically modified protein. In such changes, the substitution of amino acids whose hydrophi-licity values are within ±2 is preferred, those that are within ±1 are particularly preferred, and those within ±0.5 are even more particularly preferred.

As outlined above, amino acid substitutions generally are based on the relative similarity of the amino acid side-chain substituents, for example, their hydrophobicity, hydrophi-licity, charge, size, and the like. Exemplary substitutions that take into consideration the various foregoing characteristics are well known to those of skill in the art and include: arginine and lysine; glutamate and aspartate; serine and threonine; glutamine and asparagine; and valine, leucine and isoleucine.

The present disclosure also contemplates isotype modifi-cation. By modifying the Fe region to have a different isotype, different functionalities can be achieved. For example, changing to IgG1 can increase antibody dependent cell cytotoxicity, switching to class A can improve tissue distribution, and switching to class M can improve valency.

Modified antibodies may be made by any technique known to those of skill in the art, including expression through standard molecular biological techniques, or the chemical synthesis of polypeptides. Methods for recombi-nant expression are addressed elsewhere in this document.

D. Single Chain Antibodies

A Single Chain Variable Fragment (scFv) is a fusion of the variable regions of the heavy and light chains of immuno-globulins, linked together with a short (usually serine, glycine) linker. This chimeric molecule retains the specific-ity of the original immunoglobulin, despite removal of the constant regions and the introduction of a linker peptide. This modification usually leaves the specificity unaltered. These molecules were created historically to facilitate phage display where it is highly convenient to express the antigen binding domain as a single peptide. Alternatively, scFv can be created directly from subcloned heavy and light chains derived from a hybridoma. Single chain variable fragments lack the constant Fc region found in complete antibody molecules, and thus, the common binding sites (e.g., protein A/G) used to purify antibodies. These fragments can often be purified/immobilized using Protein L since Protein L interacts with the variable region of kappa light chains.

Flexible linkers generally are comprised of helix- and turn-promoting amino acid residues such as alanine, serine and glycine. However, other residues can function as well. Tang et al. (1996) used phage display as a means of rapidly selecting tailored linkers for single-chain antibodies (scFvs) from protein linker libraries. A random linker library was constructed in which the genes for the heavy and light chain variable domains were linked by a segment encoding an 18-amino acid polypeptide of variable composition. The scFv repertoire (approx. 5×106 different members) was displayed on filamentous phage and subjected to affinity selection with hapten. The population of selected variants exhibited significant increases in binding activity but retained considerable sequence diversity. Screening 1054 individual variants subsequently yielded a catalytically active scFv that was produced efficiently in soluble form. Sequence analysis revealed a conserved pro line in the linker two residues after the V H C terminus and an abundance of arginines and pralines at other positions as the only common features of the selected tethers.

The recombinant antibodies of the present disclosure may also involve sequences or moieties that permit dimerization or multimerization of the receptors. Such sequences include those derived from IgA, which permit formation of multimers in conjunction with the J-chain. Another multimerization domain is the Gal4 dimerization domain. In other embodiments, the chains may be modified with agents such as biotin/avidin, which permit the combination of two antibodies.

In a separate embodiment, a single-chain antibody can be created by joining receptor light and heavy chains using a non-peptide linker or chemical unit. Generally, the light and heavy chains will be produced in distinct cells, purified, and subsequently linked together in an appropriate fashion (i.e., the N-terminus of the heavy chain being attached to the C-terminus of the light chain via an appropriate chemical bridge).

Cross-linking reagents are used to form molecular bridges that tie functional groups of two different molecules, e.g., a stabilizing and coagulating agent. However, it is contemplated that dimers or multimers of the same analog or heteromeric complexes comprised of different analogs can be created. To link two different compounds in a stepwise manner, hetero-bifunctional cross-linkers can be used that eliminate unwanted homopolymer formation.

An exemplary hetero-bifunctional cross-linker contains two reactive groups: one reacting with primary amine group (e.g., N-hydroxy succinimide) and the other reacting with a thiol group (e.g., pyridyl disulfide, maleimides, halogens, etc.). Through the primary amine reactive group, the cross-linker may react with the lysine residue(s) of one protein (e.g., the selected antibody or fragment) and through the thiol reactive group, the cross-linker, already tied up to the first protein, reacts with the cysteine residue (free sulfhydryl group) of the other protein (e.g., the selective agent).

It is preferred that a cross-linker having reasonable stability in blood will be employed. Numerous types of disulfide-bond containing linkers are known that can be successfully employed to conjugate targeting and therapeutic/preventative agents. Linkers that contain a disulfide bond that is sterically hindered may prove to give greater stability in vivo, preventing release of the targeting peptide prior to reaching the site of action. These linkers are thus one group of linking agents.

Another cross-linking reagent is SMPT, which is a bifunctional cross-linker containing a disulfide bond that is "sterically hindered" by an adjacent benzene ring and methyl groups. It is believed that steric hindrance of the disulfide bond serves a function of protecting the bond from attack by thiolate anions such as glutathione which can be present in tissues and blood, and thereby help in preventing decoupling of the conjugate prior to the delivery of the attached agent to the target site.

The SMPT cross-linking reagent, as with many other known cross-linking reagents, lends the ability to cross-link functional groups such as the SH of cysteine or primary amines (e.g., the epsilon amino group of lysine). Another possible type of crosslinker includes the hetero-bifunctional photoreactive phenylazides containing a cleavable disulfide bond such as sulfosuccinimidyl-2-(p-azido salicylamido) ethyl-1,3'dithiopropionate. The N-hydroxy-succinimidyl group reacts with primary amino groups and the phenylazide (upon photolysis) reacts non-selectively with any amino acid residue.

In addition to hindered cross-linkers, non-hindered linkers also can be employed in accordance herewith. Other useful cross-linkers, not considered to contain or generate a protected disulfide, include SATA, SPDP and 2-iminothiolane (Wawrzynczak & Thorpe, 1987). The use of such cross-linkers is well understood in the art. Another embodiment involves the use of flexible linkers.

U.S. Pat. No. 4,680,338 describes bifunctional linkers useful for producing conjugates of ligands with amine-containing polymers and/or proteins, especially for forming antibody conjugates with chelators, drugs, enzymes, detectable labels and the like. U.S. Pat. Nos. 5,141,648 and 5,563,250 disclose cleavable conjugates containing a labile bond that is cleavable under a variety of mild conditions. This linker is particularly useful in that the agent of interest may be bonded directly to the linker, with cleavage resulting in release of the active agent. Particular uses include adding a free amino or free sulfhydryl group to a protein, such as an antibody, or a drug.

U.S. Pat. No. 5,856,456 provides peptide linkers for use in connecting polypeptide constituents to make fusion proteins, e.g., single chain antibodies. The linker is up to about 50 amino acids in length, contains at least one occurrence of a charged amino acid (preferably arginine or lysine) followed by a praline, and is characterized by greater stability and reduced aggregation. U.S. Pat. No. 5,880,270 discloses aminooxy-containing linkers useful in a variety of immunodiagnostic and separative techniques.

E. Purification

In certain embodiments, the antibodies of the present disclosure may be purified. The term "purified," as used herein, is intended to refer to a composition, isolatable from other components, wherein the protein is purified to any degree relative to its naturally-obtainable state. A purified protein therefore also refers to a protein, free from the environment in which it may naturally occur. Where the term "substantially purified" is used, this designation will refer to a composition in which the protein or peptide forms the major component of the composition, such as constituting about 50%, about 60%, about 70%, about 80%, about 90%, about 95% or more of the proteins in the composition.

Protein purification techniques are well known to those of skill in the art. These techniques involve, at one level, the crude fractionation of the cellular milieu to polypeptide and non-polypeptide fractions. Having separated the polypeptide from other proteins, the polypeptide of interest may be further purified using chromatographic and electrophoretic techniques to achieve partial or complete purification (or purification to homogeneity). Analytical methods particularly suited to the preparation of a pure peptide are ion-exchange chromatography, exclusion chromatography; polyacrylamide gel electrophoresis; isoelectric focusing. Other methods for protein purification include, precipitation with ammonium sulfate, PEG, antibodies and the like or by heat denaturation, followed by centrifugation; gel filtration, reverse phase, hydroxylapatite and affinity chromatography; and combinations of such and other techniques.

In purifying an antibody of the present disclosure, it may be desirable to express the polypeptide in a prokaryotic or eukaryotic expression system and extract the protein using denaturing conditions. The polypeptide may be purified from other cellular components using an affinity column, which binds to a tagged portion of the polypeptide. As is generally known in the art, it is believed that the order of conducting the various purification steps may be changed, or that certain steps may be omitted, and still result in a suitable method for the preparation of a substantially purified protein or peptide.

Commonly, complete antibodies are fractionated utilizing agents (i.e., protein A) that bind the Fe portion of the antibody. Alternatively, antigens may be used to simultaneously purify and select appropriate antibodies. Such methods often utilize the selection agent bound to a support, such as a column, filter or bead. The antibodies is bound to a support, contaminants removed (e.g., washed away), and the antibodies released by applying conditions (salt, heat, etc.).

Various methods for quantifying the degree of purification of the protein or peptide will be known to those of skill in the art in light of the present disclosure. These include, for example, determining the specific activity of an active fraction, or assessing the amount of polypeptides within a fraction by SDS/PAGE analysis. Another method for assessing the purity of a fraction is to calculate the specific activity of the fraction, to compare it to the specific activity of the initial extract, and to thus calculate the degree of purity. The actual units used to represent the amount of activity will, of course, be dependent upon the particular assay technique chosen to follow the purification and whether or not the expressed protein or peptide exhibits a detectable activity.

It is known that the migration of a polypeptide can vary, sometimes significantly, with different conditions of SDS/PAGE (Capaldi et al., 1977). It will therefore be appreciated that under differing electrophoresis conditions, the apparent molecular weights of purified or partially purified expression products may vary.

IV. PHARMACEUTICAL FORMULATIONS AND TREATMENT OF CANCER

A. Cancers

Cancer results from the outgrowth of a clonal population of cells from tissue. The development of cancer, referred to as carcinogenesis, can be modeled and characterized in a number of ways. An association between the development of cancer and inflammation has long-been appreciated. The inflammatory response is involved in the host defense against microbial infection, and also drives tissue repair and regeneration. Considerable evidence points to a connection between inflammation and a risk of developing cancer, i.e., chronic inflammation can lead to dysplasia.

Cancer cells to which the methods of the present disclosure can be applied include generally any cell that expresses PD-L1, PD-L2, or PD-L1 and PD-L2, and more particularly, that overexpresses PD-L1, PD-L2, or PD-L1 and PD-L2. An appropriate cancer cell can be a breast cancer, lung cancer, colon cancer, pancreatic cancer, renal cancer, stomach cancer, liver cancer, bone cancer, hematological cancer (e.g., leukemia or lymphoma), neural tissue cancer, melanoma, ovarian cancer, testicular cancer, prostate cancer, cervical cancer, vaginal cancer, or bladder cancer cell. In addition, the methods of the disclosure can be applied to a wide range of species, e.g., humans, non-human primates (e.g., monkeys, baboons, or chimpanzees), horses, cattle, pigs, sheep, goats, dogs, cats, rabbits, guinea pigs, gerbils, hamsters, rats, and mice. Cancers may also be recurrent, metastatic and/or multi-drug resistant, and the methods of the present disclosure may be particularly applied to such cancers so as to render them resectable, to prolong or re-induce remission, to inhibit angiogenesis, to prevent or limit metastasis, and/or to treat multi-drug resistant cancers. At a cellular level, this may translate into killing cancer cells, inhibiting cancer cell growth, or otherwise reversing or reducing the malignant phenotype of tumor cells.

B. Formulation and Administration

The present disclosure provides pharmaceutical compositions comprising dual specific antibodies directed to PD-L1 and PD-L2 (DSPDL). In a specific embodiment, the term "pharmaceutically acceptable" means approved by a regulatory agency of the Federal or a state government or listed in the U.S. Pharmacopeia or other generally recognized pharmacopeia for use in animals, and more particularly in humans. The term "carrier" refers to a diluent, excipient, or vehicle with which the therapeutic is administered. Such pharmaceutical carriers can be sterile liquids, such as water and oils, including those of petroleum, animal, vegetable or synthetic origin, such as peanut oil, soybean oil, mineral oil, sesame oil and the like. Other suitable pharmaceutical excipients include starch, glucose, lactose, sucrose, saline, dextrose, gelatin, malt, rice, flour, chalk, silica gel, sodium stearate, glycerol monostearate, talc, sodium chloride, dried skim milk, glycerol, propylene glycol, water, ethanol and the like.

The compositions can be formulated as neutral or salt forms. Pharmaceutically acceptable salts include those formed with anions such as those derived from hydrochloric, phosphoric, acetic, oxalic, tartaric acids, etc., and those formed with cations such as those derived from sodium, potassium, ammonium, calcium, ferric hydroxides, isopropylamine, triethylamine, 2-ethylamino ethanol, histidine, procaine, etc.

The antibodies of the present disclosure may include classic pharmaceutical preparations. Administration of these compositions according to the present disclosure will be via any common route so long as the target tissue is available via that route. This includes oral, nasal, buccal, rectal, vaginal or topical. Alternatively, administration may be by intradermal, subcutaneous, intramuscular, intraperitoneal or intravenous injection. Such compositions would normally be administered as pharmaceutically acceptable compositions, described supra. Of particular interest is direct intratumoral administration, perfusion of a tumor, or administration local or regional to a tumor, for example, in the local or regional vasculature or lymphatic system, or in a resected tumor bed.

The active compounds may also be administered parenterally or intraperitoneally. Solutions of the active compounds as free base or pharmacologically acceptable salts can be prepared in water suitably mixed with a surfactant, such as hydroxypropylcellulose. Dispersions can also be prepared in glycerol, liquid polyethylene glycols, and mixtures thereof and in oils. Under ordinary conditions of storage and use, these preparations contain a preservative to prevent the growth of microorganisms.

C. Combination Therapies

In the context of the present disclosure, it also is contemplated that dual specific antibodies to PD-L1 and PD-L2 (Dual PDL) described herein could be used similarly in conjunction with chemo- or radiotherapeutic intervention, or other treatments. It also may prove effective, in particular, to combine bispecific PD-L1 and PD-L2 antibodies with other therapies that target different aspects of PD-L1 or PD-L2 function, such as peptides and small molecules that target the PD-L 1 or PD-L2 cytoplasmic domain.

To kill cells, inhibit cell growth, inhibit metastasis, inhibit angiogenesis or otherwise reverse or reduce the malignant phenotype of tumor cells, using the methods and compositions of the present disclosure, one would generally contact a "target" cell with a bispecific anti-PD-L1 and anti-PD-L2 antibody according to the present disclosure and at least one other agent. These compositions would be provided in a combined amount effective to kill or inhibit proliferation of the cell. This process may involve contacting the cells with the bispecific anti-PD-L1 and anti-PD-L2 antibody according to the present disclosure and the other agent(s) or factor(s) at the same time. This may be achieved by contacting the cell with a single composition or pharmacological formulation that includes both agents, or by contacting the cell with two distinct compositions or formulations, at the same time, wherein one composition includes the bispecific anti-PD-L1 and anti-PD-L2 antibody according to the present disclosure and the other includes the other agent.

Alternatively, the bispecific anti-PD-L1 and anti-PD-L2 antibody therapy may precede or follow the other agent treatment by intervals ranging from minutes to weeks. In embodiments where the other agent and the bispecific anti-PD-L1 and anti-PDL2 antibody are applied separately to the cell, one would generally ensure that a significant period of time did not expire between each delivery, such that the agent and expression construct would still be able to exert an advantageously combined effect on the cell. In such instances, it is contemplated that one would contact the cell with both modalities within about 12-24 hours of each other and, more preferably, within about 6-12 hours of each other, with a delay time of only about 12 hours being most preferred. In some situations, it may be desirable to extend the time period for treatment significantly, however, where several days (2, 3, 4, 5, 6 or 7) to several weeks (1, 2, 3, 4, 5, 6, 7 or 8) lapse between the respective administrations.

It also is conceivable that more than one administration of either the bispecific anti-PD-L1 and anti-PD-L2 antibody or the other agent will be desired. Various combinations may be employed, where a bispecific anti-PD-L1 and anti-PD-L2 antibody according to the present disclosure therapy is "A" and the other therapy is "B", as exemplified below:

A/B/A B/A/B B/B/A A/A/B B/A/A A/B/B B/B/B/A B/B/A/B

A/A/B/B A/B/A/B A/B/B/A B/B/A/A B/A/B/A B/A/A/B B/B/B/A

A/A/A/B B/A/A/A A/B/A/A A/A/B/A A/B/B/B B/A/B/B B/B/A/B

Administration of the therapeutic agents of the present invention to a patient will follow general protocols for the administration of that particular secondary therapy, taking into account the toxicity, if any, of the antibody treatment. It is expected that the treatment cycles would be repeated as necessary. It also is contemplated that various standard therapies, as well as surgical intervention, may be applied in combination with the described cancer therapies.

The skilled artisan is directed to "Remington's Pharmaceutical Sciences" 15th Edition, Chapter 33, in particular pages 624-652. Some variation in dosage will necessarily occur depending on the condition of the subject being treated. The person responsible for administration will, in any event, determine the appropriate dose for the individual subject. Moreover, for human administration, preparations should meet sterility, pyrogenicity, general safety and purity standards as required by FDA Office of Biologics standards.

1. Chemotherapy

Cancer therapies also include a variety of combination therapies with both chemical and radiation-based treatments. Combination chemotherapies include, for example, cisplatin (CDDP), carboplatin, procarbazine, mechlorethamine, cyclophosphamide, camptothecin, ifosfamide, melphalan, chlorambucil, busulfan, nitrosurea, dactinomycin, daunorubicin, doxorubicin, bleomycin, plicomycin, mitomycin, etoposide (VP16), tamoxifen, raloxifene, estrogen receptor binding agents, taxol, gemcitabien, navelbine, farnesyl-protein transferase inhibitors, transplatinum, 5-fluorouracil, vincristine, vinblastine and methotrexate, Temazolomide (an aqueous form of DTIC), or any analog or derivative variant of the foregoing. The combination of chemotherapy with biological therapy is known as biochemotherapy. The present invention contemplates any chemotherapeutic agent that may be employed or known in the art for treating or preventing cancers.

2. Radiotherapy

Other factors that cause DNA damage and have been used extensively include what are commonly known as y-rays, X-rays, and/or the directed delivery of radioisotopes to tumor cells. Other forms of DNA damaging factors are also contemplated such as microwaves and UV-irradiation. It is most likely that all of these factors effect a broad range of damage on DNA, on the precursors of DNA, on the replication and repair of DNA, and on the assembly and maintenance of chromosomes. Dosage ranges for X-rays range from daily doses of 50 to 200 roentgens for prolonged periods of time (3 to 4 wk), to single doses of 2000 to 6000 roentgens. Dosage ranges for radioisotopes vary widely, and depend on the half-life of the isotope, the strength and type of radiation emitted, and the uptake by the neoplastic cells.

The terms "contacted" and "exposed," when applied to a cell, are used herein to describe the process by which a therapeutic agent and a chemotherapeutic or radiotherapeutic agent are delivered to a target cell or are placed in direct juxtaposition with the target cell. To achieve cell killing or stasis, both agents are delivered to a cell in a combined amount effective to kill the cell or prevent it from dividing.

3. Immunotherapy

Immunotherapeutics, generally, rely on the use of immune effector cells and molecules to target and destroy cancer cells. The immune effector may be, for example, an antibody specific for some marker on the surface of a tumor cell. The antibody alone may serve as an effector of therapy or it may recruit other cells to actually effect cell killing. The antibody also may be conjugated to a drug or toxin (chemotherapeutic, radionuclide, ricin A chain, cholera toxin, pertussis toxin, etc.) and serve merely as a targeting agent. Alternatively, the effector may be a lymphocyte carrying a surface molecule that interacts, either directly or indirectly, with a tumor cell target. Various effector cells include cytotoxic T-cells and NK cells. The combination of therapeutic modalities, i.e., direct cytotoxic activity and inhibition or reduction of Fortilin would provide therapeutic benefit in the treatment of cancer.

Immunotherapy could also be used as part of a combined therapy. The general approach for combined therapy is discussed below. In one aspect of immunotherapy, the tumor cell must bear some marker that is amenable to targeting, i.e., is not present on the majority of other cells. Many tumor markers exist and any of these may be suitable for targeting in the context of the present invention. Common tumor markers include carcinoembryonic antigen, prostate specific antigen, urinary tumor associated antigen, fetal antigen, tyrosinase (p97), gp68, TAG-72, HMFG, Sialyl Lewis Antigen, MucA, MucB, PLAP, estrogen receptor, laminin receptor, erb B and p155. An alternative aspect of immunotherapy is to anticancer effects with immune stimulatory effects. Immune stimulating molecules also exist including cytokines such as IL-2, IL-4, IL-12, GM-CSP, gamma-IFN, chemokines such as MIP-1, MCP-1, IL-8 and growth factors such as FL T3 ligand. Combining immune stimulating molecules, either as proteins or using gene delivery in combination with a tumor suppressor such as mda-7 has been shown to enhance anti-tumor effects (Ju et al., 2000).

As discussed earlier, examples of immunotherapies currently under investigation or in use are immune adjuvants (e.g., *Mycobacterium bovis, Plasmodium falciparum*, dinitrochlorobenzene and aromatic compounds) (U.S. Pat. Nos. 5,801,005; 5,739,169; Hui and Hashimoto, 1998; Christodoulides et al., 1998), cytokine therapy (e.g., interferons, and; IL-1, GM-CSP and TNF) (Bukowski et al., 1998; Davidson et al., 1998; Hellstrand et al., 1998) gene therapy (e.g., TNF, IL-1, IL-2, p53) (Qin et al., 1998; Austin-Ward and Villaseca, 1998; U.S. Pat. Nos. 5,830,880 and 5,846, 945) and monoclonal antibodies (e.g., anti-ganglioside GM2, anti-HER-2, anti-p185) (Pietras et al., 1998; Hanibuchi et al., 1998; U.S. Pat. No. 5,824,311). Herceptin (trastuzumab) is a chimeric (mouse-human) monoclonal antibody that blocks the HER2-neu receptor. It possesses antitumor activity and has been approved for use in the treatment of malignant tumors (Dillman, 1999). Combination therapy of cancer with herceptin and chemotherapy has been shown to be more effective than the individual therapies. Thus, it is contemplated that one or more anti-cancer therapies may be employed with the tumor-associated HLA-restricted peptide therapies described herein.

In adoptive immunotherapy, the patient's circulating lymphocytes, or tumor infiltrated lymphocytes, are isolated in vitro, activated by lymphokines such as IL-2 or transduced with genes for tumor necrosis, and readministered (Rosenberg et al., 1988; 1989). To achieve this, one would administer to an animal, or human patient, an immunologically effective amount of activated lymphocytes in combination with an adjuvant-incorporated antigenic peptide composition as described herein. The activated lymphocytes will most preferably be the patient's own cells that were earlier isolated from a blood or tumor sample and activated (or "expanded") in vitro. This form of immunotherapy has produced several cases of regression of melanoma and renal carcinoma, but the percentage of responders was few compared to those who did not respond.

A number of different approaches for passive immunotherapy of cancer exist. They may be broadly categorized into the following: injection of antibodies alone; injection of antibodies coupled to toxins or chemotherapeutic agents; injection of antibodies coupled to radioactive isotopes; injection of anti-idiotype antibodies; and finally, purging of tumor cells in bone marrow.

Human monoclonal antibodies are employed in passive immunotherapy, as they produce few or no side effects in the patient. However, their application is somewhat limited by their scarcity and have so far only been administered intralesionally. Human monoclonal antibodies to ganglioside antigens have been administered intralesionally to patients suffering from cutaneous recurrent melanoma (Irie & Morton, 1986). Regression was observed in six out of ten patients, following, daily or weekly, intralesional injections. In another study, moderate success was achieved from intralesional injections of two human monoclonal antibodies (Irie et al., 1989). Possible therapeutic antibodies include anti-TNF, anti-CD25, anti-CD3, anti-CD20, CTLA-4-IG, and anti-CD28.

It may be favorable to administer more than one monoclonal antibody directed against two different antigens or even antibodies with multiple antigen specificity. Treatment protocols also may include administration of lymphokines or other immune enhancers as described by Bajorin et al. (1988). The development of human monoclonal antibodies is described in further detail elsewhere in the specification.

4. Gene Therapy

In yet another embodiment, the secondary treatment is a gene therapy in which a therapeutic polynucleotide is administered before, after, or at the same time as the tumor-associated HLA-restricted peptide is administered. Delivery of a vector encoding the tumor-associated HLA-restricted peptide in conjunction with a second vector encoding one of the following gene products will have a combined anti-hyperproliferative effect on target tissues. Alternatively, a single vector encoding both genes may be used. A variety of proteins are encompassed within the invention, some of which are described below. Various genes that may be targeted for gene therapy of some form in combination with the present invention are well known to one of ordinary skill in the art and may comprise any gene involved in cancers.

Inducers of Cellular Proliferation. The proteins that induce cellular proliferation further fall into various categories dependent on function. The commonality of all of these proteins is their ability to regulate cellular proliferation. For example, a form of PDGF, the sis oncogene, is a secreted growth factor. Oncogenes rarely arise from genes encoding growth factors, and at the present, sis is the only known naturally occurring oncogenic growth factor. In one embodiment of the present invention, it is contemplated that antisense mRNA directed to a particular inducer of cellular proliferation is used to prevent expression of the inducer of cellular proliferation.

The proteins PMS, ErbA, ErbB and neu are growth factor receptors. Mutations to these receptors result in loss of regulatable function. For example, a point mutation affecting the transmembrane domain of the Neu receptor protein results in the neu oncogene. The erbA oncogene is derived from the intracellular receptor for thyroid hormone. The modified oncogenic ErbA receptor is believed to compete with the endogenous thyroid hormone receptor, causing uncontrolled growth.

The largest class of oncogenes includes the signal transducing proteins (e.g., Src, Abl and Ras). The protein Src is a cytoplasmic protein-tyrosine kinase, and its transformation from proto-oncogene to oncogene in some cases, results via mutations at tyrosine residue 527. In contrast, transformation of GTPase protein ras from protooncogene to oncogene, in one example, results from a valine to glycine mutation at amino acid 12 in the sequence, reducing ras GTPase activity. The proteins Jun, Fos and Myc are proteins that directly exert their effects on nuclear functions as transcription factors.

Inhibitors of Cellular Proliferation. The tumor suppressor oncogenes function to inhibit excessive cellular proliferation. The inactivation of these genes destroys their inhibitory activity, resulting in unregulated proliferation. The most common tumor suppressors are Rb, p53, p21 and p16. Other genes that may be employed according to the present invention include APC, DCC, NF-1, NF-2, WT-1, MEN-I, MEN-II, zacl, p73, VHL, C-CAM, MMAC1/PTEN, DBCCR-1, FCC, rsk-3, p27, p27/p16 fusions, and p21/p27 fusions.

Regulators of Programmed Cell Death. Apoptosis, or programmed cell death, is an essential process for normal embryonic development, maintaining homeostasis in adult tissues, and suppressing carcinogenesis (Kerr et al., 1972). The Bcl-2 family of proteins and ICE-like proteases have been demonstrated to be important regulators and effectors of apoptosis in other systems. The Bcl-2 protein, discovered in association with follicular lymphoma, plays a prominent role in controlling apoptosis and enhancing cell survival in response to diverse apoptotic stimuli (Bakhshi et al., 1985;

Cleary and Sklar, 1985; Cleary et al., 1986; Tsujimoto et al., 1985; Tsujimoto and Croce, 1986). The evolutionarily conserved Bcl-2 protein now is recognized to be a member of a family of related proteins, which can be categorized as death agonists or death antagonists.

Subsequent to its discovery, it was shown that Bcl-2 acts to suppress cell death triggered by a variety of stimuli. Also, it now is apparent that there is a family of Bcl-2 cell death regulatory proteins that share in common structural and sequence homologies. These different family members have been shown to either possess similar functions to Bcl-2 (e.g., BclxL, Bclw, Bcls, Mel-1, Al, Bfl-1) or counteract Bcl-2 function and promote cell death (e.g., Bax, Bak, Bik, Bim, Bid, Bad, Harakiri).

5. Surgery

Approximately 60% of persons with cancer will undergo surgery of some type, which includes preventative, diagnostic or staging, curative and palliative surgery. Curative surgery is a cancer treatment that may be used in conjunction with other therapies, such as the treatment of the present invention, chemotherapy, radiotherapy, hormonal therapy, gene therapy, immunotherapy and/or alternative therapies.

Curative surgery includes resection in which all or part of cancerous tissue is physically removed, excised, and/or destroyed. Tumor resection refers to physical removal of at least part of a tumor. In addition to tumor resection, treatment by surgery includes laser surgery, cryosurgery, electrosurgery, and microscopically controlled surgery (Mohs' surgery). It is further contemplated that the present invention may be used in conjunction with removal of superficial cancers, precancers, or incidental amounts of normal tissue.

Upon excision of part of all of cancerous cells, tissue, or tumor, a cavity may be formed in the body. Treatment may be accomplished by perfusion, direct injection or local application of the area with an additional anti-cancer therapy. Such treatment may be repeated, for example, every 1, 2, 3, 4, 5, 6, or 7 days, or every 1, 2, 3, 4, and 5 weeks or every 1, 2, 3, 4, 5, 6, 7, 8, 9, 10, 11, or 12 months. These treatments may be of varying dosages as well.

V. ANTIBODY CONJUGATES

Antibodies may be linked to at least one agent to form an antibody conjugate. In order to increase the efficacy of antibody molecules as diagnostic or therapeutic agents, it is conventional to link or covalently bind or complex at least one desired molecule or moiety. Such a molecule or moiety may be, but is not limited to, at least one effector or reporter molecule. Effector molecules comprise molecules having a desired activity, e.g., immunosuppression/anti-inflammation. Non-limiting examples of such molecules are set out above. Such molecules are optionally attached via cleavable linkers designed to allow the molecules to be released at or near the target site.

By contrast, a reporter molecule is defined as any moiety which may be detected using an assay. Non-limiting examples of reporter molecules which have been conjugated to antibodies include enzymes, radiolabels, haptens, fluorescent labels, phosphorescent molecules, chemiluminescent molecules, chromophores, photoaffinity molecules, colored particles or ligands, such as biotin.

Antibody conjugates are generally preferred for use as diagnostic agents. Antibody diagnostics generally fall within two classes, those for use in in vitro diagnostics, such as in a variety of immunoassays, and those for use in vivo diagnostic protocols, generally known as "antibody-directed imaging." Many appropriate imaging agents are known in the art, as are methods for their attachment to antibodies (see, for e.g., U.S. Pat. Nos. 5,021,236, 4,938,948, and 4,472,509). The imaging moieties used can be paramagnetic ions, radioactive isotopes, fluorochromes, NMR-detectable substances, and X-ray imaging agents.

In the case of paramagnetic ions, one might mention by way of example ions such as chromium (III), manganese (II), iron (III), iron (II), cobalt (II), nickel (II), copper (II), neodymium (III), samarium (III), ytterbium (III), gadolinium (III), vanadium (II), terbium (III), dysprosium (III), holmium (III) and/or erbium (III), with gadolinium being particularly preferred. Ions useful in other contexts, such as X-ray imaging, include but are not limited to lanthanum (III), gold (III), lead (II), and especially bismuth (III).

In the case of radioactive isotopes for therapeutic and/or diagnostic application, one might mention astatine$^{211}$, $^{14}$carbon, $^{51}$chromium, $^{36}$chlorine, $^{57}$cobalt, $^{58}$cobalt, copper$^{67}$, $^{152}$Eu, gallium$^{67}$, $^{3}$hydrogen, iodine$^{123}$, iodine$^{125}$, iodine$^{131}$, indium$^{111}$, $^{59}$iron, $^{32}$phosphorus, rhenium$^{186}$, rhenium$^{188}$, $^{75}$selenium, $^{35}$sulphur, technicium$^{99m}$ and/or yttrium$^{90}$ is often being preferred for use in certain embodiments, and technicium$^{99m}$ and/or indium$^{11}$ are also often preferred due to their low energy and suitability for long range detection. Radioactively labeled monoclonal antibodies may be produced according to well-known methods in the art. For instance, monoclonal antibodies can be iodinated by contact with sodium and/or potassium iodide and a chemical oxidizing agent such as sodium hypochlorite, or an enzymatic oxidizing agent, such as lactoperoxidase. Monoclonal antibodies may be labeled with technetium99m by ligand exchange process, for example, by reducing pertechnate with stannous solution, chelating the reduced technetium onto a Sephadex column and applying the antibody to this column. Alternatively, direct labeling techniques may be used, e.g., by incubating pertechnate, a reducing agent such as SNCh, a buffer solution such as sodium-potassium phthalate solution, and the antibody. Intermediary functional groups are often used to bind radioisotopes to antibody and exist as metallic ions are diethylenetriaminepentaacetic acid (DTPA) or ethylene diaminetetracetic acid (EDTA).

Among the fluorescent labels contemplated for use as conjugates include Alexa 350, Alexa 430, AMCA, BODIPY 630/650, BODIPY 650/665, BODIPYFL, BODIPY-R6G, BODIPY-TMR, BODIPY-TRX, Cascade Blue, Cy3, Cy5,6-FAM, Fluorescein Isothiocyanate, HEX, 6-JOE, Oregon Green 488, Oregon Green 500, Oregon Green 514, Pacific Blue, REG, Rhodamine Green, Rhodamine Red, Renographin, ROX, TAMRA, TET, Tetramethylrhodamine, and/or Texas Red.

Another type of antibody conjugates contemplated are those intended primarily for use in vitro, where the antibody is linked to a secondary binding ligand and/or to an enzyme (an enzyme tag) that will generate a colored product upon contact with a chromogenic substrate. Examples of suitable enzymes include urease, alkaline phosphatase, (horseradish) hydrogen peroxidase or glucose oxidase. Preferred secondary binding ligands are biotin and avidin and streptavidin compounds. The use of such labels is well known to those of skill in the art and are described, for example, in U.S. Pat. Nos. 3,817,837, 3,850,752, 3,939,350, 3,996,345, 4,277, 437, 4,275,149 and 4,366,241.

Yet another known method of site-specific attachment of molecules to antibodies comprises the reaction of antibodies with hapten-based affinity labels. Essentially, hapten-based affinity labels react with amino acids in the antigen binding site, thereby destroying this site and blocking specific antigen reaction. However, this may not be advantageous since it results in loss of antigen binding by the antibody conjugate.

Molecules containing azido groups may also be used to form covalent bonds to proteins through reactive nitrene intermediates that are generated by low intensity ultraviolet light (Potter and Haley, 1983). In particular, 2- and 8-azido analogues of purine nucleotides have been used as site-directed photoprobes to identify nucleotide binding proteins in crude cell extracts (Owens & Haley, 1987; Atherton et al., 1985). The 2- and 8-azido nucleotides have also been used to map nucleotide binding domains of purified proteins (Khatoon et al., 1989; King et al., 1989; Dholakia et al., 1989) and may be used as antibody binding agents.

Several methods are known in the art for the attachment or conjugation of an antibody to its conjugate moiety. Some attachment methods involve the use of a metal chelate complex employing, for example, an organic chelating agent such as a diethylenetriaminepentaacetic acid anhydride (DTPA); ethylenetriaminetetraacetic acid; N-chloro-p-toluenesulfonamide; and/or tetrachloro-3a-6a-diphenylglycouril-3 attached to the antibody (U.S. Pat. Nos. 4,472,509 and 4,938,948). Monoclonal antibodies may also be reacted with an enzyme in the presence of a coupling agent such as glutaraldehyde or periodate. Conjugates with fluorescein markers are prepared in the presence of these coupling agents or by reaction with an isothiocyanate. In U.S. Pat. No. 4,938,948, imaging of breast tumors is achieved using monoclonal antibodies and the detectable imaging moieties are bound to the antibody using linkers such as methyl-p-hydroxybenzimidate or N-succinimidy 1-3-(4-hydroxypheny1)propionate.

In other embodiments, derivatization of immunoglobulins by selectively introducing sulfhydryl groups in the Fe region of an immunoglobulin, using reaction conditions that do not alter the antibody combining site are contemplated. Antibody conjugates produced according to this methodology are disclosed to exhibit improved longevity, specificity and sensitivity (U.S. Pat. No. 5,196,066, incorporated herein by reference). Site-specific attachment of effector or reporter molecules, wherein the reporter or effector molecule is conjugated to a carbohydrate residue in the Fe region have also been disclosed in the literature (O'Shannessy et al., 1987). This approach has been reported to produce diagnostically and therapeutically promising antibodies which are currently in clinical evaluation.

VI. IMMUNODETECTION METHODS

In still further embodiments, there are immunodetection methods for binding, purifying, removing, quantifying and otherwise generally detecting PD-L1 or PD-L2 and their associated antigens. Some immunodetection methods include enzyme linked immunosorbent assay (ELISA), radioimmunoassay (RIA), immunoradiometric assay, fluoroimmunoassay, chemiluminescent assay, bioluminescent assay, and Western blot to mention a few. In particular, a competitive assay for the detection and quantitation of PD-L1 and PD-L2 antibodies also is provided. The steps of various useful immunodetection methods have been described in the scientific literature, such as, e.g., Doolittle and BenZeev (1999), Gulbis and Galand (1993), De Jager et al. (1993), and Nakamura et al. (1987). In general, the immunobinding methods include obtaining a sample and contacting the sample with a first antibody in accordance with embodiments discussed herein, as the case may be, under conditions effective to allow the formation of immunocomplexes.

Contacting the chosen biological sample with the antibody under effective conditions and for a period of time sufficient to allow the formation of immune complexes (primary immune complexes) is generally a matter of simply adding the antibody composition to the sample and incubating the mixture for a period of time long enough for the antibodies to form immune complexes with, i.e., to bind to PD-L1 and PD-L2 present. After this time, the sample-antibody composition, such as a tissue section, ELISA plate, dot blot or Western blot, will generally be washed to remove any nonspecifically bound antibody species, allowing only those antibodies specifically bound within the primary immune complexes to be detected.

In general, the detection of immunocomplex formation is well known in the art and may be achieved through the application of numerous approaches. These methods are generally based upon the detection of a label or marker, such as any of those radioactive, fluorescent, biological and enzymatic tags. Patents concerning the use of such labels include U.S. Pat. Nos. 3,817,837, 3,850,752, 3,939,350, 3,996,345, 4,277,437, 4,275,149 and 4,366,241. Of course, one may find additional advantages through the use of a secondary binding ligand such as a second antibody and/or a biotin/avidin ligand binding arrangement, as is known in the art.

The antibody employed in the detection may itself be linked to a detectable label, wherein one would then simply detect this label, thereby allowing the amount of the primary immune complexes in the composition to be determined. Alternatively, the first antibody that becomes bound within the primary immune complexes may be detected by means of a second binding ligand that has binding affinity for the antibody. In these cases, the second binding ligand may be linked to a detectable label. The second binding ligand is itself often an antibody, which may thus be termed a "secondary" antibody. The primary immune complexes are contacted with the labeled, secondary binding ligand, or antibody, under effective conditions and for a period of time sufficient to allow the formation of secondary immune complexes. The secondary immune complexes are then generally washed to remove any non-specifically bound labeled secondary antibodies or ligands, and the remaining label in the secondary immune complexes is then detected.

Further methods include the detection of primary immune complexes by a two-step approach. A second binding ligand, such as an antibody that has binding affinity for the antibody, is used to form secondary immune complexes, as described above. After washing, the secondary immune complexes are contacted with a third binding ligand or antibody that has binding affinity for the second antibody, again under effective conditions and for a period of time sufficient to allow the formation of immune complexes (tertiary immune complexes). The third ligand or antibody is linked to a detectable label, allowing detection of the tertiary immune complexes thus formed. This system may provide for signal amplification if this is desired.

One method of immunodetection uses two different antibodies. A first biotinylated antibody is used to detect the target antigen, and a second antibody is then used to detect the biotin attached to the complexed biotin. In that method, the sample to be tested is first incubated in a solution containing the first step antibody. If the target antigen is present, some of the antibody binds to the antigen to form a biotinylated antibody/antigen complex. The antibody/antigen complex is then amplified by incubation in successive solutions of streptavidin (or avidin), biotinylated DNA, and/or complementary biotinylated DNA, with each step adding additional biotin sites to the antibody/antigen complex. The amplification steps are repeated until a suitable level of amplification is achieved, at which point the sample is incubated in a solution containing the second step antibody against biotin. This second step antibody is labeled, as for example with an enzyme that can be used to detect the presence of the antibody/antigen complex by histoenzymology using a chromogen substrate. With suitable amplification, a conjugate can be produced which is macroscopically visible.

Another known method of immunodetection takes advantage of the immuno-PCR (Polymerase Chain Reaction) methodology. The PCR method is similar to the Cantor method up to the incubation with biotinylated DNA, however, instead of using multiple rounds of streptavidin and biotinylated DNA incubation, the DNA/biotin/streptavidin/antibody complex is washed out with a low pH or high salt buffer that releases the antibody. The resulting wash solution is then used to carry out a PCR reaction with suitable primers with appropriate controls. At least in theory, the enormous amplification capability and specificity of PCR can be utilized to detect a single antigen molecule.

A. ELISAs

Immunoassays, in their most simple sense, are binding assays. Certain preferred immunoassays are the various types of enzyme linked immunosorbent assays (ELISAs) and radioimmunoassays (RIA) known in the art. Immunohistochemical detection using tissue sections is also particularly useful. However, it will be readily appreciated that detection is not limited to such techniques, and western blotting, dot blotting, FACS analyses, and the like may also be used.

In one exemplary ELISA, the antibodies of the disclosure are immobilized onto a selected surface exhibiting protein affinity, such as a well in a polystyrene microtiter plate. Then, a test composition suspected of containing PD-L1 and/or PD-L2 is added to the wells. After binding and washing to remove non-specifically bound immune complexes, the bound antigen may be detected. Detection may be achieved by the addition of another bispecific antibody directed to PD-L1 and PD-L2 linked to a detectable label, or by an anti-PD-L1 or anti-PD-L2 antibody that is linked to a detectable label. This type of ELISA is a simple "sandwich ELISA." Detection may also be achieved by the addition of a second bispecific antibody to PD-L1 and PD-2, or an anti-PD-L1 or anti-PD-L2 antibody, followed by the addition of a third antibody that has binding affinity for the second antibody, with the third antibody being linked to a detectable label.

In another exemplary ELISA, the samples suspected of containing the PD-L1 and/or PD-L2 antigen are immobilized onto the well surface and then contacted with a bispecific anti-PD-L1 and anti-PD-L2 antibody. After binding and washing to remove non-specifically bound immune complexes, the bound bispecific anti-PD-L1 and anti-PD-L2 antibodies are detected. Where the initial bispecific anti-PD-L1 and anti-PDL2 antibodies are linked to a detectable label, the immune complexes may be detected directly. Again, the immune complexes may be detected using a second antibody that has binding affinity for the first bispecific anti-PD-L1 and anti-PD-L2 antibody, with the second antibody being linked to a detectable label.

Irrespective of the format employed, ELISAs have certain features in common, such as coating, incubating and binding, washing to remove non-specifically bound species, and detecting the bound immune complexes. These are described below.

In coating a plate with either antigen or antibody, one will generally incubate the wells of the plate with a solution of the antigen or antibody, either overnight or for a specified period of hours. The wells of the plate will then be washed to remove incompletely adsorbed material. Any remaining available surfaces of the wells are then "coated" with a nonspecific protein that is antigenically neutral with regard to the test antisera. These include bovine serum albumin (BSA), casein or solutions of milk powder. The coating allows for blocking of nonspecific adsorption sites on the immobilizing surface and thus reduces the background caused by nonspecific binding of antisera onto the surface.

In ELISAs, it is probably more customary to use a secondary or tertiary detection means rather than a direct procedure. Thus, after binding of a protein or antibody to the well, coating with a non-reactive material to reduce background, and washing to remove unbound material, the immobilizing surface is contacted with the biological sample to be tested under conditions effective to allow immune complex (antigen/antibody) formation. Detection of the immune complex then requires a labeled secondary binding ligand or antibody, and a secondary binding ligand or antibody in conjunction with a labeled tertiary antibody or a third binding ligand.

"Under conditions effective to allow immune complex (antigen/antibody) formation" means that the conditions preferably include diluting the antigens and/or antibodies with solutions such as BSA, bovine gamma globulin (BGG) or phosphate buffered saline (PBS)/Tween. These added agents also tend to assist in the reduction of nonspecific background.

The "suitable" conditions also mean that the incubation is at a temperature or for a period of time sufficient to allow effective binding. Incubation steps are typically from about 1 to about 2 to 4 hours, at temperatures preferably on the order of 25° C. to 27° C., or may be overnight at about 4° C.

Following all incubation steps in an ELISA, the contacted surface is washed so as to remove non-complexed material. A preferred washing procedure includes washing with a solution such as PBS/Tween, or borate buffer. Following the formation of specific immune complexes between the test sample and the originally bound material, and subsequent washing, the occurrence of even minute amounts of immune complexes may be determined.

To provide a detecting means, the second or third antibody will have an associated label to allow detection. Preferably, this will be an enzyme that will generate color development upon incubating with an appropriate chromogenic substrate. Thus, for example, one will desire to contact or incubate the first and second immune complex with a urease, glucose oxidase, alkaline phosphatase or hydrogen peroxidase-conjugated antibody for a period of time and under conditions that favor the development of further immune complex formation (e.g., incubation for 2 hours at room temperature in a PBS-containing solution such as PBS-Tween).

After incubation with the labeled antibody, and subsequent to washing to remove unbound material, the amount of label is quantified, e.g., by incubation with a chromogenic substrate such as urea, or bromocresol purple, or 2,2'-azino-di-(3-ethylbenzthiazoline-6-sulfonic acid (ABTS), or H202, in the case of peroxidase as the enzyme label. Quantification is then achieved by measuring the degree of color generated, e.g., using a visible spectra spectrophotometer.

B. Western Blot

The Western blot (alternatively, protein immunoblot) is an analytical technique used to detect specific proteins in a given sample of tissue homogenate or extract. It uses gel electrophoresis to separate native or denatured proteins by the length of the polypeptide (denaturing conditions) or by the 3-D structure of the protein (native/nondenaturing conditions). The proteins are then transferred to a membrane (typically nitrocellulose or PVDF), where they are probed (detected) using antibodies specific to the target protein.

Samples may be taken from whole tissue or from cell culture. In most cases, solid tissues are first broken down mechanically using a blender (for larger sample volumes), using a homogenizer (smaller volumes), or by sonication. Cells may also be broken open by one of the above mechanical methods. However, it should be noted that bacteria, virus or environmental samples can be the source of protein and thus Western blotting is not restricted to cellular studies only. Assorted detergents, salts, and buffers may be employed to encourage lysis of cells and to solubilize proteins. Protease and phosphatase inhibitors are often added to prevent the digestion of the sample by its own enzymes. Tissue preparation is often done at cold temperatures to avoid protein denaturing.

The proteins of the sample are separated using gel electrophoresis. Separation of proteins may be by isoelectric point (pl), molecular weight, electric charge, or a combination of these factors. The nature of the separation depends on the treatment of the sample and the nature of the gel. This is a very useful way to determine a protein. It is also possible to use a two-dimensional (2-D) gel which spreads the proteins from a single sample out in two dimensions. Proteins are separated according to isoelectric point (pH at which they have neutral net charge) in the first dimension, and according to their molecular weight in the second dimension.

In order to make the proteins accessible to antibody detection, they are moved from within the gel onto a membrane made of nitrocellulose or polyvinylidene difluoride (PVDF). The membrane is placed on top of the gel, and a stack of filter papers placed on top of that. The entire stack is placed in a buffer solution which moves up the paper by capillary action, bringing the proteins with it. Another method for transferring the proteins is called electroblotting and uses an electric current to pull proteins from the gel into the PVDF or nitrocellulose membrane. The proteins move from within the gel onto the membrane while maintaining the organization they had within the gel. As a result of this blotting process, the proteins are exposed on a thin surface layer for detection (see below). Both varieties of membrane are chosen for their non-specific protein binding properties (i.e., binds all proteins equally well). Protein binding is based upon hydrophobic interactions, as well as charged interactions between the membrane and protein. Nitrocellulose membranes are cheaper than PVDF, but are far more fragile and do not stand up well to repeated probing. The uniformity and overall effectiveness of transfer of protein from the gel to the membrane can be checked by staining the membrane with Coomassie Brilliant Blue or Ponceau S dyes. Once transferred, proteins are detected using labeled primary antibodies, or unlabeled primary antibodies followed by indirect detection using labeled protein A or secondary labeled antibodies binding to the Fe region of the primary antibodies.

C. Immunohistochemistry

The antibodies may also be used in conjunction with both fresh-frozen and/or formalin-fixed, paraffin-embedded tissue blocks prepared for study by immunohistochemistry (IHC). The method of preparing tissue blocks from these particulate specimens has been successfully used in previous IHC studies of various prognostic factors, and is well known to those of skill in the art (Brown et al., 1990; Abbondanzo et al., 1990; Allred et al., 1990).

Briefly, frozen-sections may be prepared by rehydrating 50 ng of frozen "pulverized" tissue at room temperature in phosphate buffered saline (PBS) in small plastic capsules; pelleting the particles by centrifugation; resuspending them in a viscous embedding medium (OCT); inverting the capsule and/or pelleting again by centrifugation; snap-freezing in −70° C. isopentane; cutting the plastic capsule and/or removing the frozen cylinder of tissue; securing the tissue cylinder on a cryostat microtome chuck; and/or cutting 25-50 serial sections from the capsule. Alternatively, whole frozen tissue samples may be used for serial section cuttings.

Permanent-sections may be prepared by a similar method involving rehydration of the 50 mg sample in a plastic microfuge tube; pelleting; resuspending in 10% formalin for 4 hours fixation; washing/pelleting; resuspending in warm 2.5% agar; pelleting; cooling in ice water to harden the agar; removing the tissue/agar block from the tube; infiltrating and/or embedding the block in paraffin; and/or cutting up to 50 serial permanent sections. Again, whole tissue samples may be substituted.

D. Immunodetection Kits

In still further embodiments, there are immunodetection kits for use with the immunodetection methods described above. The immunodetection kits will thus comprise, in suitable container means, a first bispecific antibody that binds to PD-L1 and/or PD-L2 antigens, and optionally an immunodetection reagent.

In certain embodiments, the bispecific antibody to PD-L1 and PD-L2 may be pre-bound to a solid support, such as a column matrix and/or well of a microtiter plate. The immunodetection reagents of the kit may take any one of a variety of forms, including those detectable labels that are associated with or linked to the given antibody. Detectable labels that are associated with or attached to a secondary binding ligand are also contemplated. Exemplary secondary ligands are those secondary antibodies that have binding affinity for the first antibody.

Further suitable immunodetection reagents for use in the present kits include the two-component reagent that comprises a secondary antibody that has binding affinity for the first antibody, along with a third antibody that has binding affinity for the second antibody, the third antibody being linked to a detectable label. As noted above, a number of exemplary labels are known in the art and all such labels may be employed in connection with embodiments discussed herein.

The kits may further comprise a suitably aliquoted composition of the PD-L1 and PD-L2 antigens, whether labeled or unlabeled, as may be used to prepare a standard curve for a detection assay. The kits may contain antibody-label conjugates either in fully conjugated form, in the form of intermediates, or as separate moieties to be conjugated by the user of the kit. The components of the kits may be packaged either in aqueous media or in lyophilized form.

The container means of the kits will generally include at least one vial, test tube, flask, bottle, syringe or other container means, into which the antibody may be placed, or preferably, suitably aliquoted. The kits will also include a means for containing the antibody, antigen, and any other reagent containers in close confinement for commercial sale. Such containers may include injection or blow-molded plastic containers into which the desired vials are retained.

VII. EXAMPLES

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1—Materials and Methods

Antibody Characterization. Antibody candidates generated from yeast-surface display screening were tested for the capacity to bind to PD-L1 or PD-L2. To generate affinity KD to human PD-L1 and PD-L2, candidate monoclonal Abs were loaded onto Anti-Human Fc Capture (AHC) Biosensors at 100 nM (15 µg/mL), and human PD-L1 or PD-L2 protein association and dissociation was tested in dilution series from 30-0.37 nM. The binding and release of the analyte (PD-L1 or PD-L2) are recorded by the Octet instrument in real time and then used to calculate the KD, Kon, and Kdis; results are derived from 2:1 Global Fit Modeling with reference well subtraction. To generate affinity KD to murine PD-L1 and PD-L2, candidate antibodies were covalently immobilized onto activated Amine Reactive 2nd Generation (AR2G) Biosensors (quenched with 1 M ethanolamine pH 8.5 after protein loading) at 100 nM (15 µg/mL), and mouse PD-L1 or PD-L2 protein association and dissociation was tested in dilution series from 300-1 nM. The binding and release of the analyte are recorded by the Octet instrument in real time and then used to calculate the KD, Kon, and Kdis; results are derived from 2:1 Global Fit Modeling with reference well subtraction.

Dual-PD-L1/PD-L2 specific antibody activity in mixed lymphocyte reactions. CD14+ monocytes were isolated from peripheral blood mononuclear cells using CD14 microbeads. Cells were seeded at 1 million/ml in and stimulated with IL-4 and GM-CSF in 10% FCS/RPMI/P/S cell culture medium. Cells were cultured for 7 days to differentiate into immature dendritic cells (IDCs) and varying concentrations of PD-L1, both PD-L1 and PD-L2, DiPDL or commercial antibodies were added. IDCs were then used to stimulate CD4+ T cells at a ratio of 10:1 CD4:IDCs. IFN-γ was assayed by ELISA following the protocols provided by R&D systems.

Antibody activity against syngeneic mouse colorectal cancer. $1 \times 10^5$ CT26 or CT26-PDL2 colorectal cancer cells are implanted subcutaneously on the right flank of female BALB/c mice. On days 3, 6, 9, 12, and 15, mice receive PD-L1/PD-L2 antibody (250ug), control antibodies (e.g. anti-PD-1) or vehicle intra-peritoneally. Tumor growth is followed with caliper measurements and mice are scored as no longer surviving when they die or tumor volume exceeds 1000 mm3.

Antibody activity against BFTC909 renal cell carcinoma in humanized mice. $5 \times 10^6$ BFTC909 renal cell cancer cells are implanted subcutaneously on the right flank of human CD34+ stem cell engrafted huNOG-ExL mice. When tumors reach >50 mm³, mice receive PD-L1/PD-L2 antibody (250 µg), control antibodies (e.g. anti-PD-1) or vehicle intra-peritoneally twice a week for three weeks. Tumor growth is followed with caliper measurements and mice are scored as no longer surviving when they die or tumor volume exceeds 1000 mm³.

Measurement of human insulin receptor binding. $2 \times 10^6$ CHO-K cells or CHO-K-human Insulin Receptor (CHO-INSR) cells are placed into wells of a 96 well round-bottom tissue culture plate and pelleted by centrifugation at 2000 RPM for 2 minutes. The pellets are resuspended in 100 µl of flow cytometry staining buffer with a range of concentrations of PD-L1/PD-L2 bispecific antibody (typically, 0.1, 1, 10 µg/mL) and incubated at 4 degrees Celsius for 30 minutes-1 hour. Cells are then pelleted and resuspended with a 1:300 dilution of anti-human IgG PE secondary antibody. After another 30-minute incubation, cells are pelleted a final time and resuspended in 100 µl of flow cytometry buffer. Resuspended cells are run on a BD LSR II flow cytometer to assess intensity of PE fluorescence in the CHO-INSR versus CHO-K cells to assess amount of binding to human Insulin Receptor.

Example 2—Results

Generation of PD-L1/PD-L2 dual-specific antibodies without Insulin Receptor cross-reactivity. PD-L1 and PD-L2 heavy and light chains from several rounds of Adimab® selection had generated the high affinity, PD-L1/PD-L2 dual-specific antibody ADI-37464. Despite the potent anti-tumor activity of this antibody, it was found to have high affinity for the human Insulin Receptor (INSR) as well making it unsuitable for clinical use. FIG. 1 shows that five new clones (38000-38004) were generated through targeted point mutation of the light chain complementarity determining regions (CDR) with the goal of removing Insulin Receptor binding but preserving high PD-L1/PD-L2 dual affinity. Surprisingly, such modifications resulted in very little appreciable difference in binding affinities between the parent clone and the modified antibodies. Three of these derivates (38002, 38003, 38004) showed significantly reduced INSR binding with retained PD-L1/PD-L2 dual affinity and were advanced for further study.

Affinity measurement of 38000 series PD-L1/PD-L2 antibodies. Using Octet and Biocore, the affinity for PD-L1 and PD-L2 for the 38000 series of antibodies was measured relative to their parental antibody ADI-37464 (FIG. 2). By all measures, 38002 demonstrated PD-L1 and PD-L2 binding affinities that were not significantly different than 37464.

Figures 4, 5:
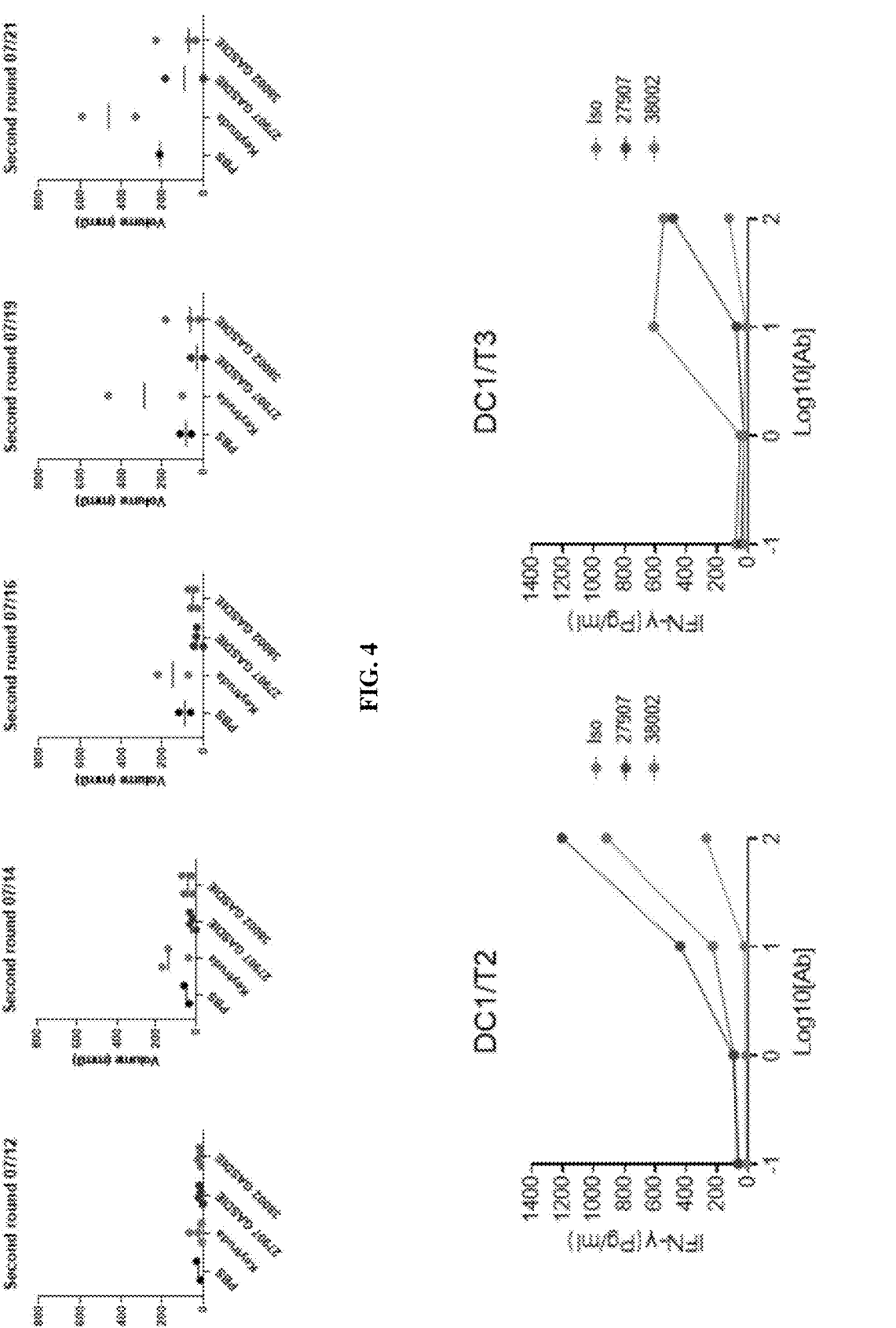
FIG. 4 illustrates treatment of BFTC-909 Renal Cell Carcinoma in Humanized Mice. BFTC-909 xenograft tumors were implanted in huNOG-ExL CD34+ stem cell humanized mice and treated once tumors reached 50 mm$^3$ bi-weekly at 10 mg/kg with the antibody shown.
FIG. 5 illustrates 38002 PD-L1/PD-L2 antibody enhances IFN-gamma secretion in human peripheral blood mixed lymphocyte reactions. In vitro generated dendritic cells from one donor (Donor 1) were co-cultured with T cells from two other donors (Donor 2 or 3) and IFN-gamma secretion was measured by ELISA after 72 hours of co-culture.

Treatment of CT26 parental and CT26-PD-L2 tumors with 38000 series PD-L1/PD-L2 dual-specific antibodies. In the parental CT26 syngeneic model of colorectal cancer, 38002 showed equivalent therapeutic activity to the parental antibody 37464 (FIG. 3A). In the high PD-L2 overexpressing CT26-PD-L2 model, 38002 showed equivalent tumor growth inhibition to the parental 37464 clone (FIG. 3B). Both 38002 and 37464 were capable of curing animals of CT26-PD-L2, and, although 37464 cured a larger fraction, the difference between 38002 and 37464 in this experiment were not statistically significant. In a second CT26 parental experiment, 38002 showed great tumor growth inhibition that PD-1 blockade and was again statistically equivalent to the parental PD-L1/PD-L2 dual-specific antibody 37464 (FIG. 4).

Treatment of BFTC-909 Renal Cell Carcinoma in Humanized Mice. In treating human BFTC909 renal cell carcinoma tumors in bone marrow stem cell humanized huNOG-ExL mice, 38002 showed the highest reduction in tumor growth over the 10 days of treatment compared to Keytruda or another PD-L1/PD-L2 dual-specific clone 27907 (FIG. 5).

Human mixed lymphocyte reactions (MLR). In two separate donor mixed lymphocyte reaction pairs, the addition of the PD-L1/PD-L2 dual-specific antibody 38002 significantly enhanced release of Interferon gamma to equivalent or greater levels compared to the PD-L1/PD-L2 dual-specific antibody 27907 (FIG. 5).

Figure 6:
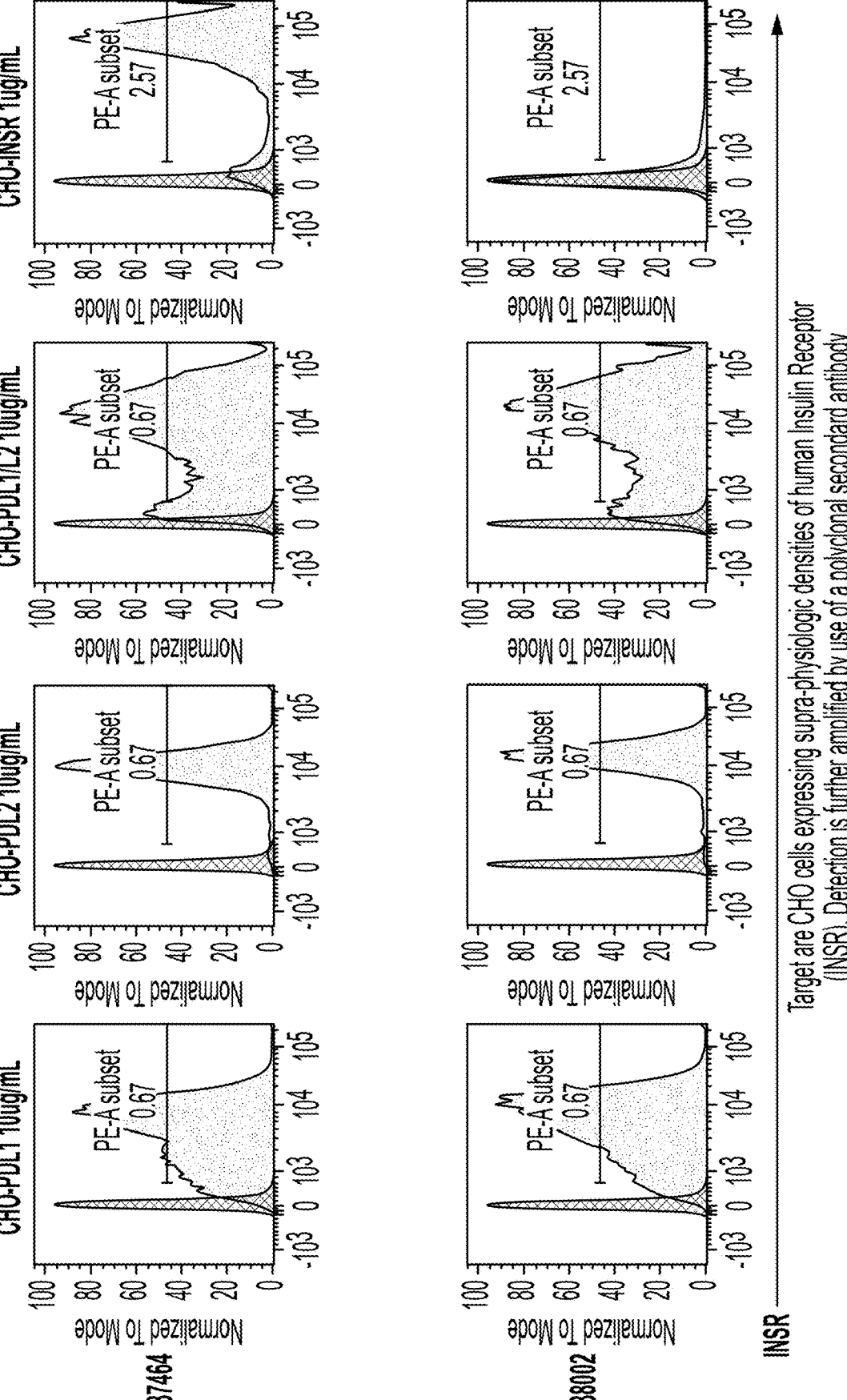
FIG. 6 illustrates that 38002 and 38004 have no binding to human Insulin Receptor at physiologic concentrations. CHO cells expressing high concentrations of Insulin Receptor were stained with the indicated PD-L1/PD-L2 antibody and a secondary anti-human PE conjugate. Amount of binding was measured by flow cytometry on a BD LSRII.

Measurement of off-target Insulin Receptor binding. While 37464 and all 38000 antibodies showed high binding by flow cytometry to PD-L1, PD-L2 and dual PD-L1 and PD-L2 CHO cells, 37464 also showed significant binding to CHO cells overexpressing INSR at 1 µg/mL. The two derivative clones 38002 and 38004, in contrast, show no detectable binding to INSR at 1 µg/mL as shown in FIG. 6. This lack of INSR binding at concentrations achievable in vivo is a critical feature of the 38000 series of PD-L1/PD-L2 antibodies which separates them from the prior 37464 antibody and renders them suitable for therapeutic use in patients.

Figure 10:
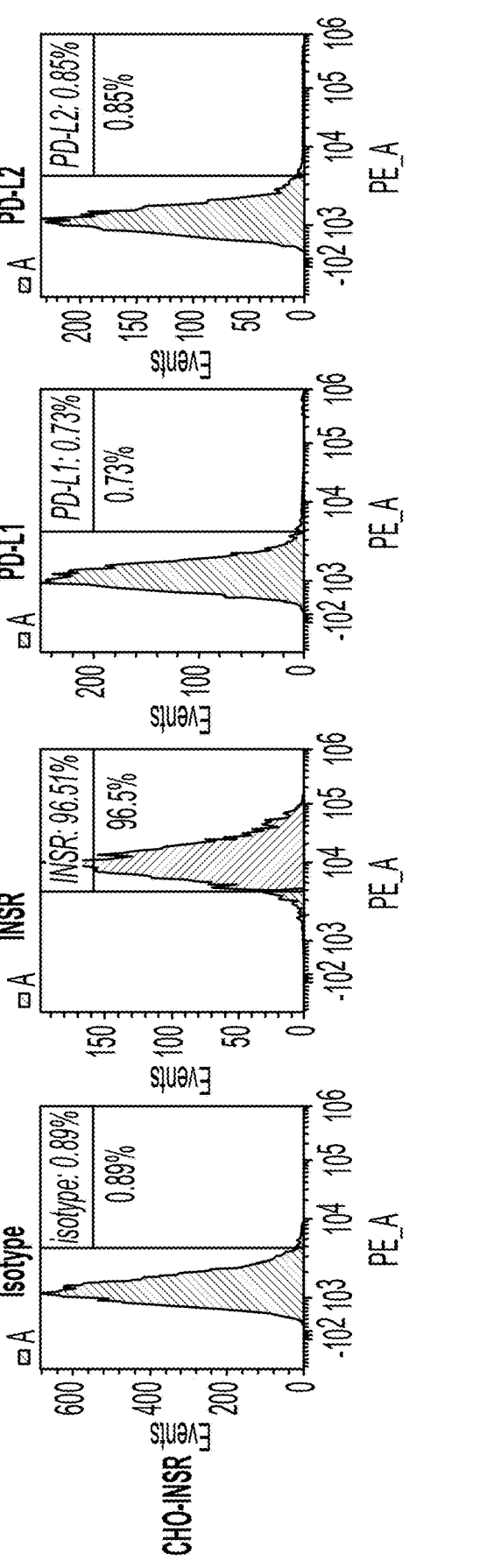
FIG. 10 illustrates histogram plots showing staining of PE-labeled isotype, anti-human INSR, anti-human PD-L1, and anti-human PD-L2 on CHO-INSR cells used in the study. The gate was set on the isotype control sample. PE expression is displayed on the x-axis.

Example 3—Analysis of Binding, ADCC and ADCP Activities for 38002 Versus 37464 Against Insulin Receptor on CHO Cells INSR, PD-L1 and PD-L2 expression on CHO-INSR cells. The cells used in this example, Chinese hamster ovary (CHO) cells expressing the human insulin receptor (CHO-INSR), were acquired from ATCC (CHO INSR 1284-CRL-3307|ATCC). Cells were first characterized by flow cytometry for expression of INSR, PD-L1, and PD-L2. The engineered CHO cells showed high expression of INSR (>96%), as expected, and no expression of PD-L1 or PD-L2 (FIG. 10). INSR+ CHO cells were incubated with PE-tagged antibodies against INSR, PD-L1, PD-L2 a control. Fluorescence was measured by flow cytometry.

Figure 11:
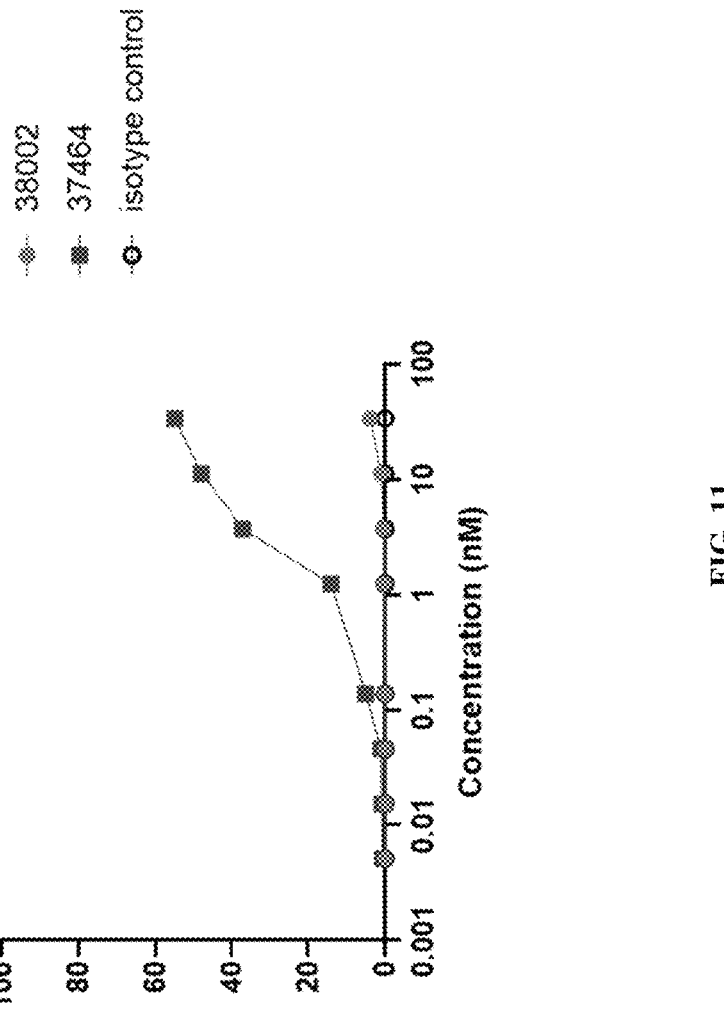
FIG. 11 illustrates results of INSR+ CHO cells incubated with serial dilutions of 38002 (circles), 37464 (squares) or a control (open circle) antibody. Fluorescence, measured by flow cytometry. Mean±SDM (n=2) is displayed for each concentration of each antibody. A dose range of 33.333-0.00511 nM was tested against INSR+ CHO cells.

Evaluation of binding to INSR on CHO cells. The ability of the 38002 and 37464 antibodies to bind to live cells expressing human INSR was evaluated through the use of flow cytometry. INSR-CHO cells were incubated with serial dilutions of 38002, 37464 or an isotype control antibody followed by 4 washes and incubation with Goat anti-Human IgG (H+L) secondary antibody, Alexa Fluor 555. Fluorescence was measured by flow cytometry. Data shows binding at high concentrations of 37464 but no binding of 38002 to INSR+ cells, when compared to isotype-control (FIG. 11).

Figure 12A:
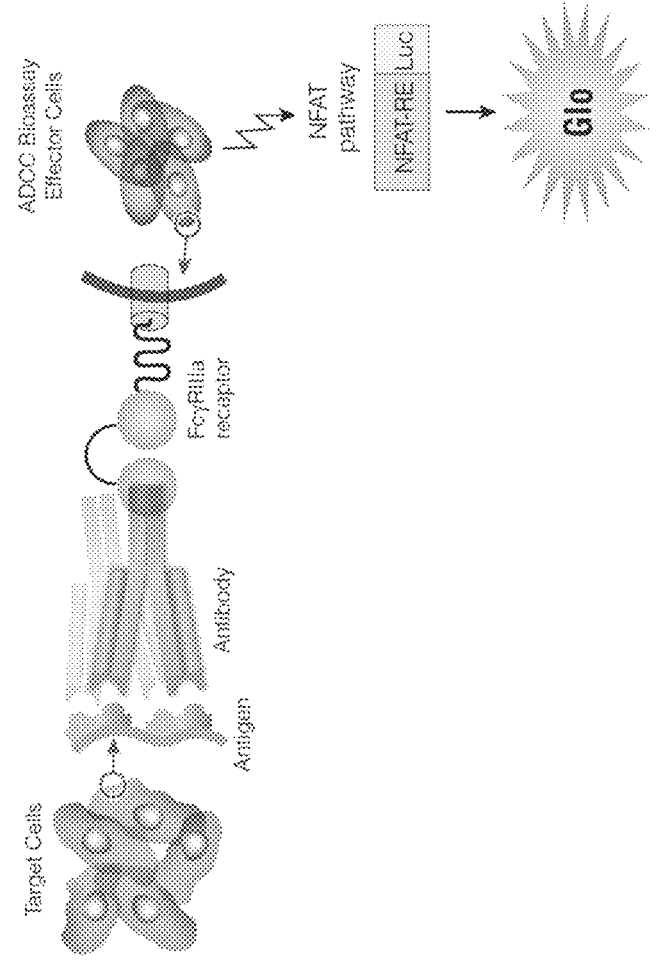
FIG. 12A illustrates a representation of the antibody dependent cellular cytotoxicity reporter bioassay (ADCC, Promega, 2020).
Figure 12B:
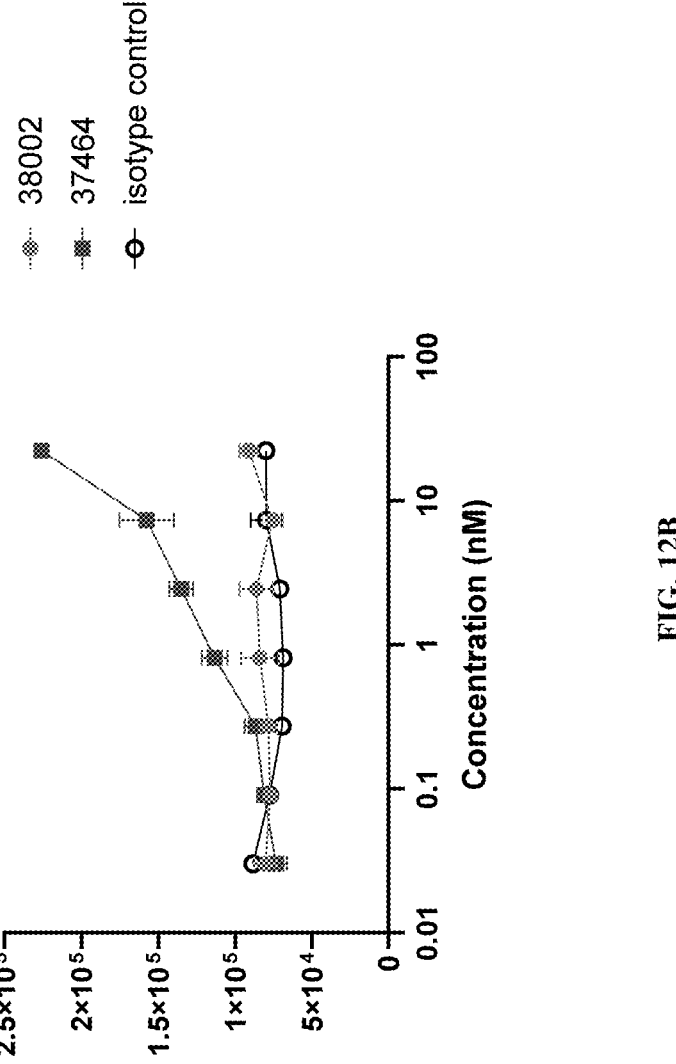
FIG. 12B illustrates ADCC (antibody dependent cellular cytotoxicity reporter bioassay (Promega, 2020)) activity of 38002 and 37464 against CHO-INSR cells. The concentration of 38002, 37464, or IgG isotype is displayed on the x-axis and luminescence activity in displayed on the y-axis. Mean±SDM (n=2) is displayed for each concentration of each antibody. A dose range of 22.22-0.0302 nM was tested against INSR+ CHO cells.

ADCC activity. To test the ADCC potential of 38002 and 37464 against INSR-expressing target cells, a reporter cell assay with Jurkat cells engineered to express the FcγRIIIa receptor with an NFAT response element that drives luciferase expression was used (FIG. 12A). The 38002 and 37464 antibodies were incubated with INSR-CHO target cells expressing INSR but not PD-L1 or PD-L2. Antibody 38002 showed no activity against INSR expressing target cells while antibody 37464 showed activity (FIG. 12B).

Figure 13A:
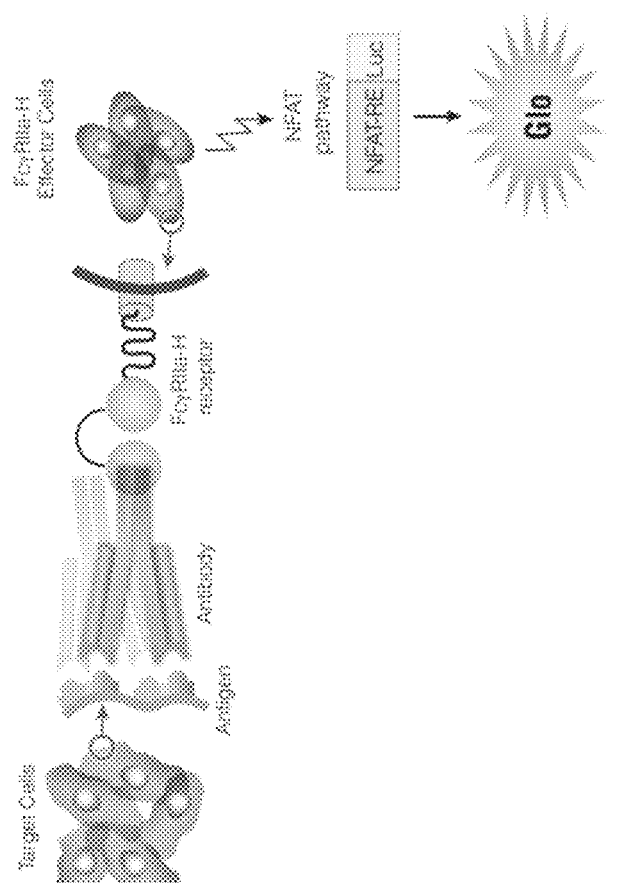
FIG. 13A illustrates a representation of the antibody dependent cellular phagocytosis reporter bioassay (ADCP, Promega, 2016).
Figure 13B:
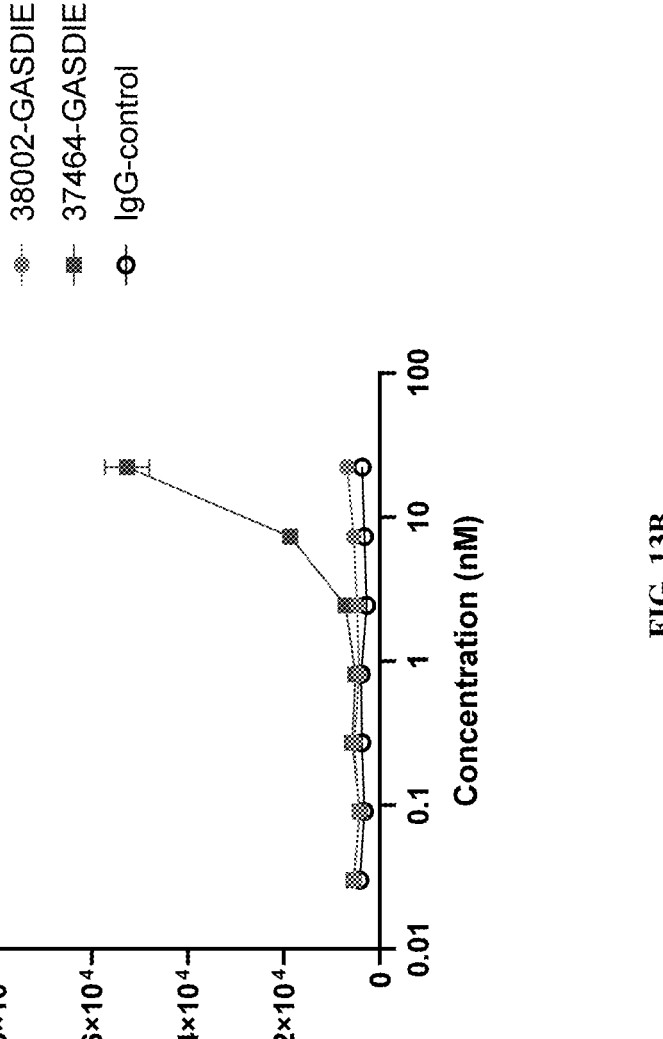
FIG. 13B illustrates ADCP activity of 38002 and 37464 against CHO-INSR cells. The concentration of 38002, 37464, or IgG isotype is displayed on the x-axis and luminescence activity in displayed on the y-axis. Mean±SD (n=2) is displayed for each concentration of each antibody. A dose range of 22.22-0.0302 nM was tested against INSR+ CHO cells.

ADCP activity. To test the ADCP activity of 38002, a reporter cell assay with Jurkat cells engineered to express the FcγRIIa receptor with an NFAT response element that drives luciferase expression was used (FIG. 13A). Antibodies 38002, 37464, and control-isotype were tested against target CHO cells stably expressing INSR. Data showed activity at concentrations of 37464 but not 38002 to INSR+ cells (FIG. 13B).

This Example further illustrates the surprising lack of INSR binding of 38002 at concentrations achievable in vivo, which is a critical feature of the 38000 series of PD-L1/PD-L2 antibodies and distinguishes them from the earlier generated 37464 antibody and renders them suitable for therapeutic use in patients.

Example 4—Assessment of the Binding Profile of 38002, 38003 and 38004 Using a Human Plasma Membrane Protein Cell Array Cell microarrays were used to screen for specific off-target binding interactions of 3 human IgG1 antibodies: 38002, 38003 and 38004 (collectively "test antibodies"). The test antibodies target human CD274 (PD-L1) and PDCD1LG2 (PD-L2).

Investigation of the levels of binding of each test antibody to fixed untransfected HEK293 cells, and to cells over-expressing CD274 (PD-L1) and PDCD1LG2 (PD-L2) showed 20 µg/mL of each of the test antibodies to be a suitable screening concentration. Therefore, 20 µg/mL of test antibody 38002 was screened for binding against fixed human HEK293 cells, individually expressing 5861 full-length human plasma membrane proteins and cell surface-tethered human secreted proteins plus a further 371 human heterodimers. This revealed 37 Library hits altogether.

Each Library hit was re-expressed, along with 2 control receptors, and re-tested with 20 µg/mL of each test antibody or control treatments. This was performed on both fixed and live cells.

Test antibody 38002 showed specific interactions with its primary targets, CD274 (PD-L1) and PDCD1LG2 (PD-L2) on fixed and live cell microarrays. Additional interactions with CST1, CST4 and FBLN1 were observed on fixed cell microarrays, and with CST1, CST4, INSR isoform long, INSR isoform short and the INSR+IGF1R heterodimer on the live cell microarray. The interactions with the primary targets and INSR isoforms long and short were investigated further in a flow cytometry dose-response study. The $EC_{50}$ values for the interactions with the primary targets CD274 (PD-L1) and PDCD1LG2 (PD-L2) were found to be 0.03 and 0.1 µg/mL respectively, while the EC50 values for the interactions with INSR isoforms long and short were found to be 144.9 and 87.5 µg/mL respectively. The $EC_{50}$ value for isoform long is therefore 4830- and 1449-fold greater than for primary targets CD274 (PD-L1) and PDCD1LG2 (PD-L2) respectively. The $EC_{50}$ value for isoform short is 2930- and 875-fold greater than for primary targets CD274 (PD-L1) and PDCD1LG2 (PD-L2) respectively. These data suggest that the secondary interaction of 38002 with INSR are not biologically relevant.

While not screened against the entire protein library, when test antibody 38003 was screened against the hits generated by test antibody 38002, it showed specific interactions with its primary targets, CD274 (PD-L1) and PDCD1LG2 (PD-L2) on both fixed and live cell microarrays. Additional interactions with CST4 and FBLN1 were observed on fixed cell microarrays, and with CST1, CST4 and INSR isoform short on the live cell microarray. Similarly, when test antibody 38004 was screened against the hits generated by test antibody 38002, it showed specific interactions with its primary targets, CD274 (PD-L1) and PDCD1LG2 (PD-L2) on both fixed and live cell microarrays. Additional interactions with CST1 and CST4 were observed on the live cell microarray only.

Follow-on flow cytometry validation study. Human HEK293 cells were transfected with expression vectors encoding ZsGreen1 only, or ZsGreen1 and CD274 (PD-L1), PDCD1LG2 (PD-L2), INSR isoform long, INSR Isoform short or CD20 (assay control). Live cell transfectants were incubated with a dose range (0-300 µg/mL) of 38002, 1 µg/mL Rituximab biosimilar (assay control) or assay buffer only, as indicated. Cells were washed, and incubated with the same AF647 anti-human IgG Fc detection antibody as used in the cell microarray screens. Cells were again washed, and analyzed by flow cytometry using an Accuri flow cytometer (BD). A 7AAD live/dead dye was used to exclude dead cells in the analysis, and ZsGreen+ (transfected) cells were selected for analysis.

Confirmation/Specificity screen (fixed cells). In a subsequent Confirmation/Specificity screen, all 37 Library hits, INSR+IGFR and 2 control receptors (CD20 and EGFR) were over-expressed in HEK293 cells. As expected, the Rituximab biosimilar showed a medium/strong intensity interaction with over-expressed CD20, validating the incubation conditions and detection system.

Test antibody 38002 showed specific interactions with its primary targets, CD274 (PD-L1) (strong intensity) and PDCD1LG2 (PD-L2) (strong intensity). Test antibody 38002 showed additional interactions with CST1 (very weak and weak intensity), CST4 (weak/medium intensity) and FBLN1 (weak/medium intensity).

When screened against the library hits generated by test antibody 38002, test antibody 38003 showed specific interactions with its primary targets CD274 (PD-L1) (strong intensity) and PDCD1LG2 (PD-L2) (strong intensity). Test antibody 38003 also showed additional interactions with CST4 (strong and medium/strong intensity) and FBLN1 (medium/strong intensity).

When screened against the library hits generated by test antibody 38002, test antibody 38004 showed specific interactions with its primary targets CD274 (PD-L1) (strong intensity) and PDCD1LG2 (PD-L2) (strong intensity).

Confirmation/Specificity screen (live cells). In a Confirmation/Specificity screen performed on live cells in the absence of cell fixation, test antibody 38002 showed specific interactions with its primary targets, CD274 (PD-L1) and PDCD1LG2 (PD-L2) and additional interactions with INSR (isoforms long and short), CST1, CST4 and INSR_IGF1R. The interaction between 38002 and FBLN1, that was weak/med intensity in the fixed cell microarrays, was very weak intensity (non-significant) in the live cell microarray.

Test antibody 38003 showed specific interactions with its primary targets, CD274 (PD-L1) and PDCD1LG2 (PD-L2) and additional interactions with INSR (isoform short), CST1 and CST4.

Test antibody 38004 showed specific interactions with its primary targets, CD274 (PD-L1) and PDCD1LG2 (PD-L2) and additional interactions with CST1 and CST4.

Flow cytometry follow up results (live cells). In order to investigate some of the identified specific interactions of test antibody 38002 further, CD274 (PD-L1), PDCD1LG2 (PD-L2), INSR isoform long, INSR Isoform short or CD20 were over-expressed in HEK293 cells. Live cell transfectants, including ZsGreen1-only transfected cells, were incubated with a dose range (0-300 µg/mL) of 38002, 1 µg/mL Rituximab biosimilar (assay control) or assay buffer alone. Interactions were then investigated by flow cytometry.

Test antibody 38002 showed binding to its primary targets CD274 (PD-L1) and PDCD1LG2 (PD-L2) with $EC_{50}$ values of 0.03 and 0.1 µg/mL respectively. Binding was also observed with INSR isoform long and isoform short with $EC_{50}$ values of 144.9 and 87.5 µg/mL respectively. The EC50 value for isoform long is therefore 4830- and 1449-fold greater than for primary targets CD274 (PD-L1) and PDCD1LG2 (PD-L2) respectively. The EC50 value for isoform short is 2930- and 875-fold greater than for primary targets CD274 (PD-L1) and PDCD1LG2 (PD-L2) respectively.

Conclusions. Test antibody 38002 showed specific interactions with its primary targets, CD274 (PD-L1) and PDCD1LG2 (PD-L2) on fixed and live cell microarrays. Additional interactions with CST1, CST4 and FBLN1 were observed on fixed cell microarrays, and with CST1, CST4, INSR isoform long, INSR isoform short and the INSR+ IGF1R heterodimer in the live cell microarray. When the interactions with the primary targets and INSR isoforms long and short were investigated further in a flow cytometry dose-response study, the EC50 values for the interactions with the primary targets CD274 (PD-L1) and PDCD1LG2 (PD-L2) were found to be 0.03 and 0.1 µg/mL respectively, while the $EC_{50}$ values for the interactions with INSR isoforms long and short were found to be 144.9 and 87.5 µg/mL respectively. The $EC_{50}$ value for isoform long is therefore 4830- and 1449-fold greater than for primary targets CD274 (PD-L1) and PDCD1LG2 (PD-L2) respectively. The $EC_{50}$ value for isoform short is 2930- and 875-fold greater than for primary targets CD274 (PD-L1) and PDCD1LG2 (PD-L2) respectively. These data suggest that the secondary interaction of 38002 with INSR are not biologically relevant.

Example 5

BiPDL antibodies with effector function mediate efficient ADCC against PD-L1 and PD-L2 expressing tumor cells. The inventor evaluated the effector functions of BiPDL antibodies by using primary murine NK cells and calcein-AM labeled U9240 PMBL target cells. Percent specific lysis showed that mouse IgG2a 21680 and 21661 were capable of efficiently mediating ADCC against U2940 (FIG. 14A). To examine BiPDL antibodies effector functions for ADCC and ADCP, the inventor employed the Promega reporter Bioassays for ADCC (Jurkat/FcyRIIa) and ADCP with (Jurkat/FcyRIIIa). The data show that 27869, 27907, and 37464 were able to induce much stronger ADCC and ADCP signaling when compared to Avelumab or to a control isotype.

BiPDL inhibit tumor growth and increase survival in the "cold' tumor mouse model B16-PD-L2 melanoma by increasing T cell activation and decreasing myeloid suppression. To evaluate the efficacy of BiPDL antibodies in the context of "cold' tumors, the inventor employed B16F10 melanoma cells, overexpressing murine PD-L2. Mice were treated with the control anti-mouse-PD-1 clone RMP1-14, a combination of mouse IgG2a anti-PD-L1 and anti-PD-L2 antibodies, or BiPDL antibodies 27869 and 37464. As previously observed, B16 tumor growth was not affected by anti-PD1 treatment. However, treatment with BiPDL antibodies was able to both reduce tumor growth (FIG. 15A) and increase mouse survival (FIG. 15B), suggesting a immuno-modulatory function of BiPDL antibodies in the tumor microenvironment. A marginally higher efficacy was noted for 27869.

To determine the mechanism behind this therapeutic response, the inventor analyzed immune cell populations and their activation status in tumors and lymph nodes. Lymph nodes of mice treated with BiPDL antibodies exhibited higher Ki67 fluorescence by CD4 (FIG. 15C) and CD8 (FIG. 15D) T cells than in mice treated by an anti-PD1, anti-PD-L1, or anti-PD-L2 antibody. BiPDL-treated mice also presented a significantly higher proportion of CD8+ dendritic cells in their lymph nodes than other treatment conditions (FIG. 15E). In tumors, a lower percentage of macrophages (FIG. 15F), granulocytic myeloid derived suppressive cells (MDSC, FIG. 15G), and monocytic MDSCs (FIG. 15H) expressed arginase, a immuno-suppressive marker, in mice were treated with 37464 compared with mice treated with anti-PD1. [0212]27869 and 37464 behaved similarly in vitro and 27869 showed a minimal therapeutic advantage in the B16 model. However, in mice implanted with the colon cancer cell line CT26 (considered a hot tumor mouse model), treatment with 37464 led to a drastically stronger reduction of tumor growth over 27869 (FIG. 16A). To further, investigate these differences the inventor hypothesized that 27869 and 37464 might have different effect on the PD-L1-B7.1 interaction which results in a costimulatory function over T-cells. Thus, the inventor designed a combinational bioassay by using PE-labeled human recombinant B7.1 over live CHO/PD-L1 cells analyzed by flow cytometry. These data show that PE-labeled human recombinant B7.1 binding is blocked when to CHO/PD-L1 cells are pretreated with 37464 but not when preincubated with 27869 or control antibodies. This important very important functional and structural result that makes BIPDL to be extremely rare antibody with triple blockade (PD-L1, PD-L2 and B7.1 blockade), with enhanced effector functions ADCC and ADCP. Taking all together these results indicate that the 37464 lineage would be a better lead over that of 27869.

Figure 17A:
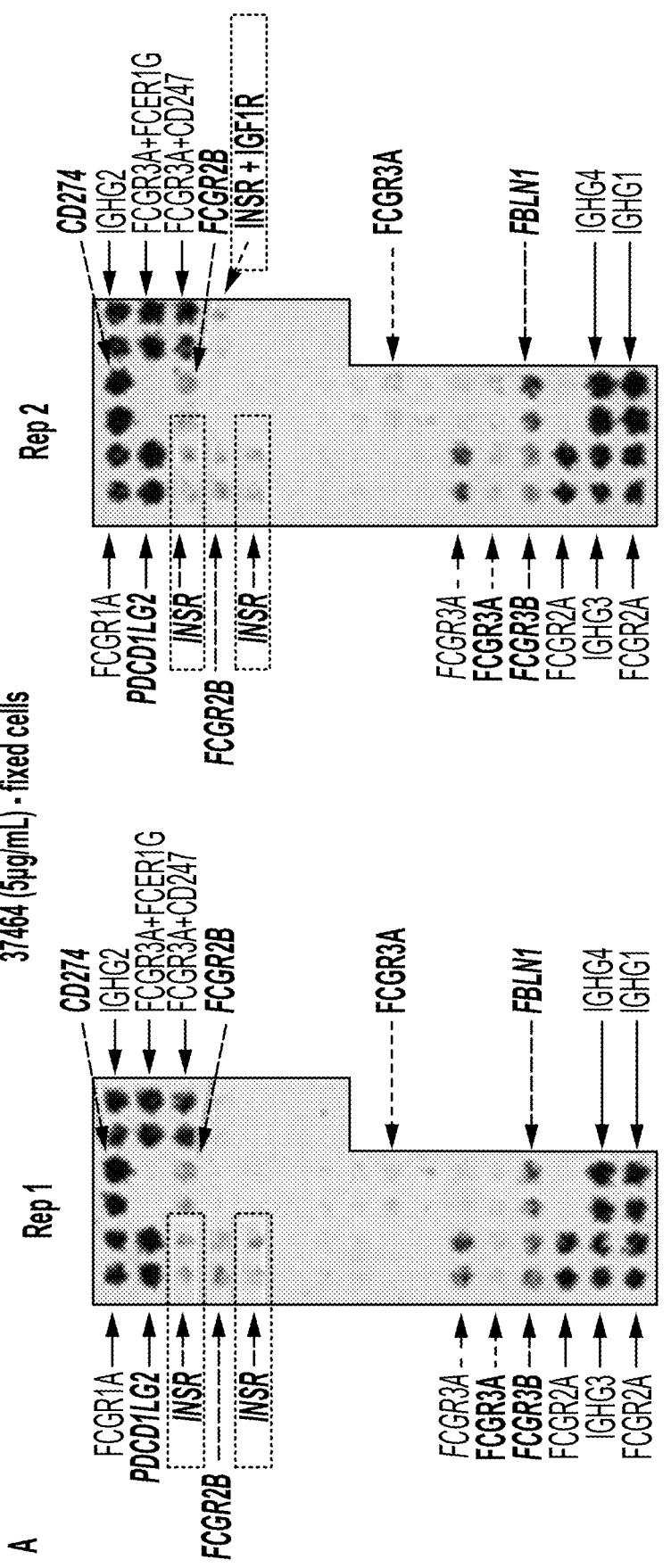
Figure 17B:
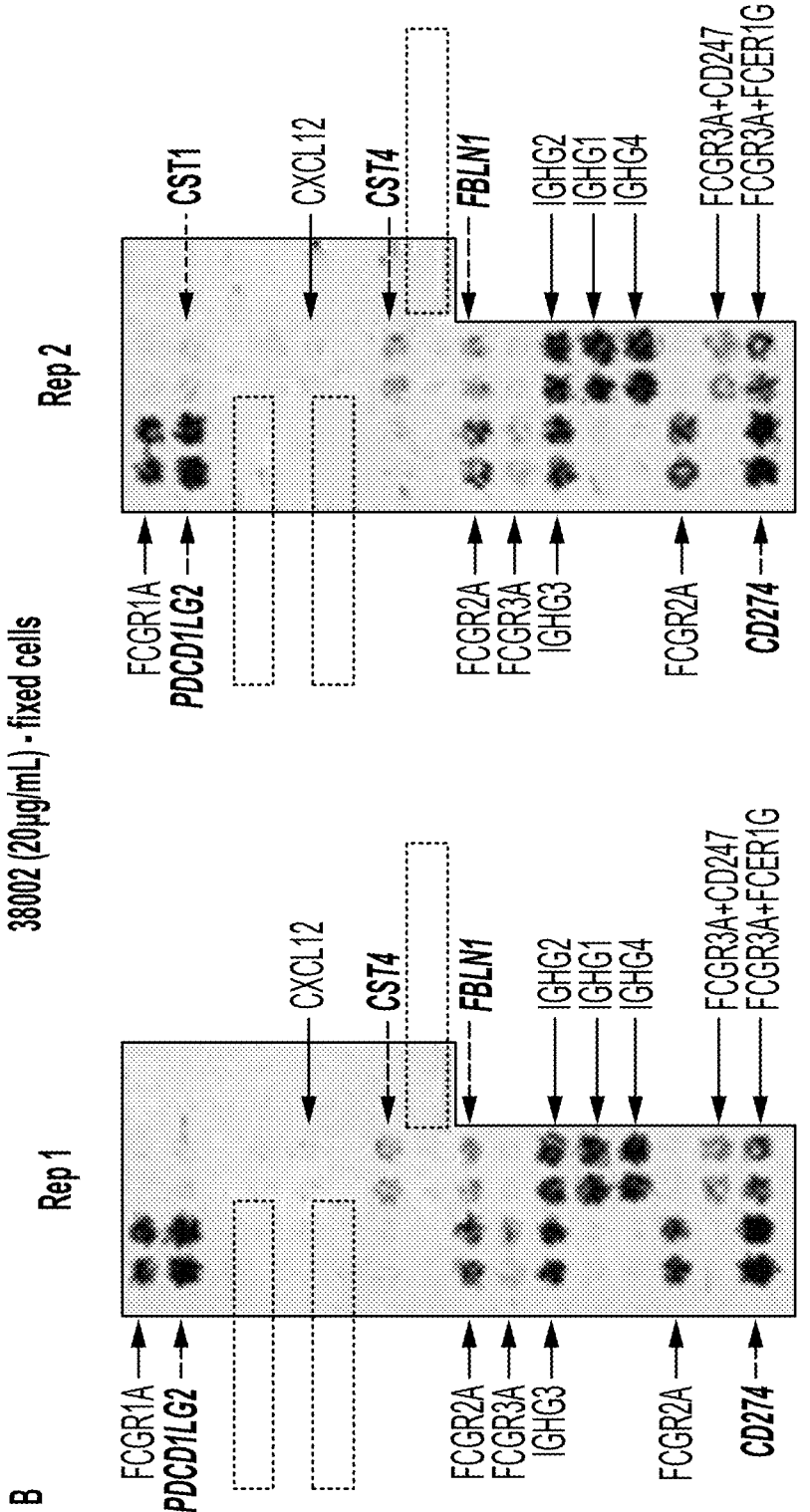

BiPDL antibodies off-target profiling and further variable region engineering/selection round eliminated the off-target binding and conserved the triple blockade and effector functions. Off-target binding can significantly affect the pharmacokinetics (PK), tissue distribution, efficacy, and toxicity of a therapeutic antibody. Here the inventor has conducted a first screen and had not revealed any notable off-target binding of BiPDL antibodies, a further human plasma membrane protein cell array revealed that 37464 displayed binding with the insulin receptor INSR (FIG. 17A). In order eliminate the off-target binding to INSR and retaining a therapeutic affinity for PD-L1 and PD-L2, 2 targeted point mutations in the variable region CDRL1 and CDRL3 were performed in the light chains of 37464. The inventor obtained a new engineered antibody designated as 38002 that conserved the affinities for PD-L1 and PD-L2 measuring at $K_d=7.62\times10^{-9}$ for PD-L1 and $K_d=1.9\times10^{-9}$ for PD-L2 (Monomeric human ligands, FIG. 18A) while eliminating the off-target binding to INSR.

To confirm the elimination of the of binding of 38002 to INSR, BiPDL antibodies were incubated at different concentrations with INSR-expressing cells. 37464 displayed binding with INSR at concentrations as low as 1 nM, whereas binding of 38002 to INSR did not show significant binding at 33 nM and remained minimal at 100 nM (FIG. 17C), both for the short and long isoforms of the protein (FIG. 18B). Moreover, flow cytometry staining confirmed that 38002 conserved high binding activity to PD-L1 and PD-L2 and retained its PD-1 blockade activity in Promega bioassay with its ligand remained equivalent to the anti-PD-1 Keytruda (FIGS. 17D-E). Furthermore, 38002 retained its effector functions ADCC and ADCP (FIGS. 17F-G) only when cells express PD-Ligands but not INSR or control (FIGS>174F).

Novel antibody increases cytotoxic and decreases suppressive cell infiltration in B16-PD-L2 melanoma. To confirm that the novel antibody 38002 maintained in vivo efficacy as previously observed, mice were implanted with B16 melanoma and treated with a mouse IgG2a anti-PD-1, anti-PD-L1 and/or anti-PD-L2, or 38002. While PD-1 blocking does not improved survival in this model, 38002 increased survival more efficiently than any other treatment with a 50% survival rate observed). When tumors were analyzed ex vivo by flow cytometry, a non-significant increase of the proportion of NK cells in the tumor immune infiltrated was noted (FIG. 19B). Interestingly, the percentage of CD8 T cells (FIG. 19C) as well as their cytotoxic functions illustrated by granzyme B (FIG. 19D) and perforin (FIG. 19E) expression were significantly increased after treatment with 38002. In association with this cytotoxic response, the inventor also observed a decrease in immunosuppressive cell proportions, including granulocytic (FIG. 19F) and monocytic (FIG. 19G) MDSCs as well as macrophages (FIG. 19H).

Novel antibody inhibits tumor growth in human MDA-MB-231 breast cancer associated with decreased myeloid cells. To assess the effect of IMGS001 on the growth of MDA-MB-231 in vivo in a T-cell free microenvironment, nude mice were challenged with $1\times10^6$ MDA-MB-231 cells orthotopically in the fourth left mammary gland. Starting three days after the challenge, mice were treated i.p. with IMGS-001, Avelumab, or PBS as control every three days for a total of 7 administrations. Tumors were measured twice per week. Mice that received IMGS-001 or Avelumab had slower tumor growth compared to the PBS-treated control group (FIG. 21A). On days 14, 17, and 19, mice treated with IMGS-001 had significantly lower tumor volumes compared to the control group, while mice treated with Avelumab, had significantly lower tumor volumes compared to controls only at day 17. At day 19 mice were culled and tumors collected for microscopic examination. The immunohistochemical analysis showed an evenly distributed infiltration of numerous CD11b positive cells in untreated tumors, which were strikingly and consistently decreased to about one-third in tumors from IMGS-001-treated mice.

It will be readily understood that the components of various embodiments of the present invention, as generally described and illustrated in the figures herein, may be arranged and designed in a wide variety of different configurations. Thus, the detailed description of the embodiments of the present invention, as represented in the attached figures, is not intended to limit the scope of the invention as claimed but is merely representative of selected embodiments of the invention.

The features, structures, or characteristics of the invention described throughout this specification may be combined in any suitable manner in one or more embodiments. For example, reference throughout this specification to "certain embodiments," "some embodiments," or similar language means that a particular feature, structure, or characteristic described in connection with the embodiment is included in at least one embodiment of the present invention. Thus, appearances of the phrases "in certain embodiments," "in some embodiment," "in other embodiments," or similar language throughout this specification do not necessarily all refer to the same group of embodiments and the described features, structures, or characteristics may be combined in any suitable manner in one or more embodiments.

It should be noted that reference throughout this specification to features, advantages, or similar language does not imply that all of the features and advantages that may be realized with the present invention should be or are in any single embodiment of the invention. Rather, language referring to the features and advantages is understood to mean that a specific feature, advantage, or characteristic described in connection with an embodiment is included in at least one embodiment of the present invention. Thus, discussion of the features and advantages, and similar language, throughout this specification may, but do not necessarily, refer to the same embodiment.

Furthermore, the described features, advantages, and characteristics of the invention may be combined in any suitable manner in one or more embodiments. One skilled in the relevant art will recognize that the invention can be practiced without one or more of the specific features or advantages of a particular embodiment. In other instances, additional features and advantages may be recognized in certain embodiments that may not be present in all embodiments of the invention.

One having ordinary skill in the art will readily understand that the invention as discussed above may be practiced with steps in a different order, and/or with hardware elements in configurations which are different than those which are disclosed. Therefore, although the invention has been described based upon these preferred embodiments, it would be apparent to those of skill in the art that certain modifications, variations, and alternative constructions would be apparent, while remaining within the spirit and scope of the invention. In order to determine the metes and bounds of the invention, therefore, reference should be made to the appended claims.

VIII. REFERENCES

The following references, to the extent that they provide exemplary procedural or other details supplementary to those set forth herein, are specifically incorporated herein by reference.

"*Antibodies: A Laboratory Manual*," Cold Spring Harbor Press, Cold Spring Harbor, NY, 1988.

Abbondanzo et al., *Am. J. Pediatr. Hematol. Oncol.,* 12(4), 480-489, 1990.

Allred et al., *Arch. Surg.,* 125(1), 107-113, 1990.

Atherton et al., *Biol. of Reproduction,* 32, 155-171, 1985.

Austin et al., *PLoS Pathog* 8, e1002930, 2012.

Baptista et al., *Hum. Pathol.,* 47: 78-84, 2016.

Barrett et al., *Oncotarget,* 6: 26483-26493, 2015.

Boussiotis, *N Engl J Med,* 375: 1767-1778, 2016.

Boyerinas et al., *Cancer Immunol. Res.,* 3: 1148-1157, 2015.

Brahmer et al., *J. Clin. Oncolo.,* 28:3167-3175, 2010.

Brahmer et al., *N. Eng. J. Med,* 366:2455-2465; 2012.

Brehin, et al., *Virology* 371:185-195, 2008.

Brown et al., *J. Immunol. Meth.,* 12; 130(1): 111-121, 1990.

Butte et al., *Immunity,* 27: 111-122, 2007.

Butte et al., *Mol. Immunol.,* 45: 3567-3572, 2008.

Campbell, *In: Monoclonal Antibody Technology, Laboratory Techniques in Biochemistry and Molecular Biology,* Vol. 13, Burden and Von Knippenberg, Eds. pp. 75-83, Amsterdam, Elsevier, 1984.

Capaldi et al., *Biochem. Biophys. Res. Comm.,* 74(2):425-433, 1977.

Cheng et al., *J. Biol. Chem.,* 288: 11771-11785, 2013.

Christian et al., *Proc Natl Acad Sci USA,* 110:18662-18667, 2013.

Danilova et al., *Proc. Natl. Acad. Sci. U.S. A.,* 113: E7769-E7777, 2016.

De Jager et al., *Semin. Nucl. Med.* 23(2): 165-179, 1993.

Derks et al., *Cancer. Immunol. Res.,* 3: 1123-1129, 2015.

Dholakia et al., *J. Biol. Chem.,* 264, 20638-20642, 1989.

Doolittle and Ben-Zeev, *Methods Mol. Biol.,* 109, 215-237, 1999.

Dong et al., *Hum. Pathol.,* 2016.

Dong et al, *Nat. Medicine,* 8:793-800, 2002.

Estep et al., *Mabs,* 5(2): 270-278, 2013.

Frie et al., *J. Infect. Dis.* 207:319-322, 2013.

Gefter et al., *Somatic Cell Genet.,* 3:231-236, 1977.

Goh et al., *Clin. Immunol.* 149:487-497, 2013.

Green et al., *Blood,* 116: 3268-3277, 2010.

Gulbis and Galand, *Hum. Pathol.* 24(12), 1271-1285, 1993.

Guo et al., *Sci. Transl. Med.* 3:99 ra85, 2001.

Howitt et al., *J.A.M.A. Oncol.,* 2: 518-522, 2016.

Inoue et al., *Oncotarget,* 7: 32113-32128, 2016.

Kam et al., *EMBO Mol. Med.* 4, 330-343, 2012b.

Kam et al., *J. Virol.* 86, 13005-13015, 2012a.

Kam et al., *PLoS One* 9, e95647, 2014.

Khatoon et al., *Ann. of Neurology,* 26, 210-219, 1989.

Kim et al., *Lung Cancer,* 88: 24-33, 2015.

Kim et al., *Eur. J. Cancer,* 51: 2698-2707, 2015.

King et al., *J. Biol. Chem.,* 269, 10210-10218, 1989.

Kohler and Milstein, *Eur. J. Immunol.,* 6, 511-519, 1976.

Kohler and Milstein, *Nature,* 256, 495-497, 1975.

Kyte and Doolittle, *J. Mol. Biol.,* 157(1):105-132, 1982.

Lanciotti & Valadere, *Emerg Infect Dis* 20, 2014.

Latchman et al., *Nat. Immunol.,* 2: 261-268, 2001.

Lee et al., *Nat. Commun.,* 7: 12220, 2016.

Lee et al., *PLoS Pathog.* 7:e1002390, 2011.

Levitt et al., *Vaccine* 4, 157-162, 1986.

Li et al., *J. Biol. Chem.,* 292: 6799-6809, 2017.

Lum et al., *J. Immunol.* 190:6295-6302, 2013.

Mainou et al., *MBio* 4, 2013.

Masrinoul et al., *Virology* 464-465, 111-117, 2014.

Messer et al., *Proc. Natl. Acad. Sci. USA* 111:1939-1944, 2014.

Morrison et al., *Am J Pathol,* 178:32-40, 2011.

Nakamura et al., *In: Enzyme Immunoassays: Heterogeneous and Homogeneous Systems,* Chapter 27, 1987.

Nazareth et al., *J. Immunology,* 178(9): 5552-5562, 2007.

Nie et al., *Cell Mol. Immunol.,* 2017.

Nomi et al., *Clin. Cancer Res.,* 13: 2151-2157, 2007.

Obeid et al., *Oncoimmunolo gy,* 5: e 1235107, 2016.

Ohigashi et al., *Clin. Cancer Res.,* 11: 2947-2953, 2005.

O'Shannessy et al., *J. Immun. Meth.,* 99, 153-161, 1987.

Paes et al., *J. Am. Chem. Soc.,* 131:6952-6954, 2009.

Pal et al., *PLoS Pathog* 9, e1003312, 2013.

Persic et al., *Gene* 187: 1, 1997

Pinchuk et al., *Gastroenterology,* 135(4): 1228-1237, 2008.

Potter and Haley, *Meth. Enzymol.,* 91, 613-633, 1983.

Remington's Pharmaceutical Sciences, 15th Ed., 3:624-652, 1990.

Roemer et al., *J. Clin. Oncol.,* 2016.

Rozali et al., *Clinical and Developmental Immunology;* 2012: 656340, 2012.

R.C. Team, R Foundation for Statistical Computing, Vienna, Austria, 2014.

Schilte et al., *PLoS Negl. Trop. Dis.* 7:e2137, 2013.

Selvarajah et al., *PLoS Negl. Trop. Dis.* 7:e2423, 2013.

Siegel et al., *J Immunol Methods,* 286(1-2): 141-153, 2004.

Shi et al., *Am. J. Surg. Pathol.,* 38: 1715-1723, 2014.

Shin et al., *Ann. Surg. Oncol.,* 2015.

Shin et al., *Ann. Surg. Oncol.,* 23: 694-702, 2016.

Sissoko et al., *PLoS Negl. Trop. Dis.* 3:e389, 2009.

Smith et al., *MBio* 4, e00873-00813, 2013a.

Sun et al., *Elife* 2:e00435, 2013.

Sun et al., *J. Steroid Biochem.,* 26(1):83-92, 1987.

Sunshine and Taube, *Curr. Opin. Pharmacol.,* 23: 32-38, 2015.

Tang et al., *J. Biol. Chem.*, 271:28324-28330, 1996.
Thompson et al., *Proc. Natl Acad. Sci. USA*, 101(49): 17174-17179, 2004.
Thornburg et al., *J. Clin. Invest.*, 123:4405-4409, 2013.
U.S. Pat. No. 3,817,837
U.S. Pat. No. 3,850,752
U.S. Pat. No. 3,939,350
U.S. Pat. No. 3,996,345
U.S. Pat. No. 4,196,265
U.S. Pat. No. 4,275,149
U.S. Pat. No. 4,277,437
U.S. Pat. No. 4,366,241
U.S. Pat. No. 4,472,509
U.S. Pat. No. 4,554,101
U.S. Pat. No. 4,680,338
U.S. Pat. No. 4,816,567
U.S. Pat. No. 4,867,973
U.S. Pat. No. 4,938,948
U.S. Pat. No. 5,021,236
U.S. Pat. No. 5,141,648
U.S. Pat. No. 5,196,066

U.S. Pat. No. 5,563,250
U.S. Pat. No. 5,565,332
U.S. Pat. No. 5,856,456
U.S. Pat. No. 5,880,270
Vander Veen et al., *Anim Health Res Rev*, 13:1-9, 2012.
Van Deventer and Wittrup, *Methods Mol. Biol.*, 1131: 151-181, 2014.
Van Roosbroeck et al., *Genes Chromosomes Cancer*, 55: 428-441, 2016.
Voss et al., *Nature*, 468:709-712, 2010.
Wang et al., *World J. Gastroenterol.*, 17: 3322-3329, 2011.
Warter et al., *J. Immunol.*, 186:3258-3264, 2011.
Wawrzynczak & Thorpe, In: *Immunoconjugates, Antibody Conjugates In Radioimaging And Therapy Of Cancer*, Vogel (Ed.), NY, Oxford University Press, 28, 1987.
Xiao et al., *J. Exp. Med.*, 211: 943-959, 2014.
Xu et al., *PEDS* 26.10: 663-70, 2013.
Yearley et al., *Clin. Cancer. Res.*, 23: 3158-3167, 2017.
Yu et al., *Nature* 455:532-536, 2008.

What is claimed:

1. An antibody or an antigen binding fragment thereof comprising a heavy chain CDR1 amino acid sequence set forth in SEQ ID NO:7, a heavy chain CDR2 amino acid sequence set forth in SEQ ID NO:8, and a heavy chain CDR3 amino acid sequence as set forth in SEQ ID NO:9 and light chain CDR1 amino acid sequence set forth in SEQ ID NO:10, a light chain CDR2 sequence set forth in SEQ ID NO:11, and a light chain CDR3 amino acid sequence set forth in SEQ ID NO:12.

2. The antibody or antibody fragment of claim 1, wherein said antibody or antibody fragment is encoded by light chain variable sequence as set forth in SEQ ID NO:5 and heavy chain variable sequence as set forth in SEQ ID NO:3.

3. The antibody or antibody fragment of claim 1, wherein said antibody or antibody fragment is encoded by light chain variable sequence having at least 90% identity to SEQ ID NO:5 and heavy chain variable sequence having at least 90% identity to SEQ ID NO:3.

4. The antibody or antibody fragment of claim 1, wherein said antibody or antibody fragment is encoded by light chain variable sequence having at least 95% identity to SEQ ID NO:5 and heavy chain variable sequence having at least 95% identity to SEQ ID NO:3.

5. The antibody or antibody fragment of claim 1, wherein said antibody or antibody fragment comprises light chain variable sequence of SEQ ID NO:6 and heavy chain variable sequence of SEQ ID NO:4.

6. The antibody or antibody fragment of claim 1, wherein said antibody or antibody fragment comprises light chain variable sequences having at least 90% identity to SEQ ID NO:6 and heavy chain variable sequence having at least 90% identity to SEQ ID NO:4.

7. The antibody or antibody fragment of claim 1, wherein said antibody or antibody fragment comprises light chain variable sequence having at least 95% identity to SEQ ID NO:6 and heavy chain variable sequence having at least 95% identity to SEQ ID NO:4.

8. The antibody or antibody fragment of claim 1, wherein the antibody fragment is a recombinant scFv (single chain fragment variable) antibody, Fab fragment, F(ab')2 fragment, or Fv fragment.

9. The antibody or antibody fragment of claim 1, wherein said antibody is a chimeric antibody.

10. The antibody or antibody fragment of claim 1, wherein said antibody is an IgG.

11. The antibody or antibody fragment of claim 1, wherein said antibody or antibody fragment further comprises a cell penetrating peptide and/or is an intrabody.

12. The antibody or fragment of claim 1, wherein said antibody or antibody fragment is a human antibody or a humanized antibody.

13. The antibody or fragment of claim 1, wherein said antibody or antibody fragment exhibits reduced binding to the human insulin-like growth factor 1 receptor (IGF1R) compared to an antibody comprising the CDR regions of ADI-37464.

14. The antibody of claim 1, wherein said antibody or antigen binding fragment thereof binds to PD-L1.

15. The antibody of claim 1, wherein said antibody or antigen binding fragment thereof binds to PD-L2.

16. The antibody of claim 1, wherein said antibody or antigen binding fragment thereof possesses a $K_D$ for PD-L1 of $1 \times 10^{-8}$ M or less.

17. The antibody of claim 1, wherein said antibody or antigen binding fragment thereof possesses a $K_D$ for PD-L2 of $1 \times 10^{-8}$ M or less.

18. A method of treating a subject having cancer comprising delivering to said subject an antibody or antibody fragment having heavy chain CDR sequences SEQ ID NO:7, SEQ ID NO:8, and SEQ ID NO:9 and light chain CDR sequences SEQ ID NO:10, SEQ ID NO:11, and SEQ ID NO:12.

19. A hybridoma or engineered cell expressing an antibody or antibody fragment wherein the antibody or antibody fragment has heavy chain CDR sequences SEQ ID NO:7, SEQ ID NO:8, and SEQ ID NO:9 and light chain CDR sequences SEQ ID NO:10, SEQ ID NO:11, and SEQ ID NO:12.

20. A method of detecting a PD-L1 or PD-L2 expressing cell in a subject comprising:

(a) contacting a sample from said subject with an antibody or antibody fragment having heavy chain CDR sequences of SEQ ID NO:4 and light chain CDR sequences of SEQ ID NO:6; and (b) detecting a PD-L1 or PD-L2 expressing cell in said sample by binding of said antibody or antibody fragment to a cell in said sample.

* * * * *

58

SEQUENCE LISTING

```
Sequence total quantity: 25
SEQ ID NO: 1            moltype = AA  length = 290
FEATURE                 Location/Qualifiers
source                  1..290
                        mol_type = protein
                        organism = Homo sapiens
SEQUENCE: 1
MRIFAVFIFM TYWHLLNAFT VTVPKDLYVV EYGSNMTIEC KFPVEKQLDL AALIVYWEME 60
DKNIIQFVHG EEDLKVQHSS YRQRARLLKD QLSLGNAALQ ITDVKLQDAG VYRCMISYGG 120
ADYKRITVKV NAPYNKINQR ILVVDPVTSE HELTCQAEGY PKAEVIWTSS DHQVLSGKTT 180
TTNSKREEKL FNVTSTLRIN TTTNEIFYCT FRRLDPEENH TAELVIPELP LAHPPNERTH 240
LVILGAILLC LGVALTFIFR LRKGRMMDVK KCGIQDTNSK KQSDTHLEET 290

SEQ ID NO: 2            moltype = AA  length = 273
FEATURE                 Location/Qualifiers
source                  1..273
                        mol_type = protein
                        organism = Homo sapiens
SEQUENCE: 2
MIFLLLMLSL ELQLHQIAAL FTVTVPKELY IIEHGSNVTL ECNFDTGSHV NLGAITASLQ 60
KVENDTSPHR ERATLLEEQL PLGKASFHIP QVQVRDEGQY QCIIIYGVAW DYKYLTLKVK 120
ASYRKINTHI LKVPETDEVE LTCQATGYPL AEVSWPNVSV PANTSHSRTP EGLYQVTSVL 180
RLKPPPGRNF SCVFWNTHVR ELTLASIDLQ SQMEPRTHPT WLLHIFIPFC IIAFIFIATV 240
IALRKQLCQK LYSSKDTTKR PVTTTKREVN SAI 273

SEQ ID NO: 3            moltype = DNA  length = 1353
FEATURE                 Location/Qualifiers
source                  1..1353
                        mol_type = other DNA
                        organism = synthetic construct
SEQUENCE: 3
caagttcaac tccaacaatg gggtgccggg ctgctgaagc cgtccgaaac gttgagtctc 60
acctgcgccg tgtacggcgg cagtctttca ggctatccat ggtcctggat aaggcagccc 120
cccggcaagg gtctcgaatg dataggtgag acggacgtgt ctggctggac agattacaac 180
ccttctctga agtctcgcgt taccatttcc gtagatacaa gtaagaatca gttctcactg 240
aagctcagtt ctgtaaccgc tgccgacacc gcagtgtact attgtcaag agatggacgc 300
aggatgggaa ctccaagctt tgacatttgg ggccagggta cgatggtgac tgtttcctcc 360
gcctcaacga aagggccatc tgtattccca ttggctccga gtagtaagag tacaagtggt 420
gggaccgcag cgctgggatg cctcgtcaag gattattttc ccgaaccagt aactgtaagt 480
tggaatagcg gggcattgac aagcggcgtt cacacctttc cagcggtgct tcaatcttct 540
ggactctact cattgagctc agttgtcacc gttccttcaa gttccttggg cacgcagaca 600
tatatctgca atgtgaatca taaaccttct aatacgaagg tcgataagaa agtggagccc 660
aaatcatgtg ataagacgca tacttgcccc ccctgcccag cccctgagct gttggcaggt 720
cccgatgtct ttctcttcc gcccaagccg aaggatacgc ttatgatctc caggactcct 780
gaggtgactt gcgtcgttgt cgacgtatcc cacgaagatc ctgaggtgaa gtttaattgg 840
tatgtcgacg gagtagaggt gcataatgct aaaacgaaac ctcggggaga gcaatataat 900
tccacttaca gagtagtgag cgttctcaca gttttgcatc aggactggct taacggaaag 960
gagtataaat gtaaggtcag taacaaagct cttccagctc ccgaggagaa aacaatttca 1020
aaggcaaagg gccaacctag ggaaccgcag gtgtatactc tccccccaag ccgcgaagaa 1080
atgacgaaaa accaggtgtc cctcacttgc ctggtcaaag gtttctatcc ttctgacata 1140
gcggtggagt gggagagtaa cggccaacca gagaacaatt ataagaccac gcctccagtt 1200
```

```
ctggattccg atgggatcatt ctttctgtac tctaaattga cggttgacaa atcccgctgg   1260
cagcagggaa acgtattttc atgttccgtg atgcatgaag ctttgcacaa tcactacact   1320
caaaagagtt tgagcttgtc accgggaaag taa                                1353

SEQ ID NO: 4              moltype = AA   length = 450
FEATURE                   Location/Qualifiers
source                    1..450
                          mol_type = protein
                          organism = synthetic construct
SEQUENCE: 4
QVQLQQWGAG LLKPSETLSL TCAVYGGSLS GYPWSWIRQP PGKGLEWIGE TDVSGWTDYN   60
PSLKSRVTIS VDTSKNQFSL KLSSVTAADT AVYYCARDGR RMGTPSFDIW GQGTMVTVSS   120
ASTKGPSVFP LAPSSKSTSG GTAALGCLVK DYFPEPVTVS WNSGALTSGV HTFPAVLQSS   180
GLYSLSSVVT VPSSSLGTQT YICNVNHKPS NTKVDKKVEP KSCDKTHTCP PCPAPELLAG   240
PDVFLFPPKP KDTLMISRTP EVTCVVVDVS HEDPEVKFNW YVDGVEVHNA KTKPREEQYN   300
STYRVVSVLT VLHQDWLNGK EYKCKVSNKA LPAPEEKTIS KAKGQPREPQ VYTLPPSREE   360
MTKNQVSLTC LVKGFYPSDI AVEWESNGQP ENNYKTTPPV LDSDGSFFLY SKLTVDKSRW   420
QQGNVFSCSV MHEALHNHYT QKSLSLSPGK                                    450

SEQ ID NO: 5              moltype = DNA   length = 645
FEATURE                   Location/Qualifiers
source                    1..645
                          mol_type = other DNA
                          organism = synthetic construct
SEQUENCE: 5
gacattcaga tgacgcaaag ccccagctct gtctcagctt ccgtgggtga tagggtgact   60
attacatgtc gagcctcaca agatattaat agctttcttg catggtatca gcaaaagcca   120
gggaaggcac ctaagctcct gatttatgct gcctcttctt gaatagcgg ggtcccctcc   180
cgcttctcag gatctgggtc agggactgac ttcacgctga ctatatcctc actccaacca   240
gaagatttcg ccacttatta ctgccaaaaa tccgtatatt tcccgcccac attcggtggt   300
gggacaaaag tggaaatcaa gagaactgtc gctgccccat ctgtttttcat ctttccaccg   360
agcgacgaac agctcaaaag cggcactgcg agtgttgttt gtctgctgaa taacttctat   420
cccagggaag caaaggtgca gtggaaggta gacaatgctc tgcaatccgg gaatagtcag   480
gaatccgtca cggagcaaga cagtaaggac tccacgtatt ccttgagtag tacattgacc   540
ctcagtaaag cggattacga aaacacaaaa gtttacgctt gtgaagtaac gcatcagggg   600
ttgtccagtc cggttaccaa atccttcaat cggggagagt gttga                  645

SEQ ID NO: 6              moltype = AA   length = 214
FEATURE                   Location/Qualifiers
source                    1..214
                          mol_type = protein
                          organism = synthetic construct
SEQUENCE: 6
DIQMTQSPSS VSASVGDRVT ITCRASQDIN SFLAWYQQKP GKAPKLLIYA ASSLNSGVPS   60
RFSGSGSGTD FTLTISSLQP EDFATYYCQK SVYFPPTFGG GTKVEIKRTV AAPSVFIFPP   120
SDEQLKSGTA SVVCLLNNFY PREAKVQWKV DNALQSGNSQ ESVTEQDSKD STYSLSSTLT   180
LSKADYEKHK VYACEVTHQG LSSPVTKSFN RGEC                               214

SEQ ID NO: 7              moltype = AA   length = 9
FEATURE                   Location/Qualifiers
source                    1..9
                          mol_type = protein
                          organism = synthetic construct
SEQUENCE: 7
GSLSGYPWS                                                           9

SEQ ID NO: 8              moltype = AA   length = 16
FEATURE                   Location/Qualifiers
source                    1..16
                          mol_type = protein
                          organism = synthetic construct
SEQUENCE: 8
ETDVSGWTDY NPSLKS                                                   16

SEQ ID NO: 9              moltype = AA   length = 14
FEATURE                   Location/Qualifiers
source                    1..14
                          mol_type = protein
                          organism = synthetic construct
SEQUENCE: 9
ARDGRRMGTP SFDI                                                     14

SEQ ID NO: 10             moltype = AA   length = 11
FEATURE                   Location/Qualifiers
source                    1..11
                          mol_type = protein
                          organism = synthetic construct
SEQUENCE: 10
RASQDINSFL A                                                        11
```

```
SEQ ID NO: 11           moltype = AA  length = 7
FEATURE                 Location/Qualifiers
source                  1..7
                        mol_type = protein
                        organism = synthetic construct
SEQUENCE: 11
AASSLNS                                                          7

SEQ ID NO: 12           moltype = AA  length = 9
FEATURE                 Location/Qualifiers
source                  1..9
                        mol_type = protein
                        organism = synthetic construct
SEQUENCE: 12
QKSVYFPPT                                                        9

SEQ ID NO: 13           moltype = AA  length = 11
FEATURE                 Location/Qualifiers
source                  1..11
                        mol_type = protein
                        organism = synthetic construct
SEQUENCE: 13
RASQGINSFL A                                                     11

SEQ ID NO: 14           moltype = AA  length = 7
FEATURE                 Location/Qualifiers
source                  1..7
                        mol_type = protein
                        organism = synthetic construct
SEQUENCE: 14
AADSIQS                                                          7

SEQ ID NO: 15           moltype = AA  length = 9
FEATURE                 Location/Qualifiers
source                  1..9
                        mol_type = protein
                        organism = synthetic construct
SEQUENCE: 15
QKAVYFPPT                                                        9

SEQ ID NO: 16           moltype = AA  length = 11
FEATURE                 Location/Qualifiers
source                  1..11
                        mol_type = protein
                        organism = synthetic construct
SEQUENCE: 16
RASKGISSFL A                                                     11

SEQ ID NO: 17           moltype = AA  length = 11
FEATURE                 Location/Qualifiers
source                  1..11
                        mol_type = protein
                        organism = synthetic construct
SEQUENCE: 17
RASQGISSFL A                                                     11

SEQ ID NO: 18           moltype = AA  length = 7
FEATURE                 Location/Qualifiers
source                  1..7
                        mol_type = protein
                        organism = synthetic construct
SEQUENCE: 18
AASSLQS                                                          7

SEQ ID NO: 19           moltype = AA  length = 9
FEATURE                 Location/Qualifiers
source                  1..9
                        mol_type = protein
                        organism = synthetic construct
SEQUENCE: 19
QSAVYFPPT                                                        9

SEQ ID NO: 20           moltype = AA  length = 450
FEATURE                 Location/Qualifiers
source                  1..450
                        mol_type = protein
                        organism = synthetic construct
SEQUENCE: 20
```

```
QVQLQQWGAG LLKPSETLSL TCAVYGGSLS GYPWSWIRQP PGKGLEWIGE TDVSGWTDYN    60
PSLKSRVTIS VDTSKNQFSL KLSSVTAADT AVYYCARDGR RMGTPSFDIW GQGTMVTVSS   120
ASTKGPSVFP LAPSSKSTSG GTAALGCLVK DYFPEPVTVS WNSGALTSGV HTFPAVLQSS   180
GLYSLSSVVT VPSSSLGTQT YICNVNHKPS NTKVDKKVEP KSCDKTHTCP PCPAPELLAG   240
PDVFLFPPKP KDTLMISRTP EVTCVVVDVS HEDPEVKFNW YVDGVEVHNA KTKPREEQYN   300
STYRVVSVLT VLHQDWLNGK EYKCKVSNKA LPAPEEKTIS KAKGQPREPQ VYTLPPSREE   360
MTKNQVSLTC LVKGFYPSDI AVEWESNGQP ENNYKTTPPV LDSDGSFFLY SKLTVDKSRW   420
QQGNVFSCSV MHEALHNHYT QKSLSLSPGK                                    450

SEQ ID NO: 21          moltype = DNA   length = 1353
FEATURE                Location/Qualifiers
source                 1..1353
                       mol_type = other DNA
                       organism = synthetic construct
SEQUENCE: 21
caagttcaac tccaacaatg gggtgccggg ctgctgaagc cgtccgaaac gttgagtctc    60
acctgcgccg tgtacggcgg cagtctttca ggctatccat ggtcctggat aaggcagccc   120
cccggcaagg gtctcgaatg gataggtgag acggacgtgt ctggctggac agattacaac   180
ccttctctga gtctcgcgt taccatttcc gtagatacaa gtaagaatca gttctcactg   240
aagctcagtt ctgtaaccgc tgccgacacc gcagtgtact attgtgcaag agatggacgc   300
aggatgggaa ctccaagctt tgacatttgg ggccagggta cgatggtgac tgtttcctcc   360
gcctcaacga aagggccatc tgtattccca ttggctccgg gtagtaagtc tacaagtggt   420
gggaccgcag cgctgggatg cctcgtcaag gattattttc ccgaaccagt aactgtaagt   480
tggaatagcg gggcattgac aagcggcgtt cacacctttc cagcggtgct tcaatcttct   540
ggactctact cattgagctc agttgtcacc gttccttcaa gttccttggg cacgcagaca   600
tatatctgca atgtgaatca taaaccttct aatacgaagg tcgataagaa agttgagcca   660
aaatcatgtg ataagacgca tacttgcccc ccctgcccag cccctgagct gttggcaggt   720
cccgatgtct ttctcttcc gcccaagccg aaggatacgc ttatgatctc caggactcct   780
gaggtgactt gcgtcgttgt cgacgtatcc cacgaagatc ctgaggtgaa gtttaattgg   840
tatgtcgacg gaagtagagg tgcataatgct aaaacgaaac ctcggaaga gcaatataat   900
tccacttaca gagtagtgag cgttctcaca gtttttgcatc aggactggct taacggaaag   960
gagtatataaa gtaaggtcag taacaaagct cttccagctc ccgaggagaa aacaatttca  1020
aaggcaaagg gccaacctag ggaaccgcag gtgtatactc tcccccccaag ccgcgaagaa  1080
atgacgaaaa accaggtgtc cctcacttgc ctggtcaaga gtttctatcc ttctgacata  1140
gcggtggagt gggagagtaa cggccaacca ataagaccac gcctccagtt              1200
ctggattccg atggatcatt ctttctgtac tctaaattga cggttgacaa atcccgctgg   1260
cagcagggaa acgtattttc atgttccgtg atgcatgaag ctttgcacaa tcactacact   1320
caaaagagtt tgagcttgtc accgggaaag taa                                1353

SEQ ID NO: 22          moltype = AA   length = 214
FEATURE                Location/Qualifiers
source                 1..214
                       mol_type = protein
                       organism = synthetic construct
SEQUENCE: 22
DIQMTQSPSS VSASVGDRVT ITCRASQDIN SFLAWYQQKP GKAPKLLIYA ASSLNSGVPS    60
RFSGSGSGTD FTLTISSLQP EDFATYYCQK SVYFPPTGQK GTKVEIKRTV AAPSVFIFPP   120
SDEQLKSGTA SVVCLLNNFY PREAKVQWKV DNALQSGNSQ ESVTEQDSKD STYSLSSTLT   180
LSKADYEKHK VYACEVTHQG LSSPVTKSFN RGEC                               214

SEQ ID NO: 23          moltype = DNA   length = 645
FEATURE                Location/Qualifiers
source                 1..645
                       mol_type = other DNA
                       organism = synthetic construct
SEQUENCE: 23
gacattcaga tgacgcaaag ccccagctct gtctcagctt ccgtgggtga tagggtgact    60
attacatgtc gagcctcaca agatattaat agctttcttg catggtatca gcaaaagcca   120
gggaaggcac ctaagctcct gatttatgct gcctcttctt tgaatagcgg ggtcccctcc   180
cgcttctcag gatctgggtc agggactgac ttcacgctga ctatatcctc actccaacca   240
gaagatttcg ccacttatta ctgccaaaaa tccgtatatt tcccgcccac attcggtggt   300
gggacaaaag tggaaatcaa gagaactgtc gctgccccat ctgttttcat ctttccaccg   360
agcgacgaac agctcaaaag cggcactgcg agtgttgtt gtctgctgaa taacttctat   420
cccagggaac aaaggtgca gtggaaggta gacaatgct tgcaatccgg gaatagtcag   480
gaatccgtca cggagcaaga cagtaaggac tccacgtatt ccttgagtag tacattgacc   540
ctcagtaaag cggattacga gaaacacaaa gtttacgctt gtgaagtaac gcatcagggg   600
ttgtccagtc cggttaccaa atccttcaat cggggagagt gttga                   645

SEQ ID NO: 24          moltype = DNA   length = 1004
FEATURE                Location/Qualifiers
source                 1..1004
                       mol_type = other DNA
                       organism = synthetic construct
SEQUENCE: 24
gctagcacca agggcccatc ggtcttcccc ctggcaccct cctccaagag cacctctggg    60
ggcacagcgg ccctgggctg cctggtcaag gactacttcc ccgaaccggt gacggtgtcg   120
tggaactcag gcgccctgac cagcggcgtg cacaccttcc cggctgtcct acagtcctca   180
ggactctact ccctcagcag cgtggtgacc gtgccctcca gcagcttggg cacccagacc   240
tacatctgca acgtgaatca caagcccagc aacaccaagg tggacaagaa agttgagccc   300
```

-continued

```
aaatcttgtg  acaaaactca  cacatgccca  ccgtgcccag  cacctgaact  cctggcggga   360
ccggacgtct  tcctcttccc  cccaaaaccc  aaggacaccc  tcatgatctc  ccggacccct   420
gaggtcacat  gcgtggtggt  ggacgtgagc  cacgaagacc  ctgaggtcaa  gttcaactgg   480
tacgtggacg  gcgtggaggt  gcataatgcc  aagacaaagc  cgcgggagga  gcagtacaac   540
agcacgtacc  gtgtggtcag  cgtcctcacc  gtcctgcacc  aggactggct  gaatggcaag   600
gagtacaagt  gcaaggtctc  caacaaagcc  ctcccagccc  ccgaggagaa  aaccatctcc   660
aaagccaaag  ggcagccccg  agaaccacag  gtgtacaccc  tgcccccatc  ccgggaggag   720
atgaccaaga  accaggtcag  cctgacctgc  ctggtcaaag  gcttctatcc  cagcgacatc   780
gccgtggagt  gggagagcaa  tgggcagccg  gagaacaact  acaagaccac  gcctcccgtg   840
ctggactccg  acggctcctt  cttcctctac  agcaagctca  ccgtggacaa  gagcaggtgg   900
cagcagggga  acgtcttctc  atgctccgtg  atgcacgagg  ctctgcacaa  ccactacacg   960
cagaagagcc  tctccctgtc  tccgggtaaa  tgagtcctag  ctgg                     1004

SEQ ID NO: 25          moltype = AA  length = 330
FEATURE                Location/Qualifiers
source                 1..330
                       mol_type = protein
                       organism = synthetic construct
SEQUENCE: 25
ASTKGPSVFP  LAPSSKSTSG  GTAALGCLVK  DYFPEPVTVS  WNSGALTSGV  HTFPAVLQSS   60
GLYSLSSVVT  VPSSSLGTQT  YICNVNHKPS  NTKVDKKVEP  KSCDKTHTCP  PCPAPELLAG   120
PDVFLFPPKP  KDTLMISRTP  EVTCVVVDVS  HEDPEVKFNW  YVDGVEVHNA  KTKPREEQYN   180
STYRVVSVLT  VLHQDWLNGK  EYKCKVSNKA  LPAPEEKTIS  KAKGQPREPQ  VYTLPPSREE   240
MTKNQVSLTC  LVKGFYPSDI  AVEWESNGQP  ENNYKTTPPV  LDSDGSFFLY  SKLTVDKSRW   300
QQGNVFSCSV  MHEALHNHYT  QKSLSLSPGK                                       330
```